US007117188B2

(12) United States Patent
Guyon et al.

(10) Patent No.: US 7,117,188 B2
(45) Date of Patent: Oct. 3, 2006

(54) METHODS OF IDENTIFYING PATTERNS IN BIOLOGICAL SYSTEMS AND USES THEREOF

(75) Inventors: Isabelle Guyon, Berkeley, CA (US); Jason Aaron Edward Weston, New York, NY (US)

(73) Assignee: Health Discovery Corporation, Savannah, GA (US)

( * ) Notice: Subject to any disclaimer, the term of this patent is extended or adjusted under 35 U.S.C. 154(b) by 647 days.

(21) Appl. No.: 10/057,849

(22) Filed: Jan. 24, 2002

(65) Prior Publication Data

US 2003/0172043 A1 Sep. 11, 2003

Related U.S. Application Data

(63) Continuation-in-part of application No. 09/633,410, filed on Aug. 7, 2000, now Pat. No. 6,882,990, which is a continuation-in-part of application No. 09/578,011, filed on May 24, 2000, now Pat. No. 6,658,395, which is a continuation-in-part of application No. 09/568,301, filed on May 9, 2000, now Pat. No. 6,427,141, which is a continuation-in-part of application No. 09/303,387, filed on May 1, 1999, now Pat. No. 6,128,608.

(60) Provisional application No. 60/298,757, filed on Jun. 15, 2001, provisional application No. 60/275,760, filed on Mar. 14, 2001, provisional application No. 60/263,696, filed on Jan. 24, 2001, provisional application No. 60/083,961, filed on May 1, 1998.

(51) Int. Cl.
*G06F 15/18* (2006.01)

(52) U.S. Cl. .......................................... 706/20; 706/19

(58) Field of Classification Search .................. 706/20, 706/19

See application file for complete search history.

(56) References Cited

U.S. PATENT DOCUMENTS

| | | | | |
|---|---|---|---|---|
| 4,881,178 | A | 11/1989 | Holland | |
| 5,138,694 | A | 8/1992 | Hamilton | |
| 5,649,068 | A | 7/1997 | Boser | |
| 5,809,144 | A | 9/1998 | Sirbu | |
| 5,875,108 | A * | 2/1999 | Hoffberg et al. | 700/17 |
| 5,950,146 | A | 9/1999 | Vapnik | |
| 6,128,608 | A | 10/2000 | Barnhill | 706/16 |
| 6,128,609 | A | 10/2000 | Barnhill | |
| 6,134,344 | A | 10/2000 | Burges | |
| 6,157,921 | A | 12/2000 | Barnhill | 706/16 |
| 6,306,087 | B1 * | 10/2001 | Barnhill et al. | 600/300 |
| 6,427,141 | B1 | 7/2002 | Barnhill | 706/16 |
| 6,658,395 | B1 | 12/2003 | Barnhill | |
| 6,714,925 | B1 | 3/2004 | Barnhill | |
| 6,760,715 | B1 | 7/2004 | Barnhill | |
| 6,789,069 | B1 | 9/2004 | Barnhill | |
| 6,882,990 | B1 * | 4/2005 | Barnhill et al. | 706/16 |

OTHER PUBLICATIONS

Sartori, Neural Network Training Quadratic Optimization, Proceedings of International Symposium on Circuits and systems, May 1992.*

(Continued)

*Primary Examiner*—George Davis
(74) *Attorney, Agent, or Firm*—Eleanor M. Musick; Procopio, Cory, Hargreaves & Savitch LLP

(57) ABSTRACT

The methods, systems and devices of the present invention comprise use of Support Vector Machines and RFE (Recursive Feature Elimination) for the identification of patterns that are useful for medical diagnosis, prognosis and treatment. SVM-RFE can be used with varied data sets.

23 Claims, 29 Drawing Sheets

OTHER PUBLICATIONS

Cook, "Training MLPs via the epectation maximum algorithm", IEEE Fourth International Conference on Artificial Neural Networks, Jun. 1995.*

Alon, U., et al., "Broad patterns of gene expression revealed by clustering analysis of tumor and normal colon tissues probed by oligonucleotide arrays", *Proc. Natl. Acad. Sci. USA*, Jun. 1999, pp. 6745-6750, vol. 96, Cell Biology.

Blum, A.L., et al., "Selection of Relevant Features and Examples in Machine Learning", *Artificial Intelligence*, Dec. 1997, pp. 245-271, vol. 97.

Bredensteiner, E.J., et al., "Multicategory Classification by Support Vector Machines", *Computation Optimizations and Applications*, 1999, pp. 53-79, vol. 12.

Brown, M.P.S., et al., "Knowledge-based analysis of microarray gene expression data by using support vector machines", *Proc. Natl. Acad. Sci. USA*, Jan. 4, 2000, pp. 262-267, vol. 97, No. 1.

Devijver, P., et al., *Pattern Recognition. A Statistical Approach*, 1982, pp. 218-219, Prentice-Hall International, London.

Furey, T.S., et al., "Support vector machine classification and validation of cancer tissue samples using microarray expression data", *Bioinformatics*, 2000, pp. 906-914, vol. 16, No. 10.

Golub, T.R., et al., "Molecular Classification of Cancer: Class Discovery and Class Prediction by Gene Expression Monitoring", *Science*, Oct. 15, 1999, pp. 531-537, vol. 286.

Guyon, I., et al., "An Introduction to Variable and Feature Selection", *Journal of Machine Learning Research*, 2003, pp. 1157-1182, vol. 3.

Hastie, T., et al., "Gene Shaving: a New Class of Clustering Methods for Expression Arrays", Technical Report, Stanford University, 2000, pp. 1-40.

Kohavi, R., "The Power of Decision Tables", *European Conference on Machine Learning* (*ECML*), 1995, 16 pages.

Kohavi, R., and John, G.H., "Wrappers for Feature Subset Selection", *Artificial Intelligence*, Dec. 1997, pp. 273-324, vol. 97, Issue 1-2, Special issue on relevance.

Le Cun, Y., et al., "Optimal Brain Damage", *Advances in Neural Information Processing Systems 2*, 1990, pp. 598-605.

Mukherjee, S., et al., "Support Vector Machine Classification of Microarray Data", Technical Report CBCL Paper 182, AJ, Memo 1676 M.I.T., 1998.

Weston, J., et al., "Feature Selection for SVMs", *Proc. 15th Conference on Neural Information Processing Systems* (*NIPS*), 2000, pp. 668-674.

Zhang, X. and Wong, W., "Recursive Sample Classification and Gene Selection based on SVM: Method and Software Description", Technical Report, Department of Biostatistics, Harvard School of Public Health, 2001, 5 pages.

Gupta, P., et al., "Beam Search for Feature Selection in Automatic SVM Defect Classification", *16th International Conference on Pattern Recognition* (*ICPR'02*), Aug. 2002, p. 20212, vol. 2 (abstract only).

* cited by examiner

| 406a | 406b | 406c | 406d | 406e | 406f |
|---|---|---|---|---|---|
| 41 | 75 | 95 | 29 | 8 | 1 |
| 47 | 64 | 45 | 26 | 4 | 1 |
| 34 | 35 | 17 | 11 | 5 | 1 |
| 48 | 5 | 137 | 18 | 2 | 1 |
| 35 | 29 | 48 | 21 | 9 | 1 |
| 49 | 19 | 69 | 11 | 7 | 1 |
| 42 | 8 | 10 | 12 | 2 | 1 |
| 44 | 3 | 12 | 14 | 1 | 1 |
| 37 | 57 | 19 | 20 | 7 | 1 |
| 48 | 17 | 14 | 12 | 1 | 1 |
| 39 | 1 | 10 | 17 | 8 | 1 |
| 44 | 21 | 14 | 17 | 1 | 1 |
| 34 | 2 | 9 | 12 | 1 | 1 |
| 31 | 10 | 10 | 16 | 0 | 1 |
| 42 | 252 | 452 | 25 | 0 | 1 |
| 42 | 59 | 693 | 19 | 1 | -1 |
| 36 | 5 | 51 | 12 | 1 | -1 |
| 38 | 1 | 10 | 19 | 1 | -1 |
| 36 | 43 | 89 | 9 | 1 | -1 |
| 42 | 16 | 10 | 13 | 4 | -1 |
| 47 | 19 | 20 | 12 | 1 | -1 |
| 49 | 14 | 128 | 21 | 4 | -1 |
| 38 | 169 | 315 | 36 | 0 | -1 |
| 33 | 2 | 12 | 8 | 0 | -1 |
| 46 | 41 | 308 | 23 | 5 | -1 |
| 44 | 54 | 115 | 29 | 2 | -1 |
| 31 | 4 | 3 | 20 | 1 | -1 |
| 49 | 1 | 18 | 27 | 2 | -1 |
| 48 | 34 | 355 | 19 | 3 | -1 |
| 44 | 29 | 19 | 20 | 2 | -1 |
| 42 | 207 | 11 | 10 | 3 | -1 |
| 43 | 62 | 53 | 26 | 1 | -1 |
| 43 | 108 | 293 | 4 | 0 | -1 |
| 35 | 25 | 13 | 24 | 1 | -1 |
| 35 | 5 | 5 | 16 | 1 | -1 |
| 45 | 54 | 17 | 19 | 8 | -1 |
| 41 | 4 | 10 | 15 | 4 | -1 |
| 40 | 8 | 12 | 8 | 0 | -1 |
| 42 | 25 | 78 | 21 | 2 | -1 |
| 46 | 30 | 105 | 11 | 5 | -1 |
| 48 | 72 | 94 | 15 | 1 | -1 |
| 36 | 3 | 10 | 7 | 0 | -1 |
| 46 | 165 | 12 | 17 | 5 | -1 |
| 47 | 22 | 10 | 26 | 2 | -1 |
| 48 | 3 | 10 | 21 | 0 | -1 |
| 40 | 4 | 10 | 12 | 0 | -1 |

402

| | | | | | |
|---|---|---|---|---|---|
| 32 | 3 | 10 | 14 | 6 | 1 |
| 36 | 51 | 167 | 11 | 3 | 1 |
| 39 | 4 | 15 | 31 | 25 | 1 |
| 46 | 2 | 10 | 8 | 0 | 1 |
| 28 | 12 | 36 | 25 | 23 | 1 |
| 32 | 23 | 50 | 19 | 0 | 1 |
| 44 | 26 | 10 | 21 | 4 | 1 |
| 47 | 32 | 11 | 21 | 7 | 1 |
| 42 | 32 | 41 | 21 | 18 | -1 |
| 42 | 2 | 10 | 14 | 0 | -1 |
| 36 | 10 | 1 | 16 | 1 | -1 |
| 47 | 5 | 6 | 22 | 1 | -1 |
| 34 | 18 | 6 | 13 | 2 | -1 |
| 34 | 9 | 10 | 29 | 0 | -1 |
| 37 | 6 | 10 | 16 | 0 | -1 |
| 38 | 42 | 46 | 14 | 6 | -1 |
| 32 | 98 | 11 | 11 | 0 | -1 |
| 37 | 39 | 10 | 13 | 1 | -1 |
| 45 | 17 | 267 | 20 | 4 | -1 |
| 39 | 93 | 134 | 12 | 1 | -1 |
| 43 | 47 | 11 | 19 | 11 | -1 |
| 46 | 6 | 10 | 13 | 1 | -1 |
| 49 | 1 | 4 | 19 | 6 | -1 |
| 46 | 172 | 302 | 9 | 3 | -1 |

| 606a | 606a1 | 606a2 | 606a3 | 606b | 606b1-3 | | | 606c | 606c1-3 | | | 606d | 606d1-3 | | | 606e | 606e1-3 | | | 606f |
|---|---|---|---|---|---|---|---|---|---|---|---|---|---|---|---|---|---|---|---|---|
| 41 | 0 | 0 | 1 | 75 | 0 | 0 | 1 | 95 | 0 | 0 | 1 | 29 | 0 | 0 | 1 | 8 | 0 | 0 | 1 | 1 |
| 47 | 0 | 0 | 1 | 64 | 0 | 0 | 1 | 45 | 0 | 0 | 1 | 26 | 0 | 0 | 1 | 4 | 0 | 0 | 1 | 1 |
| 34 | 0 | 1 | 0 | 35 | 0 | 0 | 1 | 17 | 0 | 1 | 0 | 11 | 0 | 0 | 1 | 5 | 0 | 0 | 1 | 1 |
| 48 | 0 | 0 | 1 | 5 | 1 | 0 | 0 | 137 | 0 | 0 | 1 | 18 | 0 | 0 | 1 | 2 | 0 | 0 | 1 | 1 |
| 35 | 0 | 0 | 1 | 29 | 0 | 0 | 1 | 48 | 0 | 0 | 1 | 21 | 0 | 0 | 1 | 9 | 0 | 0 | 1 | 1 |
| 49 | 0 | 0 | 1 | 19 | 0 | 1 | 0 | 69 | 0 | 0 | 1 | 11 | 0 | 0 | 1 | 7 | 0 | 0 | 1 | 1 |
| 42 | 0 | 0 | 1 | 8 | 1 | 0 | 0 | 10 | 1 | 0 | 0 | 12 | 0 | 0 | 1 | 2 | 0 | 0 | 1 | 1 |
| 44 | 0 | 0 | 1 | 3 | 1 | 0 | 0 | 12 | 0 | 1 | 0 | 14 | 0 | 0 | 1 | 1 | 0 | 0 | 1 | 1 |
| 37 | 0 | 0 | 1 | 57 | 0 | 0 | 1 | 19 | 0 | 0 | 1 | 20 | 0 | 0 | 1 | 7 | 0 | 0 | 1 | 1 |
| 48 | 0 | 0 | 1 | 17 | 0 | 1 | 0 | 14 | 0 | 1 | 0 | 12 | 0 | 0 | 1 | 1 | 0 | 0 | 1 | 1 |
| 39 | 0 | 0 | 1 | 1 | 1 | 0 | 0 | 10 | 1 | 0 | 0 | 17 | 0 | 0 | 1 | 8 | 0 | 0 | 1 | 1 |
| 44 | 0 | 0 | 1 | 21 | 0 | 1 | 0 | 14 | 0 | 1 | 0 | 17 | 0 | 0 | 1 | 1 | 0 | 0 | 1 | 1 |
| 34 | 0 | 1 | 0 | 2 | 1 | 0 | 0 | 9 | 1 | 0 | 0 | 12 | 0 | 0 | 1 | 1 | 0 | 0 | 1 | 1 |
| 31 | 1 | 0 | 0 | 10 | 1 | 0 | 0 | 10 | 1 | 0 | 0 | 16 | 0 | 0 | 1 | 0 | 1 | 0 | 0 | 1 |
| 42 | 0 | 0 | 1 | 252 | 0 | 0 | 1 | 452 | 0 | 0 | 1 | 25 | 0 | 0 | 1 | 0 | 1 | 0 | 0 | 1 |
| 42 | 0 | 0 | 1 | 59 | 0 | 0 | 1 | 693 | 0 | 0 | 1 | 19 | 0 | 0 | 1 | 1 | 0 | 0 | 1 | -1 |
| 36 | 0 | 0 | 1 | 5 | 1 | 0 | 0 | 51 | 0 | 0 | 1 | 12 | 0 | 0 | 1 | 1 | 0 | 0 | 1 | -1 |
| 38 | 0 | 0 | 1 | 1 | 1 | 0 | 0 | 10 | 1 | 0 | 0 | 19 | 0 | 0 | 1 | 1 | 0 | 0 | 1 | -1 |
| 36 | 0 | 0 | 1 | 43 | 0 | 0 | 1 | 89 | 0 | 0 | 1 | 9 | 0 | 1 | 0 | 1 | 0 | 1 | 0 | -1 |
| 42 | 0 | 0 | 1 | 16 | 1 | 0 | 0 | 10 | 1 | 0 | 0 | 13 | 0 | 0 | 1 | 4 | 0 | 0 | 1 | -1 |
| 47 | 0 | 0 | 1 | 19 | 0 | 1 | 0 | 20 | 0 | 0 | 1 | 12 | 0 | 0 | 1 | 1 | 0 | 0 | 1 | -1 |
| 49 | 0 | 0 | 1 | 14 | 1 | 0 | 0 | 128 | 0 | 0 | 1 | 21 | 0 | 0 | 1 | 4 | 0 | 0 | 1 | -1 |
| 38 | 0 | 0 | 1 | 169 | 0 | 0 | 1 | 315 | 0 | 0 | 1 | 36 | 0 | 0 | 1 | 0 | 1 | 0 | 0 | -1 |
| 33 | 1 | 0 | 0 | 2 | 1 | 0 | 0 | 12 | 0 | 1 | 0 | 8 | 0 | 1 | 0 | 0 | 1 | 0 | 0 | -1 |
| 46 | 0 | 0 | 1 | 41 | 0 | 0 | 1 | 308 | 0 | 0 | 1 | 23 | 0 | 0 | 1 | 5 | 0 | 0 | 1 | -1 |
| 44 | 0 | 0 | 1 | 54 | 0 | 0 | 1 | 115 | 0 | 0 | 1 | 29 | 0 | 0 | 1 | 2 | 0 | 0 | 1 | -1 |
| 31 | 1 | 0 | 0 | 4 | 1 | 0 | 0 | 3 | 1 | 0 | 0 | 20 | 0 | 0 | 1 | 1 | 0 | 0 | 1 | -1 |
| 49 | 0 | 0 | 1 | 1 | 1 | 0 | 0 | 18 | 0 | 1 | 0 | 27 | 0 | 0 | 1 | 2 | 0 | 0 | 1 | -1 |
| 48 | 0 | 0 | 1 | 34 | 0 | 0 | 1 | 355 | 0 | 0 | 1 | 19 | 0 | 0 | 1 | 3 | 0 | 0 | 1 | -1 |
| 44 | 0 | 0 | 1 | 29 | 0 | 0 | 1 | 19 | 0 | 0 | 1 | 20 | 0 | 1 | 1 | 2 | 0 | 0 | 1 | -1 |
| 42 | 0 | 0 | 1 | 207 | 0 | 0 | 1 | 11 | 0 | 1 | 0 | 10 | 0 | 0 | 1 | 3 | 0 | 0 | 1 | -1 |
| 43 | 0 | 0 | 1 | 62 | 0 | 0 | 1 | 53 | 0 | 0 | 1 | 26 | 0 | 0 | 1 | 1 | 0 | 0 | 1 | -1 |
| 43 | 0 | 0 | 1 | 108 | 0 | 0 | 1 | 293 | 0 | 0 | 1 | 4 | 1 | 0 | 0 | 0 | 1 | 0 | 0 | -1 |
| 35 | 0 | 0 | 1 | 25 | 0 | 0 | 1 | 13 | 0 | 1 | 0 | 24 | 0 | 1 | 1 | 1 | 0 | 0 | 1 | -1 |
| 35 | 0 | 0 | 1 | 5 | 1 | 0 | 0 | 5 | 1 | 0 | 0 | 16 | 0 | 0 | 1 | 1 | 0 | 0 | 1 | -1 |
| 45 | 0 | 0 | 1 | 54 | 0 | 0 | 1 | 17 | 0 | 1 | 0 | 19 | 0 | 0 | 1 | 8 | 0 | 0 | 1 | -1 |
| 41 | 0 | 0 | 1 | 4 | 1 | 0 | 0 | 10 | 1 | 0 | 0 | 15 | 0 | 0 | 1 | 4 | 0 | 0 | 1 | -1 |
| 40 | 0 | 0 | 1 | 8 | 1 | 0 | 0 | 12 | 0 | 1 | 0 | 8 | 0 | 1 | 0 | 0 | 1 | 0 | 0 | -1 |
| 42 | 0 | 0 | 1 | 25 | 0 | 0 | 1 | 78 | 0 | 0 | 1 | 21 | 0 | 0 | 1 | 2 | 0 | 0 | 1 | -1 |
| 46 | 0 | 0 | 1 | 30 | 0 | 0 | 1 | 105 | 0 | 0 | 1 | 11 | 0 | 0 | 1 | 5 | 0 | 0 | 1 | -1 |
| 48 | 0 | 0 | 1 | 72 | 0 | 0 | 1 | 94 | 0 | 0 | 1 | 15 | 0 | 0 | 1 | 1 | 0 | 0 | 1 | -1 |
| 36 | 0 | 0 | 1 | 3 | 1 | 0 | 0 | 10 | 1 | 0 | 0 | 7 | 0 | 1 | 0 | 0 | 1 | 0 | 0 | -1 |
| 46 | 0 | 0 | 1 | 165 | 0 | 0 | 1 | 12 | 0 | 1 | 0 | 17 | 0 | 0 | 1 | 5 | 0 | 0 | 1 | -1 |
| 47 | 0 | 0 | 1 | 22 | 0 | 0 | 1 | 10 | 1 | 0 | 0 | 26 | 0 | 0 | 1 | 2 | 0 | 0 | 1 | -1 |
| 48 | 0 | 0 | 1 | 3 | 1 | 0 | 0 | 10 | 1 | 0 | 0 | 21 | 0 | 0 | 1 | 0 | 1 | 0 | 0 | -1 |
| 40 | 0 | 0 | 1 | 4 | 1 | 0 | 0 | 10 | 1 | 0 | 0 | 12 | 0 | 0 | 1 | 0 | 1 | 0 | 0 | -1 |

604

| 606a | 606a1 | 606a2 | 606a3 | 606b | 606b1-3 | | | 606c | 606c1-3 | | | 606d | 606d1-3 | | | 606e | 606e1-3 | | | 606f |
|---|---|---|---|---|---|---|---|---|---|---|---|---|---|---|---|---|---|---|---|---|
| 32 | 1 | 0 | 0 | 3 | 1 | 0 | 0 | 10 | 1 | 0 | 0 | 14 | 0 | 0 | 1 | 6 | 0 | 0 | 1 | 1 |
| 36 | 0 | 0 | 1 | 51 | .0 | 0 | 1 | 167 | 0 | 0 | 1 | 11 | 0 | 0 | 1 | 3 | 0 | 0 | 1 | 1 |
| 39 | 0 | 0 | 1 | 4 | 1 | 0 | 0 | 15 | 0 | 1 | 0 | 31 | 0 | 0 | 1 | 25 | 0 | 0 | 1 | 1 |
| 46 | 0 | 0 | 0 | 2 | 1 | 0 | 0 | 10 | 1 | 0 | 0 | 8 | 0 | 1 | 0 | 0 | 1 | 0 | 0 | 1 |
| 28 | 1 | 0 | 0 | 12 | 1 | 0 | 0 | 36 | 0 | 0 | 1 | 25 | 0 | 0 | 1 | 23 | 0 | 0 | 1 | 1 |
| 32 | 1 | 0 | 1 | 23 | 0 | 0 | 1 | 50 | 0 | 0 | 1 | 19 | 0 | 0 | 1 | 0 | 1 | 0 | 0 | 1 |
| 44 | 0 | 0 | 1 | 26 | 0 | 0 | 1 | 10 | 1 | 0 | 0 | 21 | 0 | 0 | 1 | 4 | 0 | 0 | 1 | 1 |
| 47 | 0 | 0 | 1 | 32 | 0 | 0 | 1 | 11 | 0 | 1 | 0 | 21 | 0 | 0 | 1 | 7 | 0 | 0 | 1 | 1 |
| 42 | 0 | 0 | 1 | 32 | 0 | 0 | 1 | 41 | 0 | 0 | 1 | 21 | 0 | 0 | 1 | 18 | 0 | 0 | 1 | -1 |
| 42 | 0 | 0 | 1 | 2 | 1 | 0 | 0 | 10 | 1 | 0 | 0 | 14 | 0 | 0 | 1 | 0 | 1 | 0 | 0 | -1 |
| 36 | 0 | 0 | 1 | 10 | 1 | 0 | 0 | 1 | 1 | 0 | 0 | 16 | 0 | 0 | 1 | 1 | 0 | 0 | 1 | -1 |
| 47 | 0 | 0 | 1 | 5 | 1 | 0 | 0 | 6 | 1 | 0 | 0 | 22 | 0 | 0 | 1 | 1 | 0 | 0 | 1 | -1 |
| 34 | 0 | 1 | 0 | 18 | 0 | 1 | 0 | 6 | 1 | 0 | 0 | 13 | 0 | 0 | 1 | 2 | 0 | 0 | 1 | -1 |
| 34 | 0 | 1 | 0 | 9 | 1 | 0 | 0 | 10 | 1 | 0 | 0 | 29 | 0 | 0 | 1 | 0 | 1 | 0 | 0 | -1 |
| 37 | 0 | 0 | 1 | 6 | 1 | 0 | 0 | 10 | 1 | 0 | 0 | 16 | 0 | 0 | 1 | 0 | 1 | 0 | 0 | -1 |
| 38 | 0 | 0 | 1 | 42 | 0 | 0 | 1 | 46 | 0 | 0 | 1 | 14 | 0 | 0 | 1 | 6 | 0 | 0 | 1 | -1 |
| 32 | 1 | 0 | 0 | 98 | 0 | 0 | 1 | 11 | 0 | 1 | 0 | 11 | 0 | 0 | 1 | 0 | 1 | 0 | 0 | -1 |
| 37 | 0 | 0 | 1 | 39 | 0 | 0 | 1 | 10 | 1 | 0 | 0 | 13 | 0 | 0 | 1 | 1 | 0 | 0 | 1 | -1 |
| 45 | 0 | 0 | 1 | 17 | 0 | 1 | 0 | 267 | 0 | 0 | 1 | 20 | 0 | 0 | 1 | 4 | 0 | 0 | 1 | -1 |
| 39 | 0 | 0 | 1 | 93 | 0 | 0 | 1 | 134 | 0 | 0 | 1 | 12 | 0 | 0 | 1 | 1 | 0 | 0 | 1 | -1 |
| 43 | 0 | 0 | 1 | 47 | 0 | 0 | 1 | 11 | 0 | 1 | 0 | 19 | 0 | 0 | 1 | 11 | 0 | 0 | 1 | -1 |
| 46 | 0 | 0 | 1 | 6 | 1 | 0 | 0 | 10 | 1 | 0 | 0 | 13 | 0 | 0 | 1 | 1 | 0 | 0 | 1 | -1 |
| 49 | 0 | 0 | 1 | 1 | 1 | 0 | 0 | 4 | 1 | 0 | 0 | 19 | 0 | 0 | 1 | 6 | 0 | 0 | 1 | -1 |
| 46 | 0 | 0 | 1 | 172 | 0 | 0 | 1 | 302 | 0 | 0 | 1 | 9 | 0 | 1 | 0 | 3 | 0 | 0 | 1 | -1 |

FIG. 5

METHODS OF IDENTIFYING PATTERNS IN BIOLOGICAL SYSTEMS AND USES THEREOF

RELATED APPLICATIONS

The present application claims priority of each of U.S. Provisional Patent Application Ser. No. 60/263,696, filed Jan. 24, 2001, U.S. Provisional Patent Application Ser. No. 60/298,757, filed Jun. 15, 2001, and U.S. Provisional Patent Application Ser. No. 60/275,760, filed Mar. 14, 2001, and is a continuation-in-part of U.S. patent application Ser. No. 09/633,410, filed Aug. 7, 2000, now issued as U.S. Pat. No. 6,882,990, which is a continuation-in-part of application Ser. No. 09/578,011, filed May 24, 2000, now issued as U.S. Pat. No. 6,658,395, which is a continuation-in-part of application Ser. No. 09/568,301, filed May 9, 2000, now issued as U.S. Pat. No. 6,427,141, which is a continuation of application Ser. No. 09/303,387, filed May 1, 1999, now issued as U.S. Pat. No. 6,128,608, which claims priority to U.S. provisional application Ser. No. 60/083,961, filed May 1, 1998. This application is related to application Ser. No. 09/633,615, now abandoned, Ser. No. 09/633,616, now issued as U.S. Pat. No. 6,760,715, and Ser. No. 09/633,850, now issued as U.S. Pat. No. 6,789,069, all filed Aug. 7, 2000, which are also continuations-in-part of application Ser. No. 09/578,011. This application is also related to application Ser. No. 09/303,386, now abandoned, and Ser. No. 09/305,345, now issued as U.S. Pat. No. 6,157,921, both filed May 1, 1999, and to application Ser. No. 09/715,832, filed Nov. 14, 2000, now abandoned, all of which also claim priority to provisional application Ser. No. 60/083,961.

TECHNICAL FIELD

The present invention relates to the use of learning machines to identify relevant patterns in biological systems such as genes, gene products, proteins, lipids, and combinations of the same. These patterns in biological systems can be used to diagnose and prognose abnormal physiological states. In addition, the patterns that can be detected using the present invention can be used to develop therapeutic agents.

BACKGROUND OF THE INVENTION

Enormous amounts of data about organisms are being generated in the sequencing of genomes. Using this information to provide treatments and therapies for individuals will require an in-depth understanding of the gathered information. Efforts using genomic information have already led to the development of gene expression investigational devices. One of the most currently promising devices is the gene chip. Gene chips have arrays of oligonucleotide probes attached a solid base structure. Such devices are described in U.S. Pat. Nos. 5,837,832 and 5,143,854, herein incorporated by reference in their entirety. The oligonucleotide probes present on the chip can be used to determine whether a target nucleic acid has a nucleotide sequence identical to or different from a specific reference sequence. The array of probes comprise probes that are complementary to the reference sequence as well as probes that differ by one of more bases from the complementary probes.

The gene chips are capable of containing large arrays of oligonucleotides on very small chips. A variety of methods for measuring hybridization intensity data to determine which probes are hybridizing is known in the art. Methods for detecting hybridization include fluorescent, radioactive, enzymatic, chemoluminescent, bioluminescent and other detection systems.

Older, but still usable, methods such as gel electrophosesis and hybridization to gel blots or dot blots are also useful for determining genetic sequence information. Capture and detection systems for solution hybridization and in situ hybridization methods are also used for determining information about a genome. Additionally, former and currently used methods for defining large parts of genomic sequences, such as chromosome walking and phage library establishment, are used to gain knowledge about genomes.

Large amounts of information regarding the sequence, regulation, activation, binding sites and internal coding signals can be generated by the methods known in the art. In fact, the amount of data being generated by such methods hinders the derivation of useful information. Human researchers, when aided by advanced learning tools such as neural networks can only derive crude models of the underlying processes represented in the large, feature-rich datasets.

Another area of biological investigation that can generate a huge amount of data is the emerging field of proteomics. Proteomics is the study of the group of proteins encoded and regulated by a genome. This field represents a new focus on analyzing proteins, regulation of protein levels and the relationship to gene regulation and expression. Understanding the normal or pathological state of the proteome of a person or a population provides information for the prognosis or diagnosis of disease, development of drug or genetic treatments, or enzyme replacement therapies. Current methods of studying the proteome involve 2-dimensional (2-D) gel electrophoresis of the proteins followed by analysis by mass spectrophotometry. A pattern of proteins at any particular time or stage in pathologenesis or treatment can be observed by 2-D gel electrophoresis. Problems arise in identifying the thousands of proteins that are found in cells that have been separated on the 2-D gels. The mass spectrophotometer is used to identify a protein isolated from the gel by identifying the amino acid sequence and comparing it to known sequence databases. Unfortunately, these methods require multiple steps to analyze a small portion of the proteome.

In recent years, technologies have been developed that can relate gene expression to protein production structure and function. Automated high-throughput analysis, nucleic acid analysis and bioinformatics technologies have aided in the ability to probe genomes and to link gene mutations and expression with disease predisposition and progression. The current analytical methods are limited in their abilities to manage the large amounts of data generated by these technologies.

One of the more recent advances in determining the functioning parameters of biological systems is the analysis of correlation of genomic information with protein functioning to elucidate the relationship between gene expression, protein function and interaction, and disease states or progression. Genomic activation or expression does not always mean direct changes in protein production levels or activity. Alternative processing of mRNA or post-transcriptional or post-translational regulatory mechanisms may cause the activity of one gene to result in multiple proteins, all of which are slightly different with different migration patterns and biological activities. The human genome potentially contains 30,000 genes but the human proteome is believed to be 50 to 100 times larger. Currently, there are no methods, systems or devices for adequately analyzing the data generated by such biological investigations into the genome and proteome.

Knowledge discovery is the most desirable end product of data collection. Recent advancements in database technology have lead to an explosive growth in systems and methods for generating, collecting and storing vast amounts of data. While database technology enables efficient collection and storage of large data sets, the challenge of facilitating human comprehension of the information in this data is growing ever more difficult. With many existing techniques the problem has become unapproachable. Thus, there remains a need for a new generation of automated knowledge discovery tools.

As a specific example, the Human Genome Project is populating a multi-gigabyte database describing the human genetic code. Before this mapping of the human genome is complete, the size of the database is expected to grow significantly. The vast amount of data in such a database overwhelms traditional tools for data analysis, such as spreadsheets and ad hoc queries. Traditional methods of data analysis may be used to create informative reports from data, but do not have the ability to intelligently and automatically assist humans in analyzing and finding patterns of useful knowledge in vast amounts of data. Likewise, using traditionally accepted reference ranges and standards for interpretation, it is often impossible for humans to identify patterns of useful knowledge even with very small amounts of data.

In recent years, machine-learning approaches for data analysis have been widely explored for recognizing patterns which, in turn, allow extraction of significant information contained within a large data set which may also include data that provide nothing more than irrelevant detail. Learning machines comprise algorithms that may be trained to generalize using data with known outcomes. Trained learning machine algorithms may then be applied to predict the outcome in cases of unknown outcome. Machine-learning approaches, which include neural networks, hidden Markov models, belief networks and support vector machines, are ideally suited for domains characterized by the existence of large amounts of data, noisy patterns and the absence of general theories.

The majority of learning machines that have been investigated are neural networks trained using back-propagation, a gradient-based method in which errors in classification of training data are propagated backwards through the network to adjust the bias weights of the network elements until the mean squared error is minimized. A significant drawback of back-propagation neural networks is that the empirical risk function may have many local minimums, a case that can easily obscure the optimal solution from discovery. Standard optimization procedures employed by back-propagation neural networks may converge to a minimum, but the neural network method cannot guarantee that even a localized minimum is attained, much less the desired global minimum. The quality of the solution obtained from a neural network depends on many factors. In particular, the skill of the practitioner implementing the neural network determines the ultimate benefit, but even factors as seemingly benign as the random selection of initial weights can lead to poor results. Furthermore, the convergence of the gradient-based method used in neural network learning is inherently slow. A further drawback is that the sigmoid function has a scaling factor, which affects the quality of approximation. Possibly the largest limiting factor of neural networks as related to knowledge discovery is the "curse of dimensionality" associated with the disproportionate growth in required computational time and power for each additional feature or dimension in the training data.

The shortcomings of neural networks are overcome using support vector machines. In general terms, a support vector machine maps input vectors into high dimensional feature space through non-linear mapping function, chosen a priori. In this high dimensional feature space, an optimal separating hyperplane is constructed. The optimal hyperplane is then used to determine things such as class separations, regression fit, or accuracy in density estimation.

Within a support vector machine, the dimensionally of the feature space may be huge. For example, a fourth degree polynomial mapping function causes a 200 dimensional input space to be mapped into a 1.6 billionth dimensional feature space. The kernel trick and the Vapnik-Chervonenkis ("VC") dimension allow the support vector machine to thwart the "curse of dimensionality" limiting other methods and effectively derive generalizable answers from this very high dimensional feature space.

If the training vectors are separated by the optimal hyperplane (or generalized optimal hyperplane), then the expectation value of the probability of committing an error on a test example is bounded by the examples in the training set. This bound depends neither on the dimensionality of the feature space, nor on the norm of the vector of coefficients, nor on the bound of the number of the input vectors. Therefore, if the optimal hyperplane can be constructed from a small number of support vectors relative to the training set size, the generalization ability will be high, even in infinite dimensional space. Support vector machines are disclosed in U.S. Pat. Nos. 6,128,608 and 6,157,921, both of which are assigned to the assignee of the present application and are incorporated herein by reference.

The data generated from genomic and proteomic tests can be analyzed from many different viewpoints. The literature shows simple approaches such as studies of gene clusters discovered by unsupervised learning techniques (Alon, 1999). For example, each experiment may correspond to one patient carrying or not carrying a specific disease (see e.g. (Golub, 1999)). In this case, clustering usually groups patients with similar clinical records. Supervised learning has also been applied to the classification of proteins (Brown, 2000) and to cancer classification (Golub, 1999).

Support vector machines provide a desirable solution for the problem of discovering knowledge from vast amounts of input data. However, the ability of a support vector machine to discover knowledge from a data set is limited in proportion to the information included within the training data set. Accordingly, there exists a need for a system and method for pre-processing data so as to augment the training data to maximize the knowledge discovery by the support vector machine.

Furthermore, the raw output from a support vector machine may not fully disclose the knowledge in the most readily interpretable form. Thus, there further remains a need for a system and method for post-processing data output from a support vector machine in order to maximize the value of the information delivered for human or further automated processing.

In addition, the ability of a support vector machine to discover knowledge from data is limited by the type of kernel selected. Accordingly, there remains a need for an improved system and method for selecting and/or creating an appropriate kernel for a support vector machine.

Further, methods, systems and devices are needed to manipulate the information contained in the databases generated by investigations of proteomics and genomics. Also, methods, systems and devices are needed to integrate information from genomic, proteomic and traditional sources of biological information. Such information is needed for the diagnosis and prognosis of diseases and other changes in biological and other systems.

Furthermore, methods and compositions are needed for treating the diseases and other changes in biological systems that are identified by the support vector machine. Once patterns or the relationships between the data are identified by the support vector machines of the present invention and are used to detect or diagnose a particular disease state, diagnostic tests, including gene chips and tests of bodily fluids or bodily changes, and methods and compositions for treating the condition are needed.

SUMMARY OF THE INVENTION

The present invention comprises systems and methods for enhancing knowledge discovered from data using a learning machine in general and a support vector machine in particular. In particular, the present invention comprises methods of using a learning machine for diagnosing and prognosing changes in biological systems such as diseases. Further, once the knowledge discovered from the data is determined, the specific relationships discovered are used to diagnose and prognose diseases, and methods of detecting and treating such diseases are applied to the biological system. In particular, the invention is directed to detection of genes involved with prostate cancer and determining methods and compositions for treatment of prostate cancer.

One embodiment of the present invention comprises preprocessing a training data set in order to allow the most advantageous application of the learning machine. Each training data point comprises a vector having one or more coordinates. Pre-processing the training data set may comprise identifying missing or erroneous data points and taking appropriate steps to correct the flawed data or as appropriate remove the observation or the entire field from the scope of the problem. Pre-processing the training data set may also comprise adding dimensionality to each training data point by adding one or more new coordinates to the vector. The new coordinates added to the vector may be derived by applying a transformation to one or more of the original coordinates. The transformation may be based on expert knowledge, or may be computationally derived. In a situation where the training data set comprises a continuous variable, the transformation may comprise optimally categorizing the continuous variable of the training data set.

In a preferred embodiment, the support vector machine is trained using the pre-processed training data set. In this manner, the additional representations of the training data provided by the preprocessing may enhance the learning machine's ability to discover knowledge therefrom. In the particular context of support vector machines, the greater the dimensionality of the training set, the higher the quality of the generalizations that may be derived therefrom. When the knowledge to be discovered from the data relates to a regression or density estimation or where the training output comprises a continuous variable, the training output may be post-processed by optimally categorizing the training output to derive categorizations from the continuous variable.

Some of the original coordinates may be noisy or irrelevant to the problem and therefore more harmful than useful. In a preferred embodiment of the invention, the pre-processing also consists of removing coordinates athat are irrelevant to the problem at hand by using a filter technique. Such filter techniques are known to those skilled in the art and may include correlation coefficients and the selection of the first few principal components.

A test data set is pre-processed in the same manner as was the training data set. Then, the trained learning machine is tested using the pre-processed test data set. A test output of the trained learning machine may be post-processing to determine if the test output is an optimal solution. Post-processing the test output may comprise interpreting the test output into a format that may be compared with the test data set. Alternative postprocessing steps may enhance the human interpretability or suitability for additional processing of the output data.

In the context of a support vector machine, the present invention also provides for the selection of at least one kernel prior to training the support vector machine. The selection of a kernel may be based on prior knowledge of the specific problem being addressed or analysis of the properties of any available data to be used with the learning machine and is typically dependant on the nature of the knowledge to be discovered from the data. Optionally, an iterative process comparing postprocessed training outputs or test outputs can be applied to make a determination as to which configuration provides the optimal solution. If the test output is not the optimal solution, the selection of the kernel may be adjusted and the support vector machine may be retrained and retested. When it is determined that the optimal solution has been identified, a live data set may be collected and pre-processed in the same manner as was the training data set. The pre-processed live data set is input into the learning machine for processing. The live output of the learning machine may then be post-processed by interpreting the live output into a computationally derived alphanumeric classifier or other form suitable to further utilization of the SVM derived answer.

In an exemplary embodiment a system is provided enhancing knowledge discovered from data using a support vector machine. The exemplary system comprises a storage device for storing a training data set and a test data set, and a processor for executing a support vector machine. The processor is also operable for collecting the training data set from the database, pre-processing the training data set to enhance each of a plurality of training data points, training the support vector machine using the pre-processed training data set, collecting the test data set from the database, pre-processing the test data set in the same manner as was the training data set, testing the trained support vector machine using the pre-processed test data set, and in response to receiving the test output of the trained support vector machine, post-processing the test output to determine if the test output is an optimal solution. The exemplary system may also comprise a communications device for receiving the test data set and the training data set from a remote source. In such a case, the processor may be operable to store the training data set in the storage device prior pre-processing of the training data set and to store the test data set in the storage device prior pre-processing of the test data set. The exemplary system may also comprise a display device for displaying the post-processed test data. The processor of the exemplary system may further be operable for performing each additional function described above. The communications device may be further operable to send a computationally derived alphanumeric classifier or other SVM-based raw or post-processed output data to a remote source.

In an exemplary embodiment, a system and method are provided for enhancing knowledge discovery from data using multiple learning machines in general and multiple support vector machines in particular. Training data for a learning machine is pre-processed in order to add meaning thereto. Pre-processing data may involve transforming the data points and/or expanding the data points. By adding meaning to the data, the learning machine is provided with a greater amount of information for processing. With regard to support vector machines in particular, the greater the amount of information that is processed, the better generalizations about the data that may be derived. Multiple support vector machines, each comprising distinct kernels, are trained with the pre-processed training data and are tested with test data that is pre-processed in the same manner. The test outputs from multiple support vector machines are compared in order to determine which of the test outputs if any represents an optimal solution. Selection of one or more kernels may be adjusted and one or more support vector machines may be retrained and retested. When it is determined that an optimal solution has been achieved, live data is pre-processed and input into the support vector machine comprising the kernel that produced the optimal solution. The live output from the learning machine may then be post-processed into a computationally derived alphanumeric classifier for interpretation by a human or computer automated process.

A preferred embodiment comprises methods and systems for detecting genes involved with prostate cancer and determination of methods and compositions for treatments of prostate cancer. The present invention, comprising supervised learning techniquest, can use all the arrays currently known. Several single genes separate all 17 BPH vs. 24 G4 without error. Using the methods disclosed herein, one BPH was identified automatically as an outlier. SVMs can reach zero leave-one-out error with at least as few as two genes. In the space of the two genes selected by SVMs, normal samples and dysplasia resemble BPH and G3 constitutes a separate cluster from BPH and G4.

BRIEF DESCRIPTION OF THE DRAWINGS

FIG. 4 illustrates an exemplary unexpanded data set that may be input into a support vector machine.

FIG. 5 illustrates an exemplary expanded data set that may be input into a support vector machine based on the data set of FIG. 4.

FIG. 10*a* shows the oldest descendents of the root labeled by the genes obtained from regular SVM-RFE gene ranking; FIG. 10*b* shows the second level of the tree filled with top ranking genes from root to leaf after the top ranking gene of FIG. 10*a* is removed, and SVM-RFE is run again; FIG. 10*c* shows the second child of the oldest node of the root and its oldest descendents labeled by using constrained RFE; and FIG. 10*d* shows the first and second levels of the tree filled root to leaf and the second child of each root node filled after the top ranking genes in FIG. 10*c* are removed.

FIG. 11*a* shows separation of the training examples with an SVM; FIG. 11*b* shows separation of the training and test examples with the same SVM; FIG. 11*c* shows separation of the training examples with the baseline method; and FIG. 11*d* shows separation of the training and test examples with the baseline method.

FIGS. 13*a* and 13*b* show the raw data; and FIGS. 13*c* and 13*d* are the same data after taking the log.

FIG. 14*a* shows the raw data and FIG. 14*b* shows the inverse error function.

FIG. 23*a* shows SVMs trained on SVM selected genes or on baseline genes and FIG. 23*b* shows a baseline classifier trained on SVM selected genes or on baseline genes.

DETAILED DESCRIPTION

Figure 1:
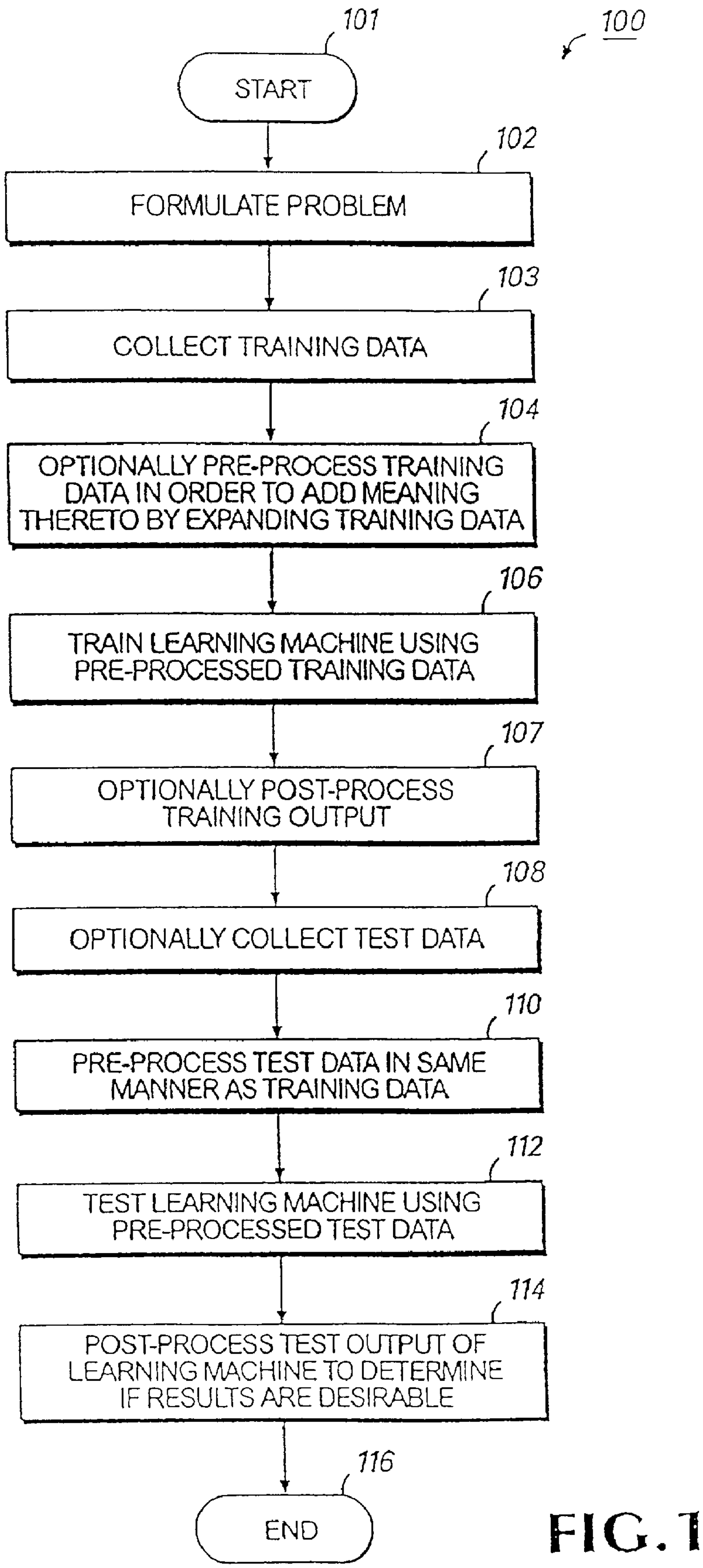
FIG. 1 is a flowchart illustrating an exemplary general method for increasing knowledge that may be discovered from data using a learning machine.

The present invention provides methods, systems and devices for discovering knowledge from data using learning machines. Particularly, the present invention is directed to methods, systems and devices for knowledge discovery from data using learning machines that are provided information regarding changes in biological systems. More particularly, the present invention comprises methods of use of such knowledge for diagnosing and prognosing changes in biological systems such as diseases. Additionally, the present invention comprises methods, compositions and devices for applying such knowledge to the testing and treating of individuals with changes in their individual biological systems. Preferred embodiments comprise detection of genes involved with prostate cancer and use of such information for treatment of patients with prostate cancer.

As used herein, "biological data" means any data derived from measuring biological conditions of human, animals or other biological organisms including microorganisms, viruses, plants and other living organisms. The measurements may be made by any tests, assays or observations that are known to physicians, scientists, diagnosticians, or the like. Biological data may include, but is not limited to, clinical tests and observations, physical and chemical measurements, genomic determinations, proteomic determinations, drug levels, hormonal and immunological tests, neurochemical or neurophysical measurements, mineral and vitamin level determinations, genetic and familial histories, and other determinations that may give insight into the state of the individual or individuals that are undergoing testing. Herein, the use of the term "data" is used interchangeably with "biological data".

While several examples of learning machines exist and advancements are expected in this field, the exemplary embodiments of the present invention focus on the support vector machine. As is known in the art, learning machines comprise algorithms that may be trained to generalize using data with known outcomes. Trained learning machine algorithms may then be applied to cases of unknown outcome for prediction. For example, a learning machine may be trained to recognize patterns in data, estimate regression in data or estimate probability density within data. Learning machines may be trained to solve a wide variety of problems as known to those of ordinary skill in the art. A trained learning machine may optionally be tested using test data to ensure that its output is validated within an acceptable margin of error. Once a learning machine is trained and tested, live data may be input therein. The live output of a learning machine comprises knowledge discovered from all of the training data as applied to the live data.

The present invention comprises methods, systems and devices for analyzing patterns found in biological data, data such as that generated by examination of genes, transcriptional and translational products and proteins. Genomic information can be found in patterns generated by hybridization reactions of genomic fragments and complementary nucleic acids or interacting proteins. One of the most recent tools for investigating such genomic or nucleic acid interactions is the DNA gene chip or microarray. The microarray allows for the processing of thousands of nucleic interactions. DNA microarrays enable researchers to screen thousands of genes in one experiment. For example, the microarray could contain 2400 genes on a small glass slide and can be used to determine the presence of DNA or RNA in the sample. Such microarray tests can be used in basic research and biomedical research including tumor biology, neurosciences, signal transduction, transcription regulation, and cytokine and receptor studies. Additionally, there are applications for pharmaceutical drug discovery, target identification, lead optimization, pharmacokinetics, pharmacogenomics and diagnostics. The market for microarray technology was approximately $98 million in 1999 and the amount of data generated and stored in databases developed from multiple microarray tests is enormous. The present invention provides for methods, systems and devices that can use the data generated in such microarray and nucleic acid chip tests for the diagnosis and prognosis of diseases and for the development of therapeutic agents to treat such diseases.

The present invention also comprises devices comprising microarrays with specific sequence identifying probes that can be used to diagnose or prognose the status of or a specific change in the biological system. Once the learning machine of the present invention has identified specific relationships among the data that are capable of diagnosing or prognosing the current status or a change in a biological system, specific devices then incorporate tests for those specific relationships. For example, the learning machine of the present invention identifies specific genes that are related to the presence or future occurrence of a change in a biological system, such as the presence or appearance of a tumor. Knowing the sequence of these genes allows for the making of a specific treating device for those identified genes. For example, a support device, such as a chip, comprising DNA, RNA or specific binding proteins, or any such combination, that specifically binds to specifically identified genes is used to easily identify individuals having a particular tumor or the likelihood of developing the tumor. Additionally, specific proteins, either those identified by the learning machine or those that are associated with the genes identified by the learning machine, can be determined, for example by using serological tests directed to specifically detecting the identified proteins, gene products or unsing antibodies or antibody fragments directed to the proteins or gene products. Such tests include, but are not limited to, antibody microarrays on chips, Western blotting tests, ELISA, and other tests known in the art wherein binding between specific binding partners is used for detection of one of the partners.

Furthermore, the present invention comprises methods and compositions for treating the conditions currently existing in a biological organism or conditions resulting from changes in biological systems or for treating the biological system to alter the biological system to prevent or enhance specific conditions. For example, if the diagnosis of an individual includes the detection of a tumor, the individual can be treated with anti-tumor medications such as chemotherapeutic compositions. If the diagnosis of an individual includes the predisposition or prognosis of tumor development, the individual may be treated prophalactically with chemotherapeutic compositions to prevent the occurrence of the tumor. If specific genes are identified with the occurrence of tumors, the individual may be treated with specific antisense or other gene therapy methods to suppress the expression of such genes. Additionally, if specific genes or gene products are identified with the occurrence of tumors, then specific compositions that inhibit or functionally effect the genes or gene products are administered to the individual. The instances described herein are merely exemplary and are not to be construed as limiting the scope of the invention.

Proteomic investigations provide for methods of determining the proteins involved in normal and pathological states. Current methods of determining the proteome of a person or a population at any particular time or stage comprise the use of gel electrophoresis to separate the proteins in a sample. Preferably, 2-D gel electrophoresis is used to separate the proteins more completely. Additionally, the sample may be preprocessed to remove known proteins. The proteins may be labeled, for example, with fluorescent dyes, to aid in the determination of the patterns generated by the selected proteome. Patterns of separated proteins can be analyzed using the learning machines of the present invention. Capturing the gel image can be accomplished by image technology methods known in the art such as densitometry, CCD camera and laser scanning and storage phosphor instruments. Analysis of the gels reveals patterns in the proteome that are important in diagnosis and prognosis of pathological states and shows changes in relation to therapeutic interventions.

Further steps of investigating proteomes involve isolation of proteins at specific sites in the gels. Robotic systems for isolating specific sites are currently available. Isolation is followed by determination of the sequence and thus, the identity of the proteins. Studying the proteome of individuals or a population involves the generation, capture, analysis and integration of an enormous amount of data. Automation is currently being used to help manage the physical manipulations needed for the data generation. The learning machines of the present invention are used to analyze the biological data generated and to provide the information desired.

Additionally, using modifications of detection devices, such as chip detection devices, large libraries of biological data can be generated. Methods for generating libraries include technologies that use proteins covalently linked to their mRNA to determine the proteins made, for example, as rarely translated proteins. Such a technology comprises translating mRNA in vitro and covalently attaching the translated protein to the mRNA. The sequence of the mRNA and thus the protein is then determined using amplification methods such as PCR. Libraries containing $10^{14}$ to $10^{15}$ members can be established from this data. These libraries can be used to determine peptides that bind receptors or antibody libraries can be developed that contain antibodies that avidly bind their targets.

Libraries called protein domain libraries can be created from cellular mRNA where the entire proteins are not translated, but fragments are sequenced. These libraries can be used to determine protein function.

Other methods of investigating the proteome do not use gel electrophoresis. For example, mass spectrophotometry can be used to catalog changes in protein profiles and to define nucleic acid expression in normal or diseased tissues or in infectious agents to identify and validate drug and diagnostic targets. Analysis of this data is accomplished by the methods, systems and devices of the present invention. Further, technologies such as 2-hybrid and 2+1 hybrid systems that use proteins to capture the proteins with which they interact, currently found in yeast and bacterial systems, generate genome-wide protein interaction maps (PIMs). Large libraries of information such as PIMs can be manipulated by the present invention.

Antibody chips have been developed that can be used to separate or identify specific proteins or types of proteins. Additionally, phage antibody libaries can be used to determine protein function. Genomic libraries can be searched for open reading frames (ORFS) or ESTs (expressed sequence tags) of interest and from the sequence, peptides are synthesized. Peptides for different genes are placed in 96 well trays for selection of antibodies from phage libraries. The antibodies are then used to locate the protein relating to the original ORFs or ESTs in sections of normal and diseased tissue.

The present invention can be used to analyze biological data generated at multiple stages of investigation into biological functions, and further, to integrate the different kinds of data for novel diagnostic and prognostic determinations. For example, biological data obtained from clinical case information, such as diagnostic test data, family or genetic histories, prior or current medical treatments, and the clinical outcomes of such activities, can be utilized in the methods, systems and devices of the present invention. Additionally, clinical samples such as diseased tissues or fluids, and normal tissues and fluids, and cell separations can provide biological data that can be utilized by the current invention. Proteomic determinations such as 2-D gel, mass spectrophotometry and antibody screening can be used to establish databases that can be utilized by the present invention. Genomic databases can also be used alone or in combination with the above-described data and databases by the present invention to provide comprehensive diagnosis, prognosis or predictive capabilities to the user of the present invention.

A first aspect of the present invention facilitates analysis of biological data by optionally pre-processing the data prior to using the data to train a learning machine and/or optionally post-processing the output from a learning machine. Generally stated, pre-processing data comprises reformatting or augmenting the data in order to allow the learning machine to be applied most advantageously. In a manner similar to pre-processing, post-processing involves interpreting the output of a learning machine in order to discover meaningful characteristics thereof. The meaningful characteristics to be ascertained from the output may be problem- or data-specific. Post-processing involves interpreting the output into a form that, for example, may be understood by or is otherwise useful to a human observer, or converting the output into a form which may be readily received by another device for, e.g., archival or transmission.

FIG. 1 is a flowchart illustrating a general method 100 for analyzing data using learning machines. The method 100 begins at starting block 101 and progresses to step 102 where a specific problem is formalized for application of analysis through machine learning. Particularly important is a proper formulation of the desired output of the learning machine. For instance, in predicting future performance of an individual equity instrument, or a market index, a learning machine is likely to achieve better performance when predicting the expected future change rather than predicting the future price level. The future price expectation can later be derived in a post-processing step as will be discussed later in this specification.

After problem formalization, step 103 addresses training data collection. Training data comprises a set of data points having known characteristics. Training data may be collected from one or more local and/or remote sources. The collection of training data may be accomplished manually or by way of an automated process, such as known electronic data transfer methods. Accordingly, an exemplary embodiment of the learning machine for use in conjunction with the present invention may be implemented in a networked computer environment. Exemplary operating environments for implementing various embodiments of the learning machine will be described in detail with respect to FIGS. 7–8.

At step 104, the collected training data is optionally pre-processed in order to allow the learning machine to be applied most advantageously toward extraction of the knowledge inherent to the training data. During this preprocessing stage the training data can optionally be expanded through transformations, combinations or manipulation of individual or multiple measures within the records of the training data. As used herein, "expanding data" is meant to refer to altering the dimensionality of the input data by changing the number of observations available to determine each input point (alternatively, this could be described as adding or deleting columns within a database table). By way of illustration, a data point may comprise the coordinates (1,4,9). An expanded version of this data point may result in the coordinates (1,1,4,2,9,3). In this example, it may be seen that the coordinates added to the expanded data point are based on a square-root transformation of the original coordinates. By adding dimensionality to the data point, this expanded data point provides a varied representation of the input data that is potentially more meaningful for analysis by a learning machine. Data expansion in this sense affords opportunities for learning machines to analyze data not readily apparent in the unexpanded training data.

Expanding data may comprise applying any type of meaningful transformation to the data and adding those transformations to the original data. The criteria for determining whether a transformation is meaningful may depend on the input data itself and/or the type of knowledge that is sought from the data. Illustrative types of data transformations include: addition of expert information; labeling; binary conversion, e.g., a bit map; transformations, such as Fourier, wavelet, Radon, principal component analysis and kernel principal component analysis, as well as clustering; scaling; normalizing; probabilistic and statistical analysis; significance testing; strength testing; searching for two-dimensional regularities; Hidden Markov Modeling; identification of equivalence relations; application of contingency tables; application of graph theory principles; creation of vector maps; addition, subtraction, multiplication, division, application of polynomial equations and other algebraic transformations; identification of proportionality; determination of discriminatory power; etc. In the context of medical data, potentially meaningful transformations include: association with known standard medical reference ranges; physiologic truncation; physiologic combinations; biochemical combinations; application of heuristic rules; diagnostic criteria determinations; clinical weighting systems; diagnostic transformations; clinical transformations; application of expert knowledge; labeling techniques; application of other domain knowledge; Bayesian network knowledge; etc. These and other transformations, as well as combinations thereof, will occur to those of ordinary skill in the art.

Those skilled in the art should also recognize that data transformations may be performed without adding dimensionality to the data points. For example a data point may comprise the coordinate (A, B, C). A transformed version of this data point may result in the coordinates (1, 2, 3), where the coordinate "1" has some known relationship with the coordinate "A," the coordinate "2" has some known relationship with the coordinate "B," and the coordinate "3" has some known relationship with the coordinate "C." A transformation from letters to numbers may be required, for example, if letters are not understood by a learning machine. Other types of transformations are possible without adding dimensionality to the data points, even with respect to data that is originally in numeric form. Furthermore, it should be appreciated that pre-processing data to add meaning thereto may involve analyzing incomplete, corrupted or otherwise "dirty" data. A learning machine cannot process "dirty" data in a meaningful manner. Thus, a pre-processing step may involve cleaning up or filtering a data set in order to remove, repair or replace dirty data points.

Returning to FIG. 1, an exemplary method 100 continues at step 106, where the learning machine is trained using the pre-processed data. As is known in the art, a learning machine is trained by adjusting its operating parameters until a desirable training output is achieved. The determination of whether a training output is desirable may be accomplished either manually or automatically by comparing the training output to the known characteristics of the training data. A learning machine is considered to be trained when its training output is within a predetermined error threshold from the known characteristics of the training data. In certain situations, it may be desirable, if not necessary, to post-process the training output of the learning machine at step 107. As mentioned, post-processing the output of a learning machine involves interpreting the output into a meaningful form. In the context of a regression problem, for example, it may be necessary to determine range categorizations for the output of a learning machine in order to determine if the input data points were correctly categorized. In the example of a pattern recognition problem, it is often not necessary to post-process the training output of a learning machine.

At step 108, test data is optionally collected in preparation for testing the trained learning machine. Test data may be collected from one or more local and/or remote sources. In practice, test data and training data may be collected from the same source(s) at the same time. Thus, test data and training data sets can be divided out of a common data set and stored in a local storage medium for use as different input data sets for a learning machine. Regardless of how the test data is collected, any test data used must be pre-processed at step 110 in the same manner as was the training data. As should be apparent to those skilled in the art, a proper test of the learning may only be accomplished by using testing data of the same format as the training data. Then, at step 112 the learning machine is tested using the pre-processed test data, if any. The test output of the learning machine is optionally post-processed at step 114 in order to determine if the results are desirable. Again, the post processing step involves interpreting the test output into a meaningful form. The meaningful form may be one that is readily understood by a human or one that is compatible with another processor. Regardless, the test output must be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations. The method 100 ends at step 116.

Figure 2:
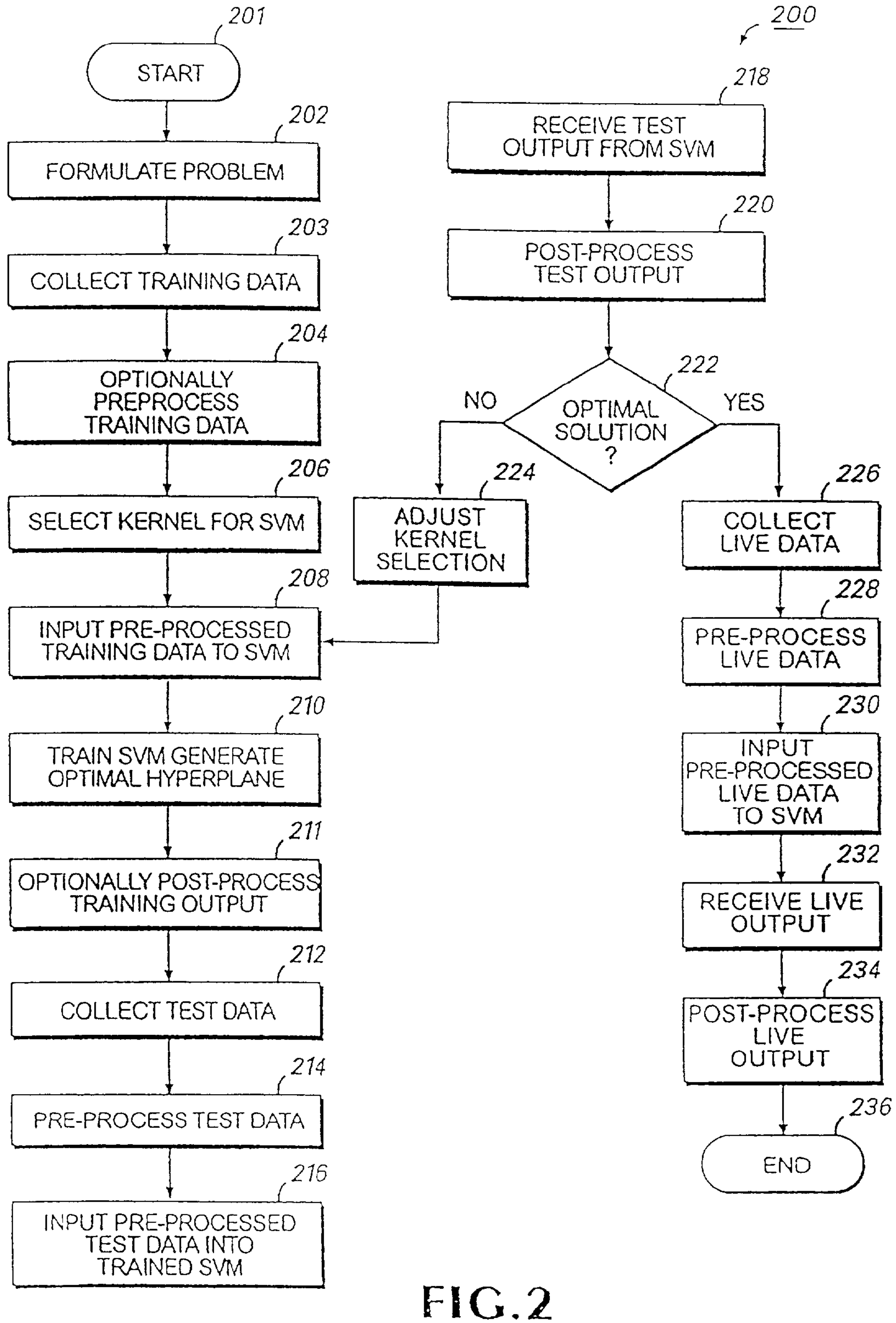
FIG. 2 is a flowchart illustrating an exemplary method for increasing knowledge that may be discovered from data using a support vector machine.

FIG. 2 is a flow chart illustrating an exemplary method 200 for enhancing knowledge that may be discovered from data using a specific type of learning machine known as a support vector machine (SVM). A SVM implements a specialized algorithm for providing generalization when estimating a multi-dimensional function from a limited collection of data. A SVM may be particularly useful in solving dependency estimation problems. More specifically, a SVM may be used accurately in estimating indicator functions (e.g. pattern recognition problems) and real-valued functions (e.g. function approximation problems, regression estimation problems, density estimation problems, and solving inverse problems). The SVM was originally developed by Boser, Guyon and Vapnik ("A training algorithm for optimal margin classifiers", *Fifth Annual Workshop on Computational Learning Theory*, Pittsburgh, ACM (1992) pp. 142–152). The concepts underlying the SVM are also explained in detail in Vapnik's book, entitled *Statistical Learning Theory* (John Wiley & Sons, Inc. 1998), which is herein incorporated by reference in its entirety. Accordingly, a familiarity with SVMs and the terminology used therewith are presumed throughout this specification.

The exemplary method 200 begins at starting block 201 and advances to step 202, where a problem is formulated and then to step 203, where a training data set is collected. As was described with reference to FIG. 1, training data may be collected from one or more local and/or remote sources, through a manual or automated process. At step 204 the training data is optionally pre-processed. Again, pre-processing data comprises enhancing meaning within the training data by cleaning the data, transforming the data and/or expanding the data. Those skilled in the art should appreciate that SVMs are capable of processing input data having extremely large dimensionality. In fact, the larger the dimensionality of the input data, the better the generalizations a SVM is able to calculate. Therefore, while training data transformations are possible that do not expand the training data, in the specific context of SVMs it is preferable that training data be expanded by adding meaningful information thereto.

At step 206, a kernel is selected for the SVM. As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge. As is known in the art, exemplary kernels include polynomial kernels, radial basis classifier kernels, linear kernels, etc. In an alternate embodiment, a customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel.

At step 206, a kernel is selected for the SVM. As is known in the art, different kernels will cause an SVM to produce varying degrees of quality in the output for a given set of input data. Therefore, the selection of an appropriate kernel may be essential to the desired quality of the output of the SVM. A kernel may be chosen based on prior performance knowledge. As is known in the art, exemplary kernels include polynomial kernels, radial basis function kernels, linear kernels, etc. A customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel.

Next, at step 208, the pre-processed training data is input into the SVM. At step 210, the SVM is trained using the pre-processed training data to generate an optimal hyperplane. Optionally, the training output of the SVM may then be post-processed at step 211. Again, post-processing of training output may be desirable, or even necessary, at this point in order to properly calculate ranges or categories for the output. At step 212 test data is collected similarly to previous descriptions of data collection. The test data is pre-processed at step 214 in the same manner as was the training data above. Then, at step 216 the pre-processed test data is input into the SVM for processing in order to determine whether the SVM was trained in a desirable manner. The test output is received from the SVM at step 218 and is optionally post-processed at step 220.

Based on the post-processed test output, it is determined at step 222 whether an optimal minimum was achieved by the SVM. Those skilled in the art should appreciate that a SVM is operable to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM. Accordingly, at step 222, determining whether the optimal minimum has been ascertained may involve comparing the output of a SVM with a historical or predetermined value. Such a predetermined value may be dependant on the test data set. For example, in the context of a pattern recognition problem where data points are classified by a SVM as either having a certain characteristic or not having the characteristic, a global minimum error of 50% would not be optimal. In this example, a global minimum of 50% is no better than the result that would be achieved by flipping a coin to determine whether the data point had that characteristic. As another example, in the case where multiple SVMs are trained and tested simultaneously with varying kernels, the outputs for each SVM may be compared with output of other SVM to determine the practical optimal solution for that particular set of kernels. The determination of whether an optimal solution has been ascertained may be performed manually or through an automated comparison process.

If it is determined that the optimal minimum has not been achieved by the trained SVM, the method advances to step 224, where the kernel selection is adjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method 200 is repeated from step 208, where the pre-processed training data is input into the SVM for training purposes. When it is determined at step 222 that the optimal minimum has been achieved, the method advances to step 226, where live data is collected similarly as described above. By definition, live data has not been previously evaluated, so that the desired output characteristics that were known with respect to the training data and the test data are not known.

At step 228 the live data is pre-processed in the same manner as was the training data and the test data. At step 230, the live pre-processed data is input into the SVM for processing. The live output of the SVM is received at step 232 and is post-processed at step 234. In one embodiment of the learning machine, post-processing comprises converting the output of the SVM into a computationally-derived alpha-numerical classifier for interpretation by a human or computer. Preferably, the alphanumerical classifier comprises a single value that is easily comprehended by the human or computer. The method 200 ends at step 236.

Figure 3:
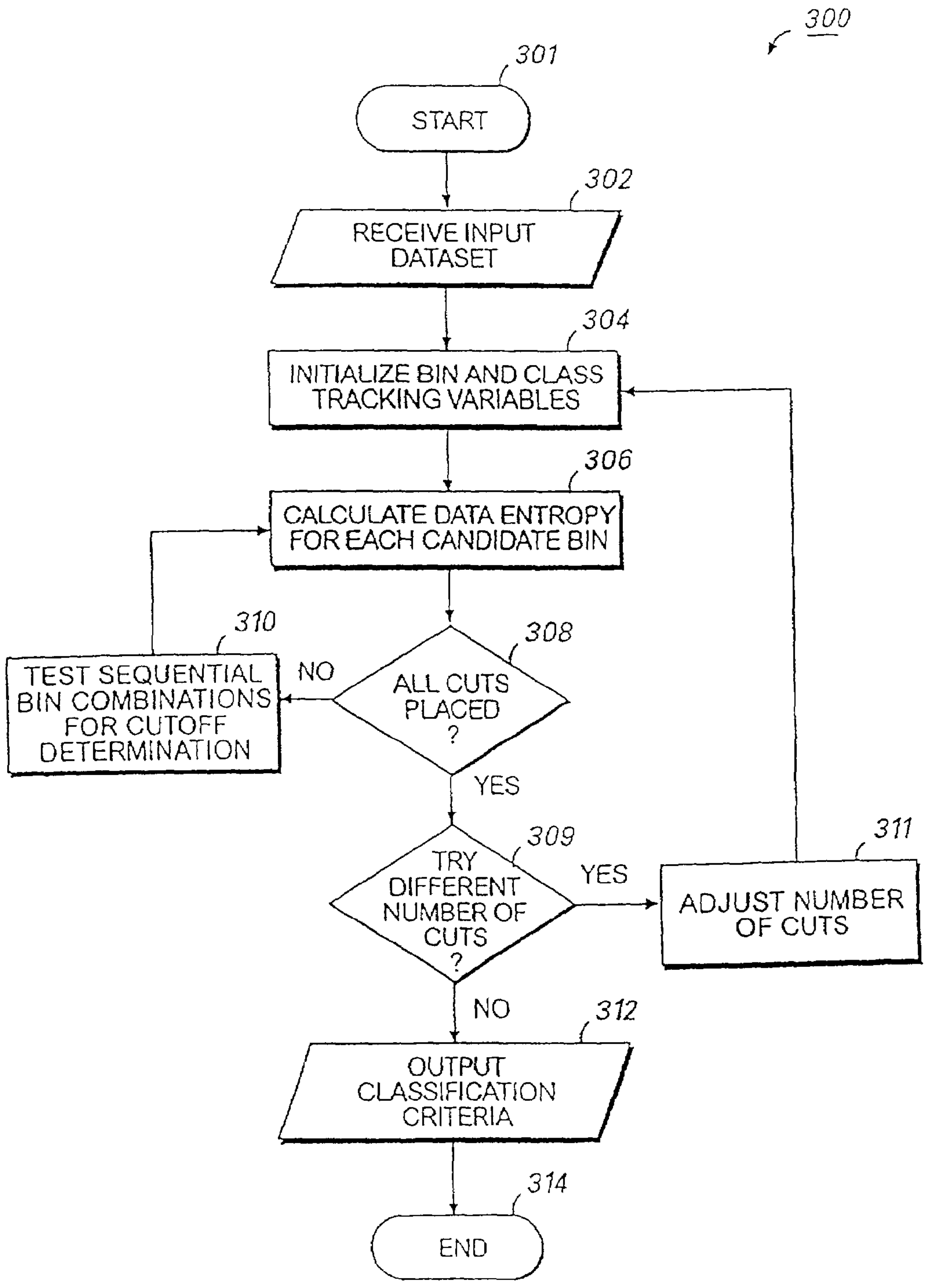
FIG. 3 is a flowchart illustrating an exemplary optimal categorization method that may be used in a stand-alone configuration or in conjunction with a learning machine for pre-processing or post-processing techniques in accordance with an exemplary embodiment of the present invention.

FIG. 3 is a flow chart illustrating an exemplary optimal categorization method 300 that may be used for pre-processing data or post-processing output from a learning machine. Additionally, as will be described below, the exemplary optimal categorization method may be used as a stand-alone categorization technique, independent from learning machines. The exemplary optimal categorization method 300 begins at starting block 301 and progresses to step 302, where an input data set is received. The input data set comprises a sequence of data samples from a continuous variable. The data samples fall within two or more classification categories. Next, at step 304 the bin and class-tracking variables are initialized. As is known in the art, bin variables relate to resolution, while class-tracking variables relate to the number of classifications within the data set. Determining the values for initialization of the bin and class-tracking variables may be performed manually or through an automated process, such as a computer program for analyzing the input data set. At step 306, the data entropy for each bin is calculated. Entropy is a mathematical quantity that measures the uncertainty of a random distribution. In the exemplary method 300, entropy is used to gauge the gradations of the input variable so that maximum classification capability is achieved.

The method 300 produces a series of "cuts" on the continuous variable, such that the continuous variable may be divided into discrete categories. The cuts selected by the exemplary method 300 are optimal in the sense that the average entropy of each resulting discrete category is minimized. At step 308, a determination is made as to whether all cuts have been placed within input data set comprising the continuous variable. If all cuts have not been placed, sequential bin combinations are tested for cutoff determination at step 310. From step 310, the exemplary method 300 loops back through step 306 and returns to step 308 where it is again determined whether all cuts have been placed within input data set comprising the continuous variable. When all cuts have been placed, the entropy for the entire system is evaluated at step 309 and compared to previous results from testing more or fewer cuts. If it cannot be concluded that a minimum entropy state has been determined, then other possible cut selections must be evaluated and the method proceeds to step 311. From step 311 a heretofore untested selection for number of cuts is chosen and the above process is repeated from step 304. When either the limits of the resolution determined by the bin width has been tested or the convergence to a minimum solution has been identified, the optimal classification criteria is output at step 312 and the exemplary optimal categorization method 300 ends at step 314.

The optimal categorization method 300 takes advantage of dynamic programming techniques. As is known in the art, dynamic programming techniques may be used to significantly improve the efficiency of solving certain complex problems through carefully structuring an algorithm to reduce redundant calculations. In the optimal categorization problem, the straightforward approach of exhaustively searching through all possible cuts in the continuous variable data would result in an algorithm of exponential complexity and would render the problem intractable for even moderate sized inputs. By taking advantage of the additive property of the target function, in this problem the average entropy, the problem may be divided into a series of sub-problems. By properly formulating algorithmic sub-structures for solving each sub-problem and storing the solutions of the sub-problems, a significant amount of redundant computation may be identified and avoided. As a result of using the dynamic programming approach, the exemplary optimal categorization method 300 may be implemented as an algorithm having a polynomial complexity, which may be used to solve large sized problems.

As mentioned above, the exemplary optimal categorization method 300 may be used in pre-processing data and/or post-processing the output of a learning machine. For example, as a pre-processing transformation step, the exemplary optimal categorization method 300 may be used to extract classification information from raw data. As a post-processing technique, the exemplary optimal range categorization method may be used to determine the optimal cut-off values for markers objectively based on data, rather than relying on ad hoc approaches. As should be apparent, the exemplary optimal categorization method 300 has applications in pattern recognition, classification, regression problems, etc. The exemplary optimal categorization method 300 may also be used as a stand-alone categorization technique, independent from SVMs and other learning machines.

FIG. 4 illustrates an exemplary unexpanded data set 400 that may be used as input for a support vector machine. This data set 400 is referred to as "unexpanded" because no additional information has been added thereto. As shown, the unexpanded data set comprises a training data set 402 and a test data set 404. Both the unexpanded training data set 402 and the unexpanded test data set 404 comprise data points, such as exemplary data point 406, relating to historical clinical data from sampled medical patients. In this example, the data set 400 may be used to train a SVM to determine whether a breast cancer patient will experience a recurrence or not.

Each data point includes five input coordinates, or dimensions, and an output classification shown as 406*a–f* which represent medical data collected for each patient. In particular, the first coordinate 406*a* represents "Age," the second coordinate 406*b* represents "Estrogen Receptor Level," the third coordinate 406*c* represents "Progesterone Receptor Level," the fourth coordinate 406*d* represents "Total Lymph Nodes Extracted," the fifth coordinate 406*e* represents "Positive (Cancerous) Lymph Nodes Extracted," and the output classification 406*f*, represents the "Recurrence Classification." The important known characteristic of the data 400 is the output classification 406*f* (Recurrence Classification), which, in this example, indicates whether the sampled medical patient responded to treatment favorably without recurrence of cancer ("−1") or responded to treatment negatively with recurrence of cancer ("1"). This known characteristic will be used for learning while processing the training data in the SVM will be used in an evaluative fashion after the test data is input into the SVM thus creating a "blind" test, and will obviously be unknown in the live data of current medical patients.

Table 1 provides an exemplary test output from a SVM trained with the unexpanded training data set 402 and tested with the unexpanded data set 404 shown in FIG. 4.

TABLE 1

| Vapnik's Polynomial |
|---|
| Alphas bounded up to 1000 |
| Input values will be individually scaled to lie between 0 and 1 |

TABLE 1-continued

| Vapnik's Polynomial | |
|---|---|
| SV zero threshold: 1e−16 | |
| Margin threshold: 0.1 | |
| Objective zero tolerance: 1e−17 | |
| Degree of polynomial: 2 | |
| Test set: | |
| Total samples: | 24 |
| Positive samples: | 8 |
| False negatives: | 4 |
| Negative samples: | 16 |
| False positives: | 6 |

The test output has been post-processed to be comprehensible by a human or computer. According to the table, the test output shows that 24 total samples (data points) were examined by the SVM and that the SVM incorrectly identified four of eight positive samples (50%), i.e., found negative for a positive sample, and incorrectly identified 6 of sixteen negative samples (37.5%), i.e., found positive for a negative sample.

FIG. 5 illustrates an exemplary expanded data set 600 that may be used as input for a support vector machine. This data set 600 is referred to as "expanded" because additional information has been added thereto. Note that aside from the added information, the expanded data set 600 is identical to the unexpanded data set 400 shown in FIG. 4. The additional information supplied to the expanded data set has been supplied using the exemplary optimal range categorization method 300 described with reference to FIG. 3. As shown, the expanded data set comprises a training data set 602 and a test data set 604. Both the expanded training data set 602 and the expanded test data set 604 comprise data points, such as exemplary data point 606, relating to historical data from sampled medical patients. Again, the data set 600 may be used to train a SVM to learn whether a breast cancer patient will experience a recurrence of the disease.

Through application of the exemplary optimal categorization method 300, each expanded data point includes twenty coordinates (or dimensions) **606*a*1–3 through 606*e*1–3, and an output classification 606*f*, which collectively represent medical data and categorization transformations thereof for each patient. In particular, the first coordinate 606*a* represents "Age," the second coordinate through the fourth coordinate 606*a*1–606*a*3 are variables that combine to represent a category of age. For example, a range of ages may be categorized, for example, into "young" "middle-aged" and "old" categories respective to the range of ages present in the data. As shown, a string of variables "0" (606*a*1), "0" (606*a*2), "1" (606*a*3) may be used to indicate that a certain age value is categorized as "old." Similarly, a string of variables "0" (606*a*1), "1" (606*a*2), "0" (606*a*3) may be used to indicate that a certain age value is categorized as "middle-aged." Also, a string of variables "1" (606*a*1), "0" (606*a*2), "0" (606*a*1) may be used to indicate that a certain age value is categorized as "young." From an inspection of FIG. 6, it may be seen that the optimal categorization of the range of "Age" 606*a* values, using the exemplary method 300, was determined to be 31–33="young," 34="middle-aged" and 35–49="old." The other coordinates, namely coordinate 606*b* "Estrogen Receptors Level," coordinate 606*c* "Progesterone Receptor Level," coordinate 606*d* "Total Lymph Nodes Extracted," and coordinate 606*e*** "Positive (Cancerous) Lymph Nodes Extracted," have each been optimally categorized in a similar manner.

Figure 6:
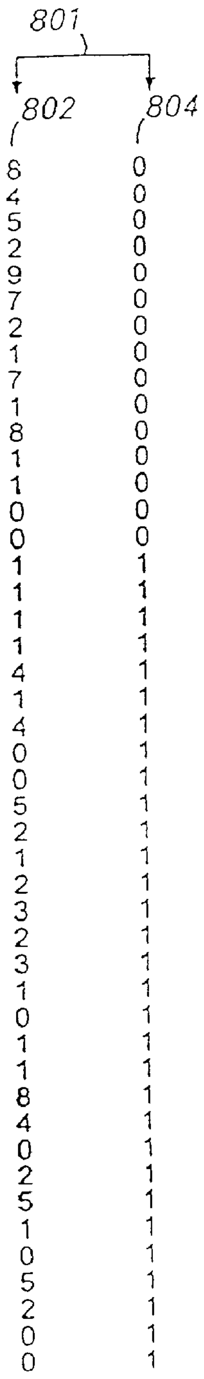
FIG. 6 illustrates an exemplary data set for a stand alone application of the optimal categorization method of FIG. 3.

Table 2 provides an exemplary expanded test output from a SVM trained with the expanded training data set 602 and tested with the expanded data set 604 shown in FIG. 6.

TABLE 2

| Vapnik's Polynomial | |
|---|---|
| Alphas bounded up to 1000 | |
| Input values will be individually scaled to lie between 0 and 1 | |
| SV zero threshold: 1e−16 | |
| Margin threshold: 0.1 | |
| Objective zero tolerance: 1e−17 | |
| Degree of polynomial: 2 | |
| Test set: | |
| Total samples: | 24 |
| Positive samples: | 8 |
| False negatives: | 4 |
| Negative samples: | 16 |
| False positives: | 4 |

The expanded test output has been post-processed to be comprehensible by a human or computer. As indicated, the expanded test output shows that 24 total samples (data points) were examined by the SVM and that the SVM incorrectly identified four of eight positive samples (50%) and incorrectly identified four of sixteen negative samples (25%). Accordingly, by comparing this expanded test output with the unexpanded test output of Table 1, it may be seen that the expansion of the data points leads to improved results (i.e. a lower global minimum error), specifically a reduced instance of patients who would unnecessarily be subjected to follow-up cancer treatments.

FIG. 6 illustrates an exemplary input and output for a stand alone application of the optimal categorization method 300 described in FIG. 3. In the example of FIG. 6, the input data set 801 comprises a "Number of Positive Lymph Nodes" 802 and a corresponding "Recurrence Classification" 804. In this example, the optimal categorization method 300 has been applied to the input data set 801 in order to locate the optimal cutoff point for determination of treatment for cancer recurrence, based solely upon the number of positive lymph nodes collected in a post-surgical tissue sample. The well-known clinical standard is to prescribe treatment for any patient with at least three positive nodes. However, the optimal categorization method 300 demonstrates that the optimal cutoff, seen in Table 3, based upon the input data 801, should be at the higher value of 5.5 lymph nodes, which corresponds to a clinical rule prescribing follow-up treatments in patients with at least six positive lymph nodes.

TABLE 3

| | |
|---|---|
| Number of subintervals: | 2 |
| Number of classes: | 2 |
| Number of data points: | 46 |
| Lower bound: | −1 |
| Upper bound: | 10 |
| Number of bins: | 22 |
| Regularization constant: | 1 |
| Data file: | posnodes.prn |
| Min. Entropy - | 0.568342 |
| Optimal cut-off: | 5.500000 |

As shown in Table 4 below, the prior art accepted clinical cutoff point (≧3.0) resulted in 47% correctly classified recurrences and 71% correctly classified non-recurrences.

TABLE 4

| Cut Point | Correctly Classified Recurrence | Correctly Classified Non-Recurrence |
|---|---|---|
| Clinical (≧3.0) | 7 of 15 (47%) | 22 of 31 (71%) |
| Optimal (≧5.5)) | 5 of 15 (33%) | 30 of 31 (97%) |

Accordingly, 53% of the recurrences were incorrectly classified (further treatment was improperly not recommended) and 29% of the non-recurrences were incorrectly classified (further treatment was incorrectly recommended). By contrast, the cutoff point determined by the optimal categorization method 300 (≧5.5) resulted in 33% correctly classified recurrences and 97% correctly classified non-recurrences. Accordingly, 67% of the recurrences were incorrectly classified (further treatment was improperly not recommended) and 3% of the non-recurrences were incorrectly classified (further treatment was incorrectly recommended).

As shown by this example, it may be feasible to attain a higher instance of correctly identifying those patients who can avoid the post-surgical cancer treatment regimes, using the exemplary optimal categorization method 300. Even though the cutoff point determined by the optimal categorization method 300 yielded a moderately higher percentage of incorrectly classified recurrences, it yielded a significantly lower percentage of incorrectly classified non-recurrences. Thus, considering the trade-off, and realizing that the goal of the optimization problem was the avoidance of unnecessary treatment, the results of the cutoff point determined by the optimal categorization method 300 are mathematically superior to those of the prior art clinical cutoff point. This type of information is potentially extremely useful in providing additional insight to patients weighing the choice between undergoing treatments such as chemotherapy or risking a recurrence of breast cancer.

Table 5 is a comparison of exemplary post-processed output from a first support vector machine comprising a linear kernel and a second support vector machine comprising a polynomial kernel.

TABLE 5

| I. Simple Dot Product | | II. Vapnik's Polynomial | |
|---|---|---|---|
| Alphas bounded up to 1000. | | Alphas bounded up to 1000. | |
| Input values will not be scaled. | | Input values will not be scaled. | |
| SV zero threshold: 1e−16 | | SV zero threshold: 1e−16 | |
| Margin threshold: 0.1 | | Margin threshold: 0.1 | |
| Objective zero tolerance: 1e−07 | | Objective zero tolerance: 1e−07 | |
| | | Degree of polynomial: 2 | |
| Test set: | | Test set: | |
| Total samples: | 24 | Total samples: | 24 |
| Positive samples: | 8 | Positive samples: | 8 |
| False negatives: | 6 | False negatives: | 2 |
| Negative samples: | 16 | Negative samples: | 16 |
| False positives: | 3 | False positives: | 4 |

Table 5 demonstrates that a variation in the selection of a kernel may affect the level of quality of the output of a SVM. As shown, the post-processed output of a first SVM (Column I) comprising a linear dot product kernel indicates that for a given test set of twenty four samples, six of eight positive samples were incorrectly identified and three of sixteen negative samples were incorrectly identified. By way of comparison, the post-processed output for a second SVM (Column II) comprising a polynomial kernel indicates that for the same test set, only two of eight positive samples were incorrectly identified and four of sixteen negative samples were identified. By way of comparison, the polynomial kernel yielded significantly improved results pertaining to the identification of positive samples and yielded only slightly worse results pertaining to the identification of negative samples. Thus, as will be apparent to those of skill in the art, the global minimum error for the polynomial kernel is lower than the global minimum error for the linear kernel for this data set.

Figure 7:
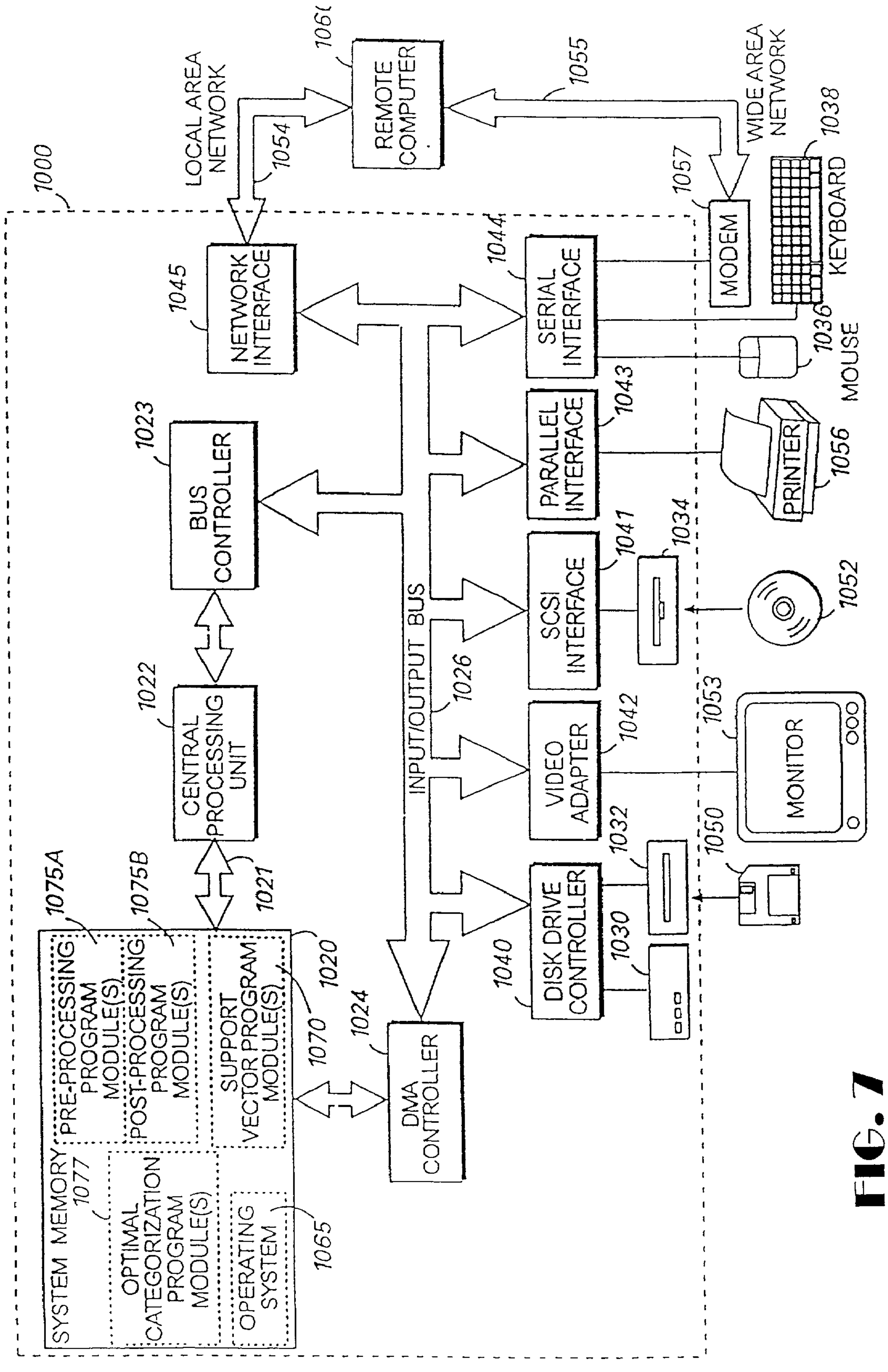
FIG. 7 is a functional block diagram illustrating an exemplary operating environment for an embodiment of the present invention.

FIG. 7 and the following discussion are intended to provide a brief and general description of a suitable computing environment for implementing biological data analysis according to the present invention. Although the system shown in FIG. 7 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described with reference to FIGS. 1 and 2. Furthermore, optimal categorization program modules 1077 may comprise computer-executable instructions for optimally categorizing a data set according to the exemplary methods described with reference to FIG. 3.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 8 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

In another embodiment, a plurality of SVMs can be configured to hierarchically process multiple data sets in parallel or sequentially. In particular, one or more first-level SVMs may be trained and tested to process a first type of data and one or more first-level SVMs can be trained and tested to process a second type of data. Additional types of data may be processed by other first-level SVMs. The output from some or all of the first-level SVMs may be combined in a logical manner to produce an input data set for one or more second-level SVMs. In a similar fashion, output from a plurality of second-level SVMs may be combined in a logical manner to produce input data for one or more third-level SVM. The hierarchy of SVMs may be expanded to any number of levels as may be appropriate. In this manner, lower hierarchical level SVMs may be used to pre-process data that is to be input into higher level SVMs. Also, higher hierarchical level SVMs may be used to post-process data that is output from lower hierarchical level SVMs.

Each SVM in the hierarchy or each hierarchical level of SVMs may be configured with a distinct kernel. For example, SVMs used to process a first type of data may be configured with a first type of kernel while SVMs used to process a second type of data may utilize a second, different type of kernel. In addition, multiple SVMs in the same or different hierarchical level may be configured to process the same type of data using distinct kernels.

Figure 8:
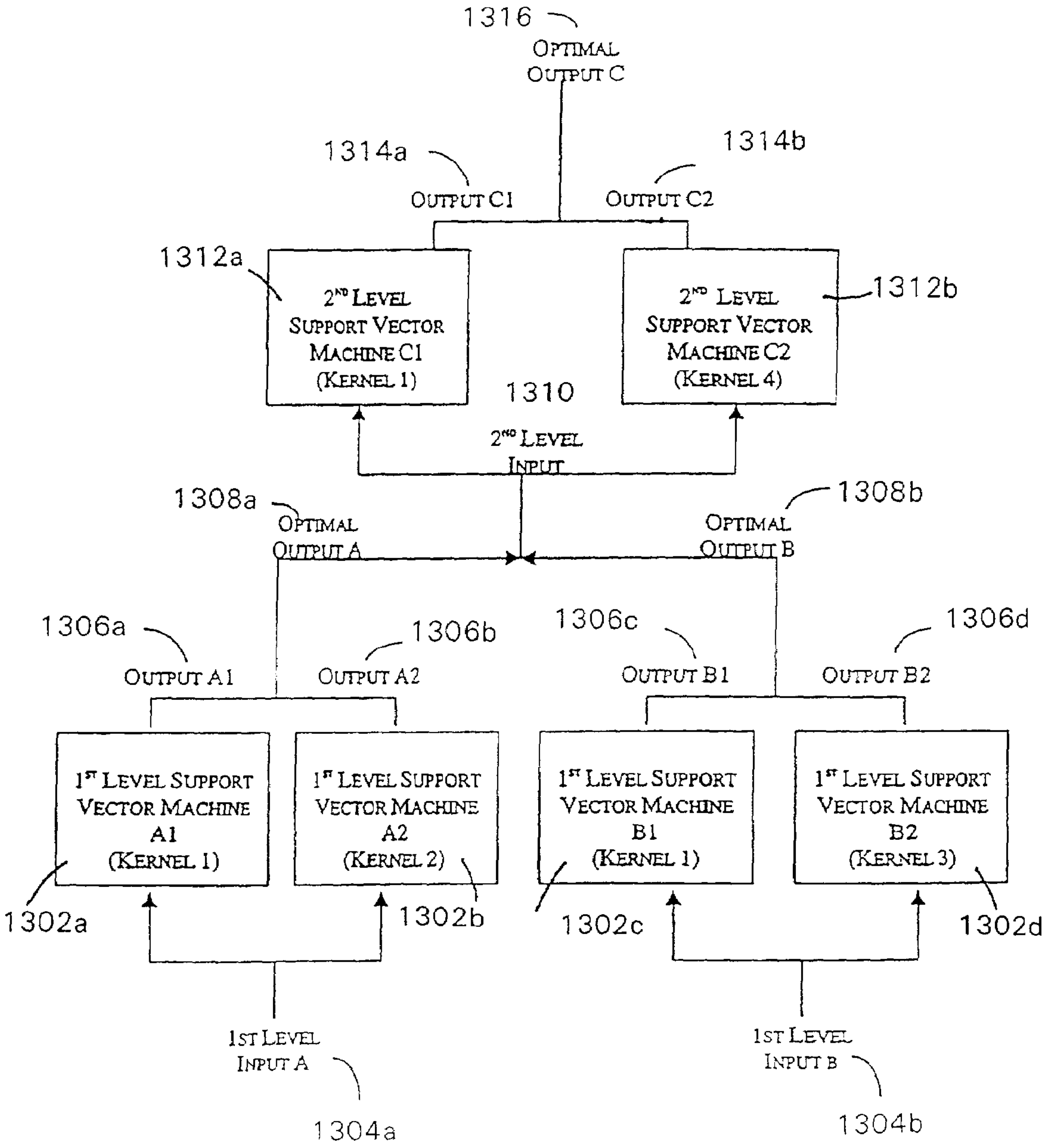
FIG. 8 is a functional block diagram illustrating a hierarchical system of multiple support vector machines.

FIG. 8 illustrates an exemplary hierarchical system of SVMs. As shown, one or more first-level SVMs 1302*a* and 1302*b* may be trained and tested to process a first type of input data 1304*a*, such as mammography data, pertaining to a sample of medical patients. One or more of these SVMs may comprise a distinct kernel, indicated as "KERNEL 1" and "KERNEL 2". Also, one or more additional first-level SVMs 1302*c* and 1302*d* may be trained and tested to process a second type of data 1304*b*, which may be, for example, genomic data for the same or a different sample of medical patients. Again, one or more of the additional SVMs may comprise a distinct kernel, indicated as "KERNEL 1" and "KERNEL 3". The output from each of the like first-level SVMs may be compared with each other, e.g., 1306*a* compared with 1306*b*; 1306*c* compared with 1306*d*, in order to determine optimal outputs 1308*a* and 1308*b*. Then, the optimal outputs from the two groups or first-level SVMs, i.e., outputs 1308*a* and 1308*b*, may be combined to form a new multi-dimensional input data set 1310, for example, relating to mammography and genomic data. The new data set may then be processed by one or more appropriately trained and tested second-level SVMs 1312*a* and 1312*b*. The resulting outputs 1314*a* and 1314*b* from second-level SVMs 1312*a* and 1312*b* may be compared to determine an optimal output 1316. Optimal output 1316 may identify causal relationships between the mammography and genomic data points. As should be apparent to those of skill in the art, other combinations of hierarchical SVMs may be used to process either in parallel or serially, data of different types in any field or industry in which analysis of data is desired.

The problem of selection of a small amount of data from a large data source, such as a gene subset from a microarray, is particularly solved using the methods, devices and systems described herein. Previous attempts to address this problem used correlation techniques, i.e., assigning a coefficient to the strength of association between variables. Preferred methods described herein use support vector machines methods based on recursive feature elimination (RFE). In examining genetic data to find determinative genes, these methods eliminate gene redundancy automatically and yield better and more compact gene subsets. The methods, devices and systems described herein can be used with publically available data to find relevant answers, such as genes determinative of a cancer diagnosis, or with specifically generated data.

There are many different methods for analyzing large data sources. The following examples are directed at gene expression data manipulations, though any data can be used in the methods, systems and devices described herein. There are studies of gene clusters discovered by unsupervised or supervised learning techniques. Preferred methods comprise application of state-of-the art classification algorithms, SVMs, in determining a small subset of highly discriminat genes that can be used to build very reliable cancer classifiers. Identification of discriminant genes is beneficial in confirming recent discoveries in research or in suggesting avenues for research or treatment. Diagnostic tests that measure the abundance of a given protein in bodily fluids may be derived from the discovery of a small subset of discriminant genes.

The examples provided below demonstrate the effectiveness of SVMs in discovering informative features or attributes. Use of SVMs and the methods herein, are qualitatively and quantitatively advantageous when compared with other methods.

In classification methods using SVMs, the input is a vector referred to as a "pattern" of n components referred to as "features". F is defined as the n-dimensional feature space. In the examples given, the features are gene expression coefficients and the patterns correspond to patients. While the present discussion is directed to two-class classification problems, this is not to limit the scope of the invention. The two classes are identified with the symbols (+) and (−). A training set of a number of patterns $\{x_1, x_2, \ldots x_k, \ldots x_l\}$ with known class labels $\{y_1, y_2, \ldots y_k, \ldots y_l\}$, $y_k \in \{-1,+1\}$, is given. The training patterns are used to build a decision function (or discriminant function) D(x), that is a scalar function of an input pattern x. New patterns are classified according to the sign of the decision function:

$D(x)>0 \rightarrow x \in$ class (+);

$D(x)<0 \rightarrow x \in$ class (−);

$D(x)=0$, decision boundary;

where $\in$ means "is a member of".

Decision boundaries that are simple weighted sums of the training patterns plus a bias are referred to as "linear discriminant functions". Herein, $$D(x)=w \cdot x+b, \quad (1)$$

where w is the weight vector and b is a bias value. A data set is said to be linearly separable if a linear discriminant function can separate it without error.

A common problem in classification, and machine learning in general, is the reduction of dimensionality of feature space to overcome the risk of "overfitting". Data overfitting arises when the number n of features is large, such as the thousands of genes studied in a microarray, and the number of training patterns is comparatively small, such as a few dozen patients. In such situations, one can find a decision function that separates the training data, even a linear decision function, but it will perform poorly on test data. Training techniques that use regularization, i.e., restricting the class of admissible solutions, can avoid overfitting the data without requiring space dimensionality reduction. Support Vector Machines (SVMs) use regularization, however even SVMs can benefit from space dimensionality reduction.

Another method of feature reduction is projecting on the first few principal directions of the data. Using this method, new features are obtained that are linear combinations of the original features. One disadvantage of projection methods is that none of the original input features can be discarded. Preferred methods incorporate pruning techniques that eliminate some of the original input features while retaining a minimum subset of features that yield better classification performance. For design of diagnostic tests, it is of practical importance to be able to select a small subset of genes for cost effectiveness and to permit the relevance of the genes selected to be verified more easily.

The problem of feature selection is well known in pattern recognition. Given a particular classification technique, one can select the best subset of features satisfying a given "model selection" criterion by exhaustive enumeration of all subsets of features. However, this method is impractical for large numbers of features, such as thousands of genes, because of the combinatorial explosion of the number of subsets.

Given the foregoing difficulties, feature selection in large dimensional input spaces is performed using greedy algorithms. Among various possible methods, feature ranking techniques are particularly preferred. A fixed number of top ranked features may be selected for further analysis or to design a classifier. Alternatively, a threshold can be set on the ranking criterion. Only the features whose criterion exceed the threshold are retained. A preferred method uses the ranking to define nested subsets of features, $F_1 \subset F_2 \subset \ldots \subset F$, and select an optimum subset of features with a model selection criterion by varying a single parameter: the number of features.

Errorless separation can be achieved with any number of genes greater than one. Preferred methods comprise use of a smaller number of genes. Classical gene selection methods select the genes that individually best classify the training data. These methods include correlation methods and expression ratio methods. While the classical methods eliminate genes that are useless for discrimination (noise), they do not yield compact gene sets because genes are redundant. Moreover, complementary genes that individually do not separate well are missed.

A simple feature (gene) ranking can be produced by evaluating how well an individual feature contributes to the separation (e.g. cancer vs. normal). Various correlation coefficients have been used as ranking criteria. See, e.g., T. K. Golub, et al, "Molecular classification of cancer: Class discovery and class prediction by gene expression monitoring", *Science* 286, 531–37 (1999). The coefficient used by Golub et al. is defined as:

$$w_i=(\mu_i(+)-\mu_i(-))/(\sigma_i(+)+\sigma_i(-)) \quad (2)$$

where $\mu_i$ and $\sigma_i$ are the mean and standard deviation, respectively, of the gene expression values of a particular gene i for all the patients of class (+) or class (−), i=1, . . . n. Large positive $w_i$ values indicate strong correlation with class (+) whereas large negative $w_i$ values indicate strong correlation with class (−). The method described by Golub, et al. for feature ranking is to select an equal number of genes with positive and with negative correlation coefficient. Other methods use the absolute value of $w_i$ as ranking criterion, or a related coefficient, $$(\mu_i(+)-\mu_i(-))^2/(\sigma_i(+)^2+\sigma_i(-)^2). \quad (3)$$

What characterizes feature ranking with correlation methods is the implicit orthogonality assumptions that are made. Each coefficient $w_i$ is computed with information about a single feature (gene) and does not take into account mutual information between features.

One use of feature ranking is in the design of a class predictor (or classifier) based on a pre-selected subset of genes. Each feature which is correlated (or anti-correlated) with the separation of interest is by itself such a class predictor, albeit an imperfect one. A simple method of classification comprises a method based on weighted voting: the features vote in proportion to their correlation coefficient. Such is the method used by Golub, et al. The weighted voting scheme yields a particular linear discriminant classifier:

$$D(x)=w \cdot (x-\mu), \quad (4)$$

where w is $w_i=(\mu_i(+)-\mu_i(-))/(\sigma_i(+)+\sigma_i(-))$ and $\mu=(\mu_i(+)+\mu(-))/2$ Another classifier or class predictor is Fisher's linear discriminant. Such a classifier is similar to that of Golub et al. where $$w=S^{-1}(\mu(+)+\mu(-)), \quad (5)$$

where S is the (n,n) within class scatter matrix defined as $$S = \sum_{x \in X(+)} (x - \mu(+))(x - \mu(+))^T + \sum_{x \in X(-)} x - \mu(-))(x - \mu(-))^T, \quad (6)$$

where μ is the mean vector over all training patters and X(+) and X(−) are the training sets of class (+) and (−), respectively. This form of Fisher's discriminant implies that S is invertible, however, this is not the case if the number of features n is larger than the number of examples l since the rank of S is at most l. The classifiers of Equations 4 and 6 are similar if the scatter matrix is approximated by its diagonal elements. This approximation is exact when the vectors formed by the values of one feature across all training patterns are orthogonal, after subtracting the class mean. The approximation retains some validity if the features are uncorreclated, that is, if the expected value of the product of two different features is zero, after removing the class mean. Approximating S by its diagonal elements is one way of regularizing it (making it invertible). However, features usually are correlated and, therefore, the diagonal approximation is not valid.

One aspect of the present invention comprises using the feature ranking coefficients as classifier weights. Reciprocally, the weights multiplying the inputs of a given classifier can be used as feature ranking coefficients. The inputs that are weighted by the largest values have the most influence in the classification decision. Therefore, if the classifier performs well, those inputs with largest weights correspond to the most informative features, or in this instance, genes. Other methods, known as multivariate classifiers, comprise algorithms to train linear discriminant functions that provide superior feature ranking compared to correlation coefficients. Multivariate classifiers, such as the Fisher's linear discriminant (a combination of multiple univariate classifiers) and methods disclosed herein, are optimized during training to handle multiple variables or features simultaneously.

For classification problems, the ideal objective function is the expected value of the error, i.e., the error rate computed on an infinite number of examples. For training purposes, this ideal objective is replaced by a cost function J computed on training examples only. Such a cost function is usually a bound or an approximation of the ideal objective, selected for convenience and efficiency. For linear SVMs, the cost function is:

$$J=(1/2)\|w\|^2, \quad (7)$$

which is minimized, under constraints, during training. The criteria $(w_i)^2$ estimates the effect on the objective (cost) function of removing feature i.

A good feature ranking criterion is not necessarily a good criterion for ranking feature subsets. Some criteria estimate the effect on the objective function of removing one feature at a time. These criteria become suboptimal when several features are removed at one time, which is necessary to obtain a small feature subset.

Recursive Feature Elimination (RFE) methods can be used to overcome this problem. RFE methods comprise iteratively 1) training the classifier, 2) computing the ranking criterion for all features, and 3) removing the feature having the smallest ranking criterion. This iterative procedure is an example of backward feature elimination. For computational reasons, it may be more efficient to remove several features at a time at the expense of possible classification performance degradation. In such a case, the method produces a "feature subset ranking", as opposed to a "feature ranking". Feature subsets are nested, e.g., $F_1 \subset F_2 \subset \ldots \subset F$.

If features are removed one at a time, this results in a corresponding feature ranking. However, the features that are top ranked, i.e., eliminated last, are not necessarily the ones that are individually most relevant. It may be the case that the features of a subset $F_m$ are optimal in some sense only when taken in some combination. RFE has no effect on correlation methods since the ranking criterion is computed using information about a single feature.

A preferred method of the present invention is to use the weights of a classifier to produce a feature ranking with a SVM (Support Vector Machine). The present invention contemplates methods of SVMs used for both linear and non-linear decision boundaries of arbitrary complexity, however, the example provided herein is directed to linear SVMs because of the nature of the data set under investigation. Linear SVMs are particular linear discriminant classifiers. (See Equation 1). If the training set is linearly separable, a linear SVM is a maximum margin classifier. The decision boundary (a straight line in the case of a two-dimension separation) is positioned to leave the largest possible margin on either side. One quality of SVMs is that the weights $w_i$ of the decision function D(x) are a function only of a small subset of the training examples, i.e., "support vectors". Support vectors are the examples that are closest to the decision boundary and lie on the margin. The existence of such support vectors is at the origin of the computational properties of SVM and its competitive classification performance. While SVMs base their decision function on the support vectors that are the borderline cases, other methods such as the previously-described method of Golub, et al., base the decision function on the average case.

A preferred method of the present invention comprises using a variant of the soft-margin algorithm where training comprises executing a quadratic program as described by Cortes and Vapnik in "Support vector networks", 1995, *Machine Learning,* 20:3, 273–297, which is herein incorporated in its entirety. The following is provided as an example, however, different programs are contemplated by the present invention and can be determined by those skilled in the art for the particular data sets involved.

Inputs comprise Training examples (vectors) $\{x_1, x_1, \ldots x_k \ldots x_l\}$ and class labels $\{y_1, y_2 \ldots y_k \ldots y_l\}$. To identify the optimal hyperplane, the following quadratic program is executed:

$$\begin{cases} \text{Minimize over } \alpha_k: \\ J = (1/2)\sum_{hk} y_h y_k \alpha_h \alpha_k (x_h \cdot x_k + \lambda\delta_{hk}) - \sum_k \alpha_k \\ \text{subject to:} \\ 0 \le \alpha_k \le C \text{ and } \sum_k \alpha_k y_k = 0 \end{cases} \quad (8)$$

with the resulting outputs being the parameters $\alpha_k$, where the summations run over all training patterns $x_k$ that are n dimensional feature vectors, $x_h \cdot x_k$ denotes the scalar product, $y_k$ encodes the class label as a binary value=1 or −1, $\delta h_k$ is the Kronecker symbol ($\delta h_k$=1 if h=k and 0 otherwise), and λ and C are positive constants (soft margin parameters). The soft margin parameters ensure convergence even when the problem is non-linearly separable or poorly conditioned. In such cases, some support vectors may not lie on the margin. Methods include relying on λ or C, but preferred methods, and those used in the Examples below, use a small value of λ (on the order of $10^{-14}$) to ensure numerical stability. For the Examples provided herein, the solution is rather insensitive to the value of C because the training data sets are linearly separable down to only a few features. A value of C=100 is adequate, however, other methods may use other values of C.

The resulting decision function of an input vector x is:

$$D(x) = w \cdot x + b \tag{9}$$

with $$w = \sum_k \alpha_k y_k x_k \text{ and } b = \langle y_k - w \cdot x_k \rangle$$

The weight vector w is a linear combination of training patterns. Most weights $\alpha_k$ are zero. The training patterns with non-zero weights are support vectors. Those having a weight that satisfies the strict inequality $0<\alpha_k<C$ are marginal support vectors. The bias value b is an average over marginal support vectors.

The following sequence illustrates application of recursive feature elimination (RFE) to a SVM using the weight magnitude as the ranking criterion. The inputs are training examples (vectors): $X_0=[x_1, x_2, \ldots x_k \ldots x_l]^T$ and class labels $Y=[y_1, y_2 \ldots y_k \ldots y_l]^T$.

Initalize:

Subset of surviving features s=[1, 2, . . . n]

Features ranked list r=[ ]

Repeat until s=[ ]

Restrict training examples to good feature indices $X=X_0(:,s)$

Train the classifier

α=SVM train(X,y)

Compute the weight vector of dimension length(s):

$$w = \sum_k \alpha_k y_k x_k$$

Compute the ranking criteria $c_i=(w_i)^2$, for all i

Find the feature with smallest ranking criterion f=argmin(c)

Update feature ranked list r=[s(f),r]

Eliminate the feature with smallest ranking criterion s=s(1:f−1, f=1:length (s))

The output comprises feature ranked list r.

The above steps can be modified to increase computing speed by generalizing the algorithm to remove more than one feature per step.

In general, RFE is computationally expensive when compared against correlation methods, where several thousands of input data points can be ranked in about one second using a Pentium® processor, and weights of the classifier trained only once with all features, such as SVMs or pseudo-inverse/mean squared error (MSE). A SVM implemented using non-optimized MatLab® code on a Pentium® processor can provide a solution in a few seconds. To increase computational speed, RFE is preferrably implemented by training multiple classifiers on subsets of features of decreasing size. Training time scales linearly with the number of classifiers to be trained. The trade-off is computational time versus accuracy. Use of RFE provides better feature selection than can be obtained by using the weights of a single classifier. Better results are also obtained by eliminating one feature at a time as opposed to eliminating chunks of features. However, significant differences are seen only for a smaller subset of features such as fewer than 100. Without trading accuracy for speed, RFE can be used by removing chunks of features in the first few iterations and then, in later iterations, removing one feature at a time once the feature set reaches a few hundreds. RFE can be used when the number of features, e.g., genes, is increased to millions. Furthermore, RFE consistently outperforms the naïve ranking, particularly for small feature subsets. (The naïve ranking comprises ranking the features with $(w_i)^2$, which is computationally equivalent to the first iteration of RFE.) The naïve ranking orders features according to their individual relevance, while RFE ranking is a feature subset ranking. The nested feature subsets contain complementary features that individually are not necessarily the most relevant. An important aspect of SVM feature selection is that clean data is most preferred because outliers play an essential role. The selection of useful patterns, support vectors, and selection of useful features are connected.

Pre-processing can have a strong impact on SVM-RFE. In particular, feature scales must be comparable. One pre-processing method is to subtract the mean of a feature from each feature, then divide the result by its standard deviation. Such pre-processing is not necessary if scaling is taken into account in the computational cost function.

In addition to the above-described linear case, SVM-RFE can be used in nonlinear cases and other kernel methods. The method of eliminating features on the basis of the smallest change in cost function, as described herein, can be extended to nonlinear uses and to all kernel methods in general. Computations can be made tractable by assuming no change in the value of the α's. Thus, the classifer does not need to be retrained for every candidate feature to be eliminated.

Specifically, in the case of SVMs, the cost function to be minimized (under the constraints $0\leqq\alpha_k\leqq C$ and $\Sigma_k\alpha_k\gamma_k=0$) is:

$$J=(1/2)\alpha^T H\alpha-\alpha^T 1, \tag{10}$$

where H is the matrix with elements $\gamma_h\gamma_k K(x_h,x_k)$, K is a kernel function that measures the similarity between $x_h$ and $x_k$, and 1 is an l dimensional vector of ones.

An example of such a kernel function is $$K(x_h,x_k)=\exp(-\gamma\|x_h-x_k\|^2). \tag{11}$$

To compute the change in cost function caused by removing input component i, one leaves the α's unchanged and recomputes matrix H. This corresponds to computing $K(x_h(-i), x_k(-i))$, yielding matrix H(−i), where the notation (−i) means that component i has been removed. The resulting ranking coefficient is:

$$DJ(i)=(1/2)\alpha^T H\alpha-(1/2)\alpha^T H(-i)\alpha \tag{12}$$

The input corresponding to the smallest difference DJ(i) shall be removed. The procedure is iterated to carry out Recursive Feature Elimination (RFE).

The present invention is directed to methods, systems and devices for using state-of the art classifiers such as a SVM disclosed herein, that uses RFE, to provide information to others through readily-accessed channels. A preferred embodiment of the methods of providing such information comprises the following steps. Data to be analyzed is provided. This data may come from customers, research facilities, academic institutions, national laboratories, commercial entities or other public or confidential sources. The source of the data and the types of data provided are not crucial to the methods. The data may be provided to the SVM through any means such as via the internet, server linkages or discs, CDs, DVDs or other storage means.

The data is input into computer system, preferably a SVM-RFE. The SVM-RFE is run one or more times to generate the best features selections, which can be displayed in an observation graph. The SVM may use any algorithm and the data may be preprocessed and postprocessed if needed. Preferably, a server contains a first observation graph that organizes the results of the SVM activity and selection of features.

The information generated by the SVM may be examined by outside experts, computer databases, or other complementary information sources. For example, if the resulting feature selection information is about selected genes, biologists or experts or computer databases may provide complementary information about the selected genes, for example, from medical and scientific literature. Using all the data available, the genes are given objective or subjective grades. Gene interactions may also be recorded.

The information derived from the SVM and the other information sources are combined to yield a global combined graph. The graph provides information such as multiple alternative candidate subsets of selected features, such as genes, with scores attached to them. For example, in the gene selection data used herein, the score reflects how predictive the genes are from a statisical point of view and how interesting they are from a biological point of view.

The graph can be explored with a computer means, such as a browser. The knowledge base may be built interactively while exploring the graph. The results of the study, such as the best fitting genes, are returned to the data provider, or to the final user, or are sent to another entity which desires the information or are made available on the internet or via a dedicated on-line servive. Financial transactions may also occur at several steps. A final user is one who receives the information determined by the methods herein.

A preferred selection browser is preferably a graphical user interface that would assist final users in using the generated information. For example, in the examples herein, the selection browser is a gene selection browser that assists the final user is selection of potential drug targets from the genes identified by the SVM RFE. The inputs are the observation graph, which is an output of a statistical analysis package and any complementary knowledge base information, preferably in a graph or ranked form. For example such complementary information for gene selection may include knowledge about the genes, functions, derived proteins, meaurement assays, isolation techniques, etc. The user interface preferably allows for visual exploration of the graphs and the product of the two graphs to identify promising targets. The browser does not generally require intensive computations and if needed, can be run on other computer means. The graph generated by the server can be precomputed, prior to access by the browser, or is generated in situ and functions by expanding the graph at points of interest.

In a preferred embodiment, the server is a statistical analysis package, and in the gene feature selection, a gene selection server. For example, inputs are patterns of gene expression, from sources such as DNA microarrays or other data sources. Outputs are an observation graph that organizes the results of one or more runs of SVM RFE. It is optimum to have the selection server run the computationally expensive operations.

A preferred method of the server is to expand the information acquired by the SVM. The server can use any SVM results, and is not limited to SVM RFE selection methods. As an example, the method is directed to gene selection, though any data can be treated by the server. Using SVM RFE for gene selection, gene redundancy is eliminated, but it is informative to know about discriminant genes that are correlated with the genes selected. For a given number N of genes, only one combination is retained by SVM-RFE. In actuality, there are many combinations of N different genes that provide similar results.

A combinatorial search is a method allowing selection of many alternative combinations of N genes, but this method is prone to overfitting the data. SVM-RFE does not overfit the data. SVM-RFE is combined with supervised clustering to provide lists of alternative genes that are correlated with the optimum selected genes. Mere substitution of one gene by another correlated gene yields substantial classification performance degradation.

Figure 9:
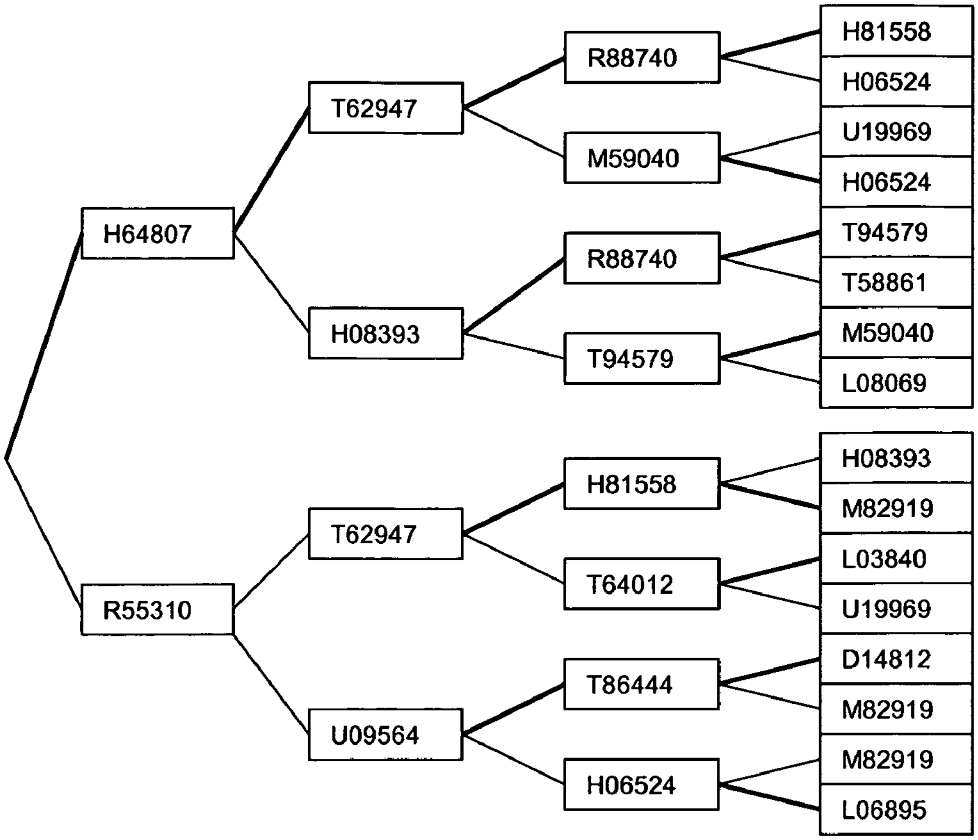
FIG. 9 illustrates a binary tree generated using an exemplary SVM-RFE.

An example of an observation graph containing several runs of SVM-RFE for colon data is shown in FIG. 9. A path from the root node to a given node in the tree at depth D defines a subset of D genes. The quality of every subset of genes can be assessed, for example, by the success rate of a classifier trained with these genes. The color of the last node of a given path indicates the quality of the subset.

The graph has multiple uses. For example, in designing a therpeutic composition that uses a maximum of four proteins, the statistical analysis does not take into account which proteins are easier to provide to a patient. In the graph, the preferred unconstrained path in the tree is indicated by the bold edges in the tree, from the root node to the darkest leaf node. This path corresponds to running a SVM-RFE. If it is found that the gene selected at this node is difficult to use, a choice can be made to use the alternative protein, and follow the remaining unconstrained path, indicated by bold edges. This decision process can be optimized by using the notion of search discussed below in a product graph.

In FIG. 9, a binary tree of depth 4 is shown. This means that for every gene selection, there are only two alternatives and selection is limited to four genes. Wider trees allow for slection from a wider variety of genes. Deeper trees allow for selection of a larger number of genes.

Figure 10A:
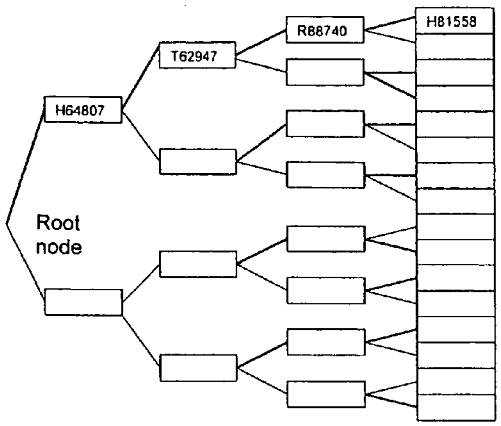
FIGS. 10*a*–10*d* illustrate an observation graph used to generate the binary tree of FIG. 9, where
Figure 10B:
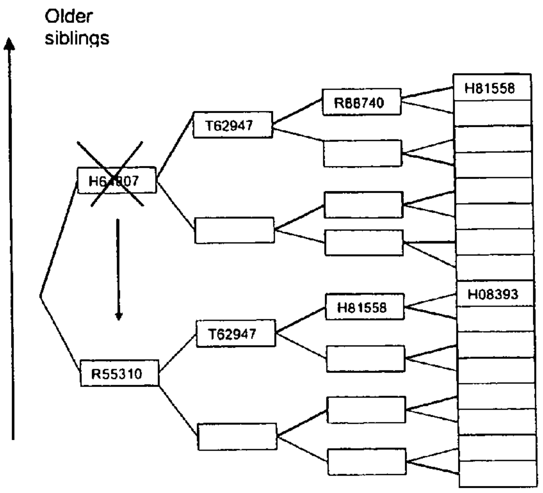
Figure 10C:
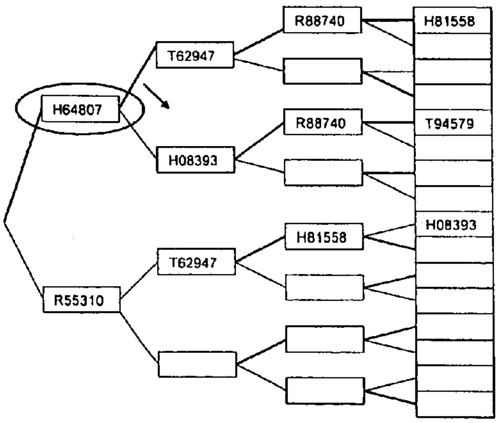
Figure 10D:
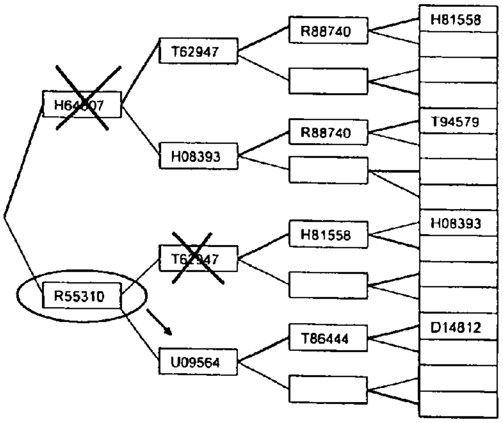

An example of construction of the tree of the observation graph is presented herein and shown in FIGS. 10*a*–10*d*. The steps of the construction of the tree of FIG. 9 are shown in FIGS. 10*a*–10*d*. In FIG. 10*a*, all of the oldest descendents of the root are labeled by the genes obtained from regular SVM-RFE gene ranking. The best ranking gene is closest to the root node. The other children of the root, from older to younger, and all their oldest decendents are then labeled. In the case of a binary tree, there are only two branches, or children, of any one node. As shown in FIG. 10*b*, the top ranking gene of FIG. 10*a* is removed, and SVM-RFE is run again. This second level of the tree is filled with the top ranking genes, from root to leaf. At this stage, all the nodes that are at depth 1 are labeled with one gene. In moving to fill the second level, the SVM is run using constrained RFE.

The constraint is that the gene of the oldest node must never be eliminated. The second child of the oldest node of root and all its oldest descendents are labeled by running the constrained RFE, as showin in FIG. 10*c*.

The examples included herein show preferred methods for determining the genes that are most correlated to the presence of cancer or can be used to predict cancer occurance in an individual. The present invention comprises these methods, and other methods, including other computational methods, usable in a learning machine for determining genes, proteins or other measurable criteria for the diagnosis or prognosis of changes in a biological system. There is no limitation to the source of the data and the data can be combinations of measurable criteria, such as genes, proteins or clinical tests, that are capable of being used to differentiate between normal conditions and changes in conditions in biological systems.

In the following examples, preferred numbers of genes were determined that result from separation of the data that discriminate. These numbers are not limiting to the methods of the present invention. Preferably, the preferred optimum number of genes is a range of approximately from 1 to 500, more preferably, the range is from 10 to 250, from 1 to 50, even more preferably the range is from 1 to 32, still more preferably the range is from 1 to 21 and most preferably, from 1 to 10. The preferred optimum number of genes can be affected by the quality and quantity of the original data and thus can be determined for each application by those skilled in the art.

Once the determinative genes are found by the learning machines of the present invention, methods and compositions for treaments of the biological changes in the organisms can be employed. For example, for the treatment of colon cancer, therapeutic agents can be administered to antagonize or agonize, enhance or inhibit activities, presence, or synthesis of the gene products. Therapeutic agents and methods include, but are not limited to, gene therapies such as sense or antisense polynucleotides, DNA or RNA analogs, pharmaceutical agents, plasmaphoresis, antiangiogenics, and derivatives, analogs and metabolic products of such agents.

Such agents are administered via parenteral or noninvasive routes. Many active agents are administered through parenteral routes of administration, intravenous, intramuscular, subcutaneous, intraperitoneal, intraspinal, intrathecal, intracerebroventricular, intraarterial and other routes of injection. Noninvasive routes for drug delivery include oral, nasal, pulmonary, rectal, buccal, vaginal, transdermal and occular routes.

Another embodiment of the present invention comprises use of testing remote from the site of determination of the patterns through means such as the internet or telephone lines. For example, a genomic test to identify the presence of genes known to be related to a specific medical condition is performed in a physician's office. Additionally, other information such as clinical data or proteomic determinations may also be made at the same time or a different time. The results of one, some or all of the tests are transmitted to a remote site that houses the SVMs. Such testing could be used for the diagnosis stages, for determining the prognosis of the disease, for determining the results of therapy and for prescriptive applications such as determining which therapy regimen is better for individual patients.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Analysis of Gene Patterns Related to Colon Cancer

Analysis of data from diagnostic genetic testing, microarray data of gene expression vectors, was performed with a SVM-RFE. The original data for this example was derived from the data presented in Alon et al., 1999. Gene expression information was extracted from microarray data resulting, after pre-processing, in a table of 62 tissues×2000 genes. The 62 tissues include 22 normal tissues and 40 colon cancer tissues. The matrix contains the expression of the 2000 genes with highest minimal intensity across the 62 tissues. Some of the genes are non-human genes.

The data proved to be relatively easy to separate. After preprocessing, it was possible to a find a weighted sum of a set of only a few genes that separated without error the entire data set, thus the data set was linearly separable. One problem in the colon cancer data set was that tumor samples and normal samples differed in cell composition. Tumor samples were normally rich in epithelial cells wherein normal samples were a mixture of cell types, including a large fraction of smooth muscle cells. While the samples could be easily separated on the basis of cell composition, this separation was not very informative for tracking cancer-related genes.

Alon et al. provides an analysis of the data based on top down hierarchical clustering, a method of unsupervised learning. The analysis shows that most normal samples cluster together and most cancer samples cluster together. Alon et al. explain that "outlier" samples that are classified in the wrong cluster differ in cell composition from typical samples. They compute a muscle index that measures the average gene expression of a number of smooth muscle genes. Most normal samples have high muscle index and cancer samples low muscle index. The opposite is true for most outliers.

Alon et al. also cluster genes and show that some genes correlate with a cancer vs. normal separation scheme but do not suggest a specific method of gene selection. They show that some genes are correlated with the cancer vs. normal separation but do not suggest a specific method of gene selection.

The gene selection method according to the present invention is compared against a reference gene selection method described in Golub et al, *Science,* 1999, which is referred to as the "baseline method" Since there was no defined training and test set, the data was randomly split into 31 samples for training and 31 samples for testing.

In Golub et al., the authors use several metrics of classifier quality, including error rate, rejection rate at fixed threshold, and classification confidence. Each value is computed both on the independent test set and using the leave-one-out method on the training set. The leave-one-out method consists of removing one example from the training set, constructing the decision function on the basis only of the remaining training data and then testing on the removed example. In this method, one tests all examples of the training data and measures the fraction of errors over the total number of training examples.

Figure 11A:
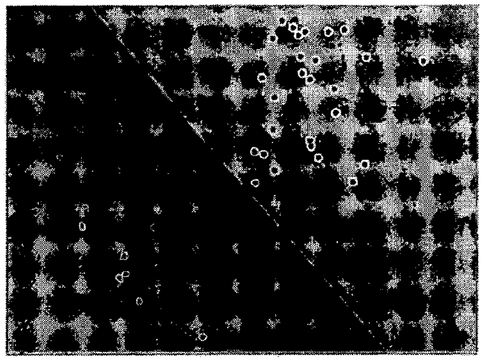
FIGS. 11*a*–11*d* graphically illustrate use of a linear discriminant classifier, where
Figure 11B:
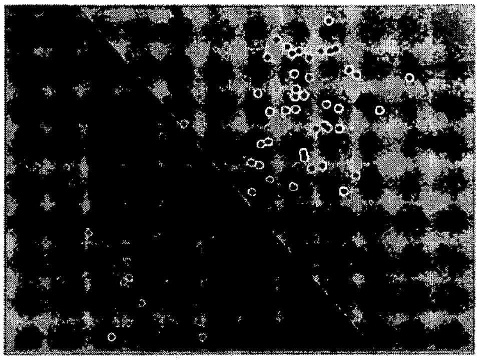
Figure 11C:
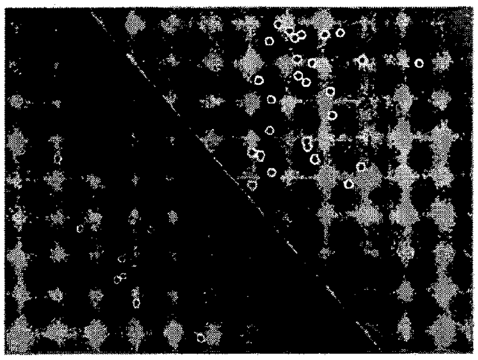
Figure 11D:
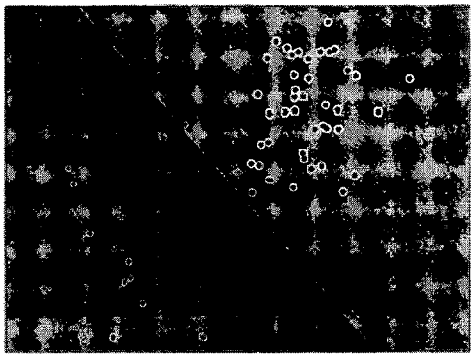

The methods of this Example of using the learning machine of the present invention use a modification of the above metrics. FIGS. 11*a–d* graphically illustrate the use of a linear discriminant classifier. FIG. 11*a* shows separation of the training examples with an SVM. FIG. 11*b* illustrates the separation of the training and test examples with the same SVM. FIG. 1 ic illustrates separation of the training examples with the baseline method. FIG. 11*d* shows separation of the training and test examples with the baseline method. The present classification methods use various decision functions (D(x) whose inputs are gene expression coefficients and whose outputs are a signed number indicative of whether or not cancer was present. The classification decision is carried out according to the sign of D(x). The magnitude of D(x) is indicative of classification confidence.

Four metrics of classifier quality were used:

Error (B1+B2)=number of errors ("bad") at zero rejection.

Reject (R1+R2)=minimum number of rejected samples to obtain zero error.

Extremal margin (E/D)=difference between the smallest output of the positive class samples and the largest output of the negative class samples (rescaled by the largest difference between outputs).

Median margin (M/D)=difference between the median output of the positive class samples and the median output of the negative class samples (rescaled by the largest difference between outputs).

Each value is computed both on the training set with the leave-one-out method and on the test set.

The error rate is the fraction of examples that are misclassified (corresponding to a diagnostic error). The error rate is complemented by the success rate. The rejection rate is the fraction of examples that are rejected (on which no decision is made because of low confidence). The rejection rate is complemented by the acceptance rate. Extremal and median margins are measurements of classification confidence. Note thatthe margin computed with the leave-one-out method or on the test set differs from the margin computed on training examples sometimes used in model selection criteria.

A method for predicting the optimum subset of genes comprised defining a criterion of optimality that uses information derived from training examples only. This criterion was checked by determining whether the predicted gene subset performed best on the test set.

A criterion that is often used in similar "model selection" problems is the leave-one-out success rate $V_{suc}$. In the present example, it was of little use since differentiation between many classifiers that have zero leave-one-out error is not allowed. Such differentiation is obtained by using a criterion that combines all of the quality metrics computed by cross-validation with the leave-one-out method:

$$Q=V_{suc}+V_{acc}+V_{ext}+V_{med}$$

where $V_{suc}$ is the success rate, $V_{acc}$ the acceptance rate, $V_{ext}$ the extremal margin, and $V_{med}$ is the median margin.

Theoretical considerations suggested modification of this criterion to penalize large gene sets. Indeed, the probability of observing large differences between the leave-one-out error and the test error increases with the size d of the gene set, using the formula below $$\epsilon(d)=sqrt(-\log(\alpha)+\log(G(d)))\cdot sqrt(p(1-p)/n)$$

where $(1-\alpha)$ is the confidence (typically 95%, i.e., $\alpha=0.05$);

p is the "true" error rate ($p<=0.01$); and n is the size of the training set.

Following the guaranteed risk principle (Vapnik, 1974), a quantity proportional to $\epsilon(d)$ was subtracted from criterion Q to obtain a new criterion:

$$C=Q-2\epsilon(d)$$

The coefficient of proportionality was computed heuristically, assuming that $V_{suc}$, $V_{acc}$, $V_{ext}$ and $V_{med}$ are independent random variables with the same error bar $\epsilon$ (d) and that this error bar is commensurate to a standard deviation. iIn this case, variances would be additive, therefore, the error bar should be multiplied by sqrt(4).

A more detailed discussion of the methods of a preferred embodiment follow. A SVM-RFE was run on the raw data to assess the validity of the method. The colon cancer data samples were split randomly into 31 examples for training and 31 examples for testing. The RFE method was run to progressively downsize the number of genes, each time dividing the number by 2. The preprocessing of the data for each gene expression value consisted of subtracting the mean from the value, then dividing the resultby the standard deviation.

The leave-one-out method with the classifier quality criterion was used to estimate the optimum number of genes. The leave-one-out method comprises taking out one example of the training set. Training is then performed on the remaining examples, withthe left out example being used to test the trained classifier. This procedure is iterated over all the examples. Every criteria is computed as an average over all examples. The overall classifier quality criterion is the sum of 4 values: the leave-one-out success rate (at zero rejections), the leave-one-out acceptance rate (at zero error), the leave-one-out extremal margin, and the leave-one-out median margin. The classifier is a linear classifier with hard margin.

Results of the SVM-RFE as taught herein show that at the optimum predicted by the method using training data only, the leave-one-out error is zero and the test performance is actually optimum. Four genes are discovered and they are:

| | |
|---|---|
| L07648 | Human MXI1 mRNA, complete cds. |
| T47377 | 71035 S-100P PROTEIN (HUMAN). |
| M76378 | Human cysteine-rich protein (CRP) gene, exons 5 and 6. |
| Z50753 | *H. sapiens* mRNA for GCAP-II/uroguanylin precursor. |

Figure 12:
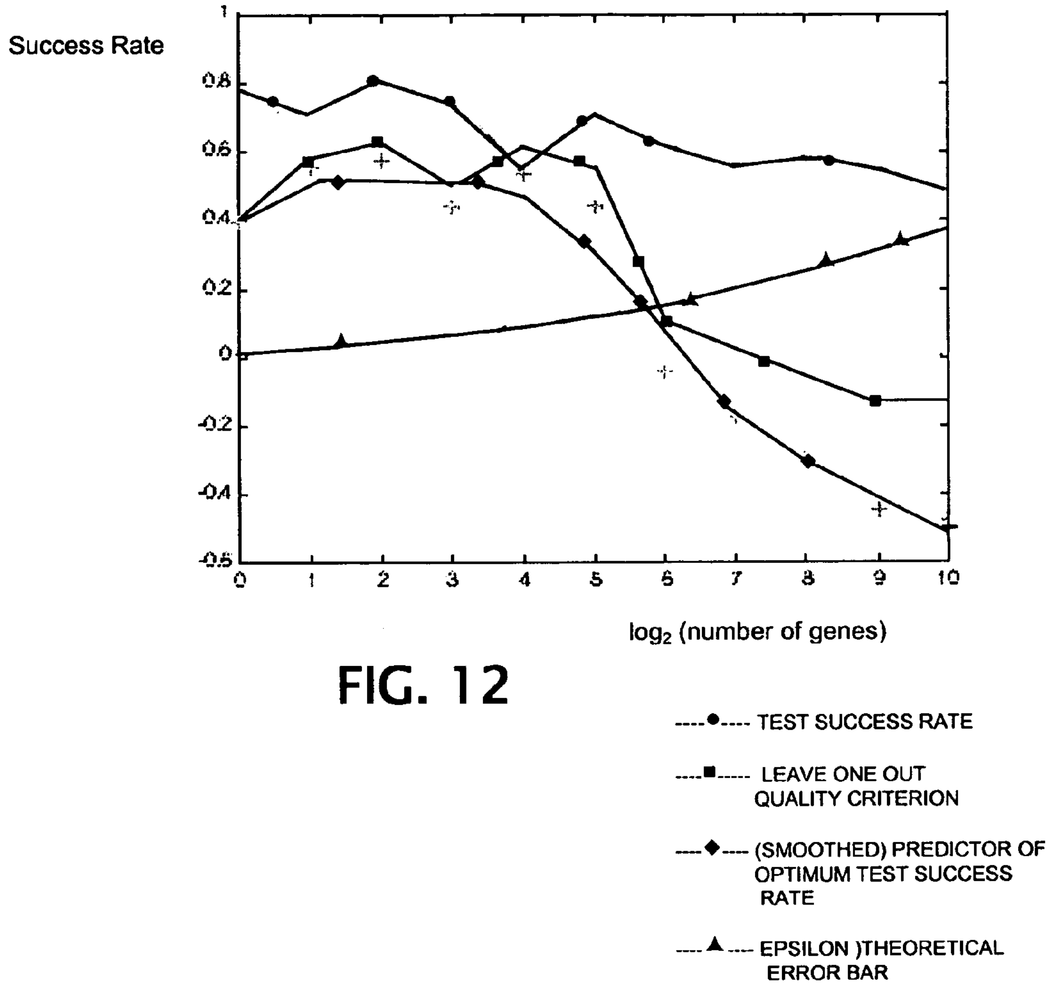
FIG. 12 is a graph of performance curves for RFE-SVM as a function of gene number.

The optimum test performance had an 81% success rate. This result was consistent with the results reported in the original paper by Alon et al. Moreover, the errors, except for one, were identified by Alon et al. as outliers. The errors were 8, 36, 34, 12, −36, and −30, with 36 being the error not identified by Alon et al. as an outlier. The number identifies the tissue while the sign indicates presence or absence of tumor (negative=tumor, positive or no sign=normal). No direct performance comparison was made because Alon et al are using unsupervised learning on the entire data set whereas this embodiment used supervised learning on half of the data set. The plot of the performance curves at a function of gene number is shown in FIG. 12. The description of the graph of FIG. 12 is as follows:

Horizontal axis=log 2(number of genes).
Vertical axis=success rate.
Curves:
- circle=test success rate;
- square=leave-one-out quality criterion;
- triangle=epsilon (theoretical error bar);
- diamonds=square−triangle (smoothed) predictor of optimum test success rate.

The optimum of the diamond curve is at log 2(num genes) =2=>num genes=4 which coincides with the optimum of the circle curve.

Preprocessing Steps

Taking the Log

Figure 13A:
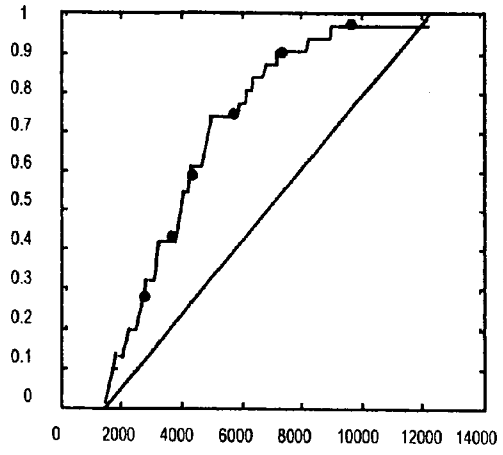
FIGS. 13*a*–13*d* show the distribution of gene expression values across tissue samples for two genes, where
Figure 13B:
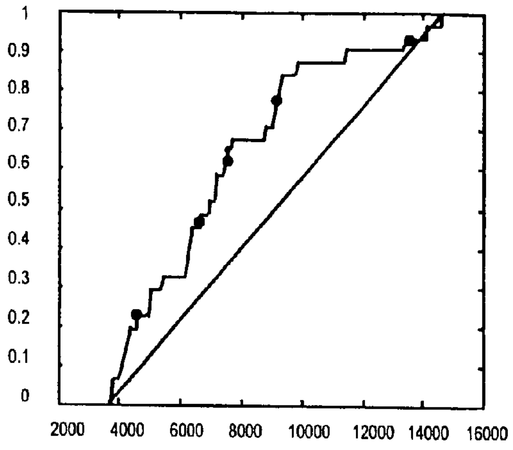
Figure 13C:
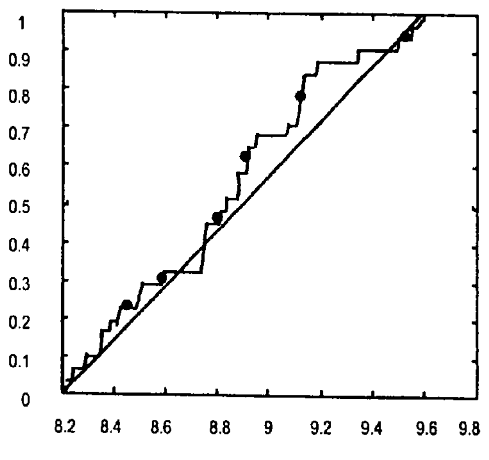
Figure 13D:
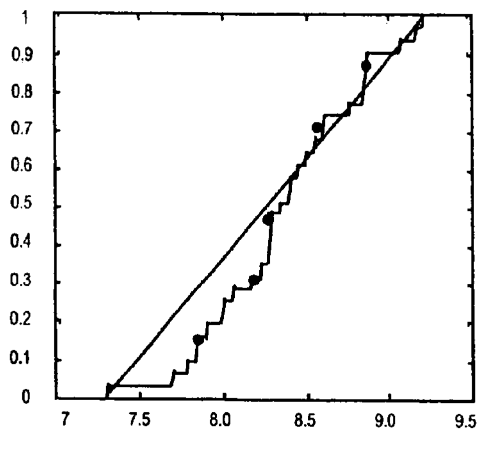

The initial preprocessing steps of the data were described by Alon et al. The data was further preprocessed in order to reduce the skew in the data distribution. FIGS. 13*a*–*d* show the distributions of gene expression values across tissue samples for two random genes (cumulative number of samples of a given expression value) which is compared with a uniform distribution. Each line represents a gene. FIGS. 13*a* and 13*b* show the raw data; FIGS. 13*c* and 13*d* are the same data after taking the log. By taking the log of the gene expression values the same curves result and the distribution is more uniform. This may be due to the fact that gene expression coefficients are often obtained by computing the ratio of two values. For instance, in a competitive hybridization scheme, DNA from two samples that are labeled differently are hybridized onto the array. One obtains at every point of the array two coefficients corresponding to the fluorescence of the two labels and reflecting the fraction of DNA of either sample that hybridized to the particular gene. Typically, the first initial preprocessing step that is taken is to take the ratio a/b of these two values. Though this initial preprocessing step is adequate, it may not be optimal when the two values are small. Other initial preprocessing steps include (a−b)/(a+b) and (log a−log b)/(log a+log b).

Subtracting the Array Mean

Figure 14A:
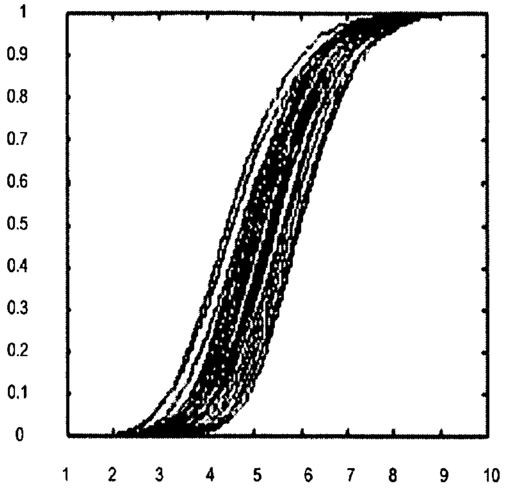
FIGS. 14*a* and 14*b* show the distribution of gene expression values across genes for all tissue samples, where
Figure 14B:
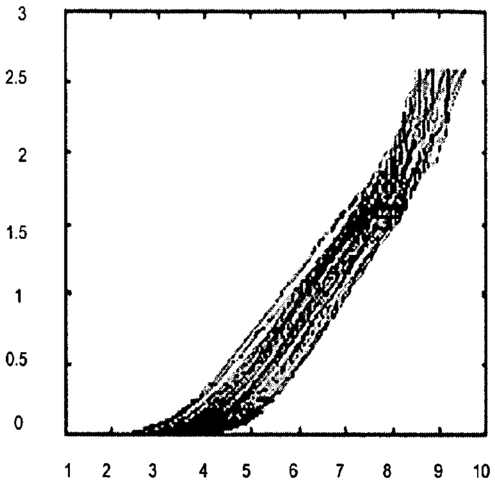

FIGS. 14*a* and *b* show the distribution of gene expression values across genes for all tissue samples. FIG. 14*a* shows the raw data and FIG. 14*b* shows the inv erf. The shape is roughly that of an erf function, indicating that the density follows approximately the Normal law. Indeed, passing the data through the inverse erf function yields almost straight parallel lines. Thus, it is reasonable to normalize the data by subtracting the mean. This preprocessing step is supported by the fact that there are variations in experimental conditions from microarray to microarray. Although standard deviation seems to remain fairly constant, the other preprocessing step selected was to divide the gene expression values by the standard deviation to obtain centered data of standardized variance.

Normalizing Each Gene Expression Across Tissue Samples

Using training data only, the mean expression value and standard deviation for each gene was computed. For all the tissue sample values of that gene (training and test), that mean was then subtracted and the resultant value was divided by the standard deviation. In some experiments, an additional preprocessing step was added by passing the data through a squashing function to diminish the importance of the outliers.

New RFE Results

The data was preprocessed as described above to produce new and improved results. The code was optimized such that RFE can be run by eliminating one gene at a time. The gene selection cross-validation process used a regular SVM.

Figure 15:
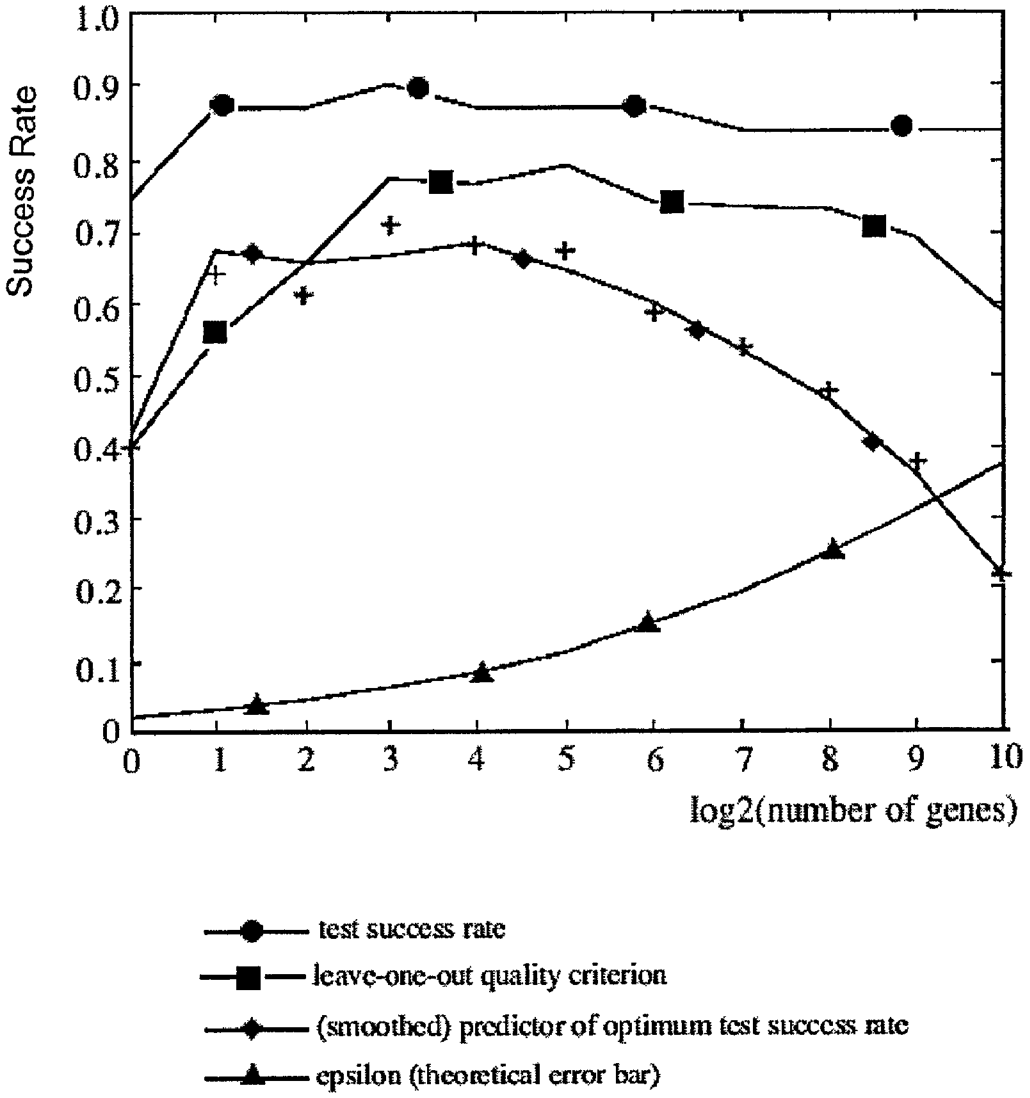
FIG. 15 is a graph of performance curves for RFE-SVM as a function of gene number after preprocessing.

The results of FIG. 15 show a significant improvement over those of FIG. 12. FIG. 15 shows the results of RFE after preprocessing. The description for FIG. 15 is as follows: Horizontal axis=log2(number of genes). Curves: circle=test success rate; square=leave-one-out quality criterion; triangle=epsilon (theoretical error bar); diamond=square−triangle (smoothed) predictor of optimum test success rate the optimum of the diamond curve is at log2(num genes)=4=>num genes=16. Reduced capacity SVM used in FIG. 12 is replaced by plain SVM. Although a log scale is still used for gene number, RFE was run by eliminating one gene at a time. The best test performance is 90% classification accuracy (8 genes). The optimum number of genes predicted from the classifier quality based on training data information only is 16. This corresponds to 87% classification accuracy on the test set. The same test performance is also achieved with only 2 genes as follows: J02854: Myosin regulatory light chain 2, smooth muscle isoform human); contains element TAR1 repetitive element.

R55310: S36390 Mitochondrial processing peptidase.

Neither of these two genes appears at the top of the list in the first experiment.

The top gene found is a smooth muscle gene, which is a gene characteristic of tissue composition and is probably not related to cancer.

Comparison with Golub's method

Figure 16:
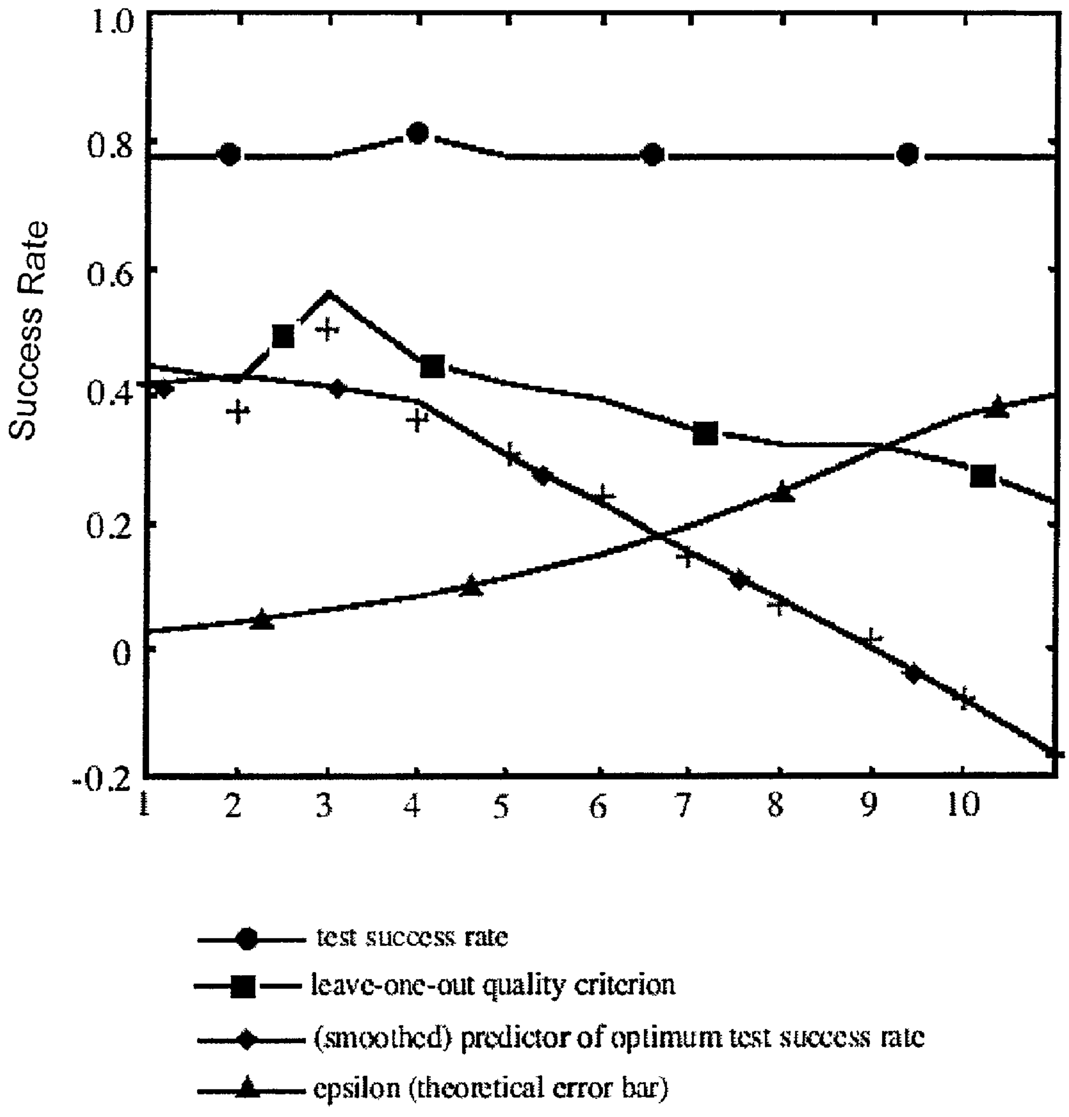
FIG. 16 shows a graphical comparison with the present invention and the methods of Golub.

Golub's gene selection method is a ranking method where genes are ordered according to the correlation between vectors of gene expression values for all training data samples and the vector of target values (+1 for normal sample and −1 for cancer sample). Golub et al select m/2 top ranked and m/2 bottom ranked genes to obtain one half of genes highly correlated with the separation and one half anti-correlated. Golub et al use a linear classifier. To classify an unknown sample, each gene "votes" for cancer or normal according to its correlation coefficient with the target separation vector. The top gene selected by Golub's method was J02854 (smooth muscle related). FIG. 16 illustrates the comparison of this embodiment's use of the baseline method with Golub et al.

The same curves as were used in FIG. 15 are shown in FIG. 16. The description for FIG. 16 is as follows: Horizontal axis=log2(number of genes). Curves: circle=test success rate; square=leave-one-out quality criterion; triangle=epsilon (theoretical error bar); diamond=square−triangle (smoothed) predictor of optimum test success rate. The data, pre-processed identically in FIGS. 15 and 16, was then treated by Golub's method and graphed in FIG. 19. It is the novel finding of the present inventors to select an optimum number of genes to use with learning machines such as SVMs.

To compare the results of the methods of this embodiment of the present invention and Golub, a statistical test was used that determines with what confidence (1−η) that one classifier is better than the other, using the formula:

$$(1-\eta)=0.5+0.5\ erf(z_\eta/sqrt(2))$$

$$z_\eta=\epsilon t/sqrt(v)$$

where t is the number of test examples, v is the total number of errors (or rejections) that only one of the two classifiers makes, and ε is the difference in error rate (or in rejection rate) and erf is the error function $$\mathrm{erf}(x)=\int_0^x \exp(-t^2)\,dt.$$

This assumes i.i.d. (independent and identically distributed) errors, one-sided risk and the approximation of the Binomial law by the Normal law.

This formula was applied to the results summarized in Table 6. In either case, $\epsilon$=3/31 and $\nu$=3. The total number of test examples is n=31. On the basis of this test, the methods of this embodiment of the present invention were better than Golub with 95.8% confidence.

TABLE 6

| Method | Optimum error rate | Error rate at the optimum number of genes |
|---|---|---|
| SVM RFE | 9.68 | 12.90 |
| Golub | 19.35 | 22.58 |

Error rates comparisons between the methods of this embodiment of the present invention and Golub's method. The sign indicates cancer (negative) or normal (positive). For this embodiment of the present invention, the best performance was at 8 genes and the optimum predicted at 16 genes. For Golub, the best performance was at 16 genes and the optimum predicted at 4 genes. Note that there was only one error difference between the best performance and the optimum predicted in either case.

Combining Clustering and Gene Selection

Because of data redundancy, it was possible to find many subsets of genes that provide a reasonable separation. To analyze the results, it was optimal to understand how these genes are related. While not wishing to be bound by any particular theory, it was the initial theory that the problem of gene selection was to find an optimum number of genes, preferably small, that separates normal tissues from cancer tissues with maximum accuracy.

SVM-RFE used a subset of genes that were complementary and thus carried little redundant information. No other information on the structure and nature of the data was provided. Because data were very redundant, a gene that had not been selected may nevertheless be informative for the separation.

Correlation methods such as Golub's method provide a ranked list of genes. The rank order characterizes how correlated the gene is with the separation. Generally, a gene highly ranked taken alone provides a better separation than a lower ranked gene. It is therefore possible to set a threshold (e.g. keep only the top ranked genes) that separates "highly informative genes" from "less informative genes".

The methods of the present invention such as SVM-RFE provide subsets of genes that are both smaller and more discriminant. The gene selection method using SVM-RFE also provides a ranked list of genes. With this list, nested subsets of genes of increasing sizes can be defined. However, the fact that one gene has a higher rank than another gene does not mean that this one factor alone characterizes the better separation. In fact, genes that are eliminated very early may be very informative but redundant with others that were kept. The 32 best genes as a whole provide a good separation but individually may not be very correlated with the target separation. Gene ranking allows for a building nested subsets of genes that provide good separations. It is not informative for how good an individual gene may be. Genes of any rank may be correlated with the 32 best genes. The correlated genes may be ruled out at some point because of their redundancy with some of the remaining genes, not because they did not carry information relative to the target separation.

The gene ranking alone is insufficient to characterize which genes are informative and which ones are not, and also to determine which genes are complementary and which ones are redundant.

Unsupervised Clustering

To overcome the problems of gene ranking alone, the data was preprocessed with an unsupervised clustering method. Genes were grouped according to resemblance (according to a given metric). Cluster centers were then used instead of genes themselves and processed by SVM-RFE to produce nested subsets of cluster centers. An optimum subset size can be chosen with the same cross-validation method used before.

Figure 17:
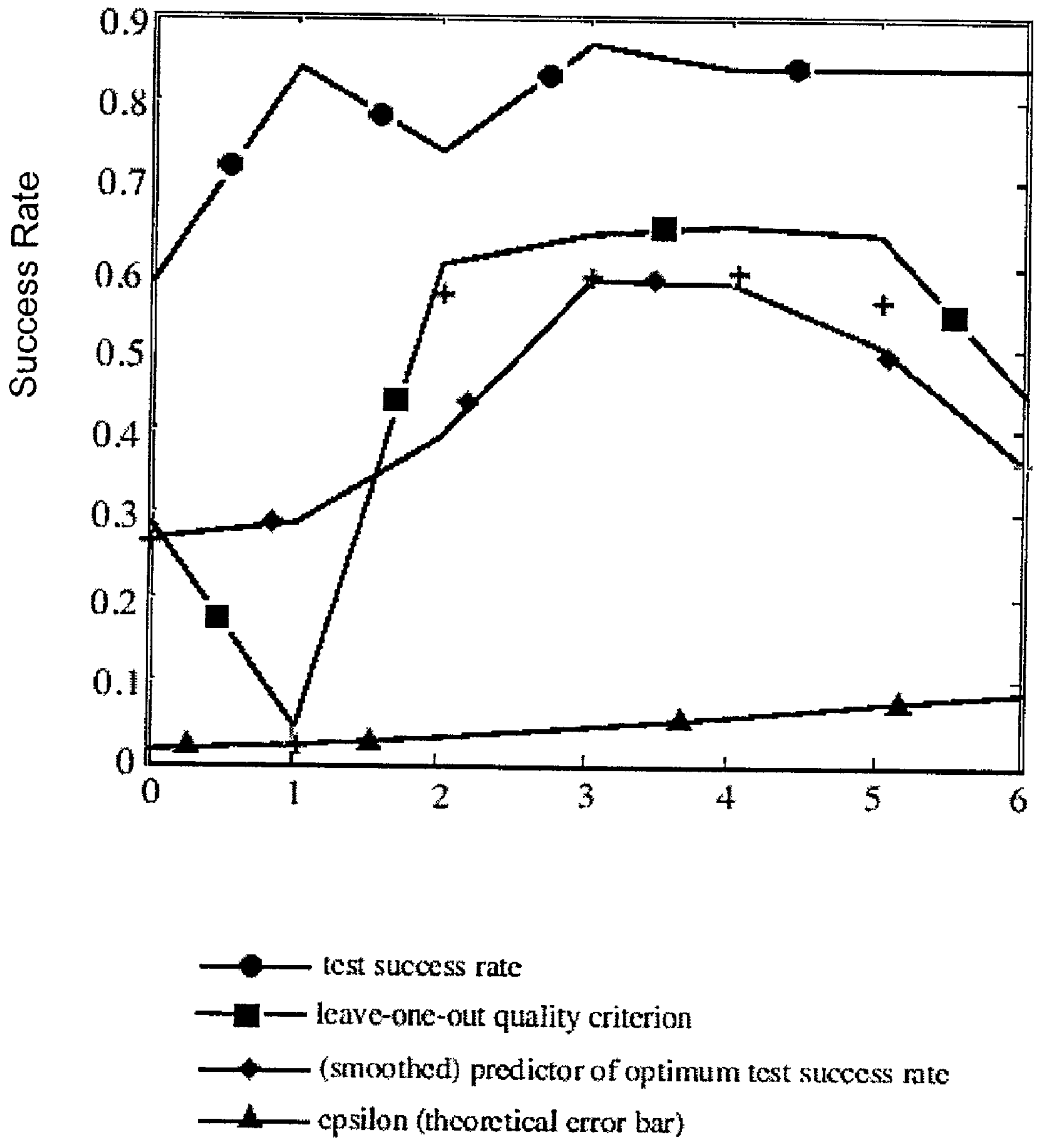
FIG. 17 shows the results of RFE when training on 100 dense QT_clust clusters.

Using the data, the $QT_{clust}$ clustering algorithm was used to produce 100 dense clusters. The similarity measure used was Pearson's correlation coefficient (as commonly used for gene clustering). FIG. 17 provides the performance curves of the results of RFE when training on 100 dense $QT_{clust}$ clusters. Horizontal axis=log 2 (number of gene cluster centers). Curves: circle=test success rates; square=leave-one-out quality criterion; triangle=epsilon (theoretical error bar); diamond=square−triangle (smoothed) predictor of optimum test success rate the optimum of the diamond curve is at log 2(number of gene cluster centers)=3=>number of gene cluster centers=8.

The results of this analysis are comparable to those of FIG. 15. The cluster elements are listed in Table 7.

TABLE 7

$QT_{clust}$ clusters selected with RFE.

| Rk | Min correl | GAN | Description |
|---|---|---|---|
| 1 | 0.82 | X54163 | TROPONIN I, CARDIAC MUSCLE (HUMAN); contains element MER22 repetitive element |
| | | D23672 | Human mRNA for biotin-[propionyl-CoA-carboxylase(ATP-hydrolysing)] ligase, complete cds. |
| | | Y00970 | |
| 2 | 0.82 | T51023 | 75127 HEAT SHOCK PROTEIN HSP 90-BETA (HUMAN). |
| | | T69446 | 82983 EUKARYOTIC INITIATION FACTOR 4A-I (HUMAN);. |
| | | R37428 | 26100 Human unknown protein mRNA, partial cds. |
| | | H89087 | 253224 SPLICING FACTOR SC35 (*Homo sapiens*) |
| | | R96357 | 197929 POLYADENYLATE-BINDING PROTEIN (*Xenopus laevis*) |
| | | T96873 | 121343 HYPOTHETICAL PROTEIN IN TRPE 3REGION (*Spirochaeta aurantia*) |
| | | H72234 | 213492 DNA-(APURINIC OR APYRIMIDINIC SITE) LYASE (HUMAN);. |
| 3 | 0.83 | T85247 | 111192 CYTOCHROME C OXIDASE POLYPEPTIDE VIC PRECURSOR (HUMAN);. |
| | | R08021 | 127104 INORGANIC PYROPHOSPHATASE (*Bos taurus*) |
| | | M22760 | *Homo sapiens* nuclear-encoded mitochondrial cytochrome c oxidase Va subunit mRNA, complete cds. |
| 4 | 0.84 | T94579 | 119384 Human chitotriosidase precursor mRNA, complete cds. |
| | | T83361 | 116665 GAMMA INTERFERON INDUCED MONOKINE PRECURSOR (*Homo sapiens*) |

TABLE 7-continued $QT_{clust}$ clusters selected with RFE.

| Rk | Min correl | GAN | Description |
|---|---|---|---|
| | | R89377 | 196061 NEDD5 PROTEIN (*Mus musculus*) |
| 5 | 0.85 | R51749 | 39237 TRANS-ACTING TRANSCRIPTIONAL PROTEIN ICP4 (*Equine herpesvirus* type 1) |
| | | R10620 | 128901 TYROSINE-PROTEIN KINASE CSK (*Homo sapiens*) |
| | | H29483 | 49967 INTERCELLULAR ADHESION MOLECULE-2 PRECURSOR (HUMAN);. |
| 6 | 0.82 | X55187 | Human mRNA for alpha-actinin, partial cds. |
| | | X74295 | *H. sapiens* mRNA for alpha 7B integrin. |
| | | R48303 | 153505 TYROSINE RICH ACIDIC MATRIX PROTEIN (*Bos taurus*) |
| | | X86693 | *H. sapiens* mRNA for hevin like protein. |
| | | H06524 | 44386 GELSOLIN PRECURSOR, PLASMA (HUMAN);. |
| 7 | 0.87 | H61410 | 211590 PLATELET GLYCOPROTEIN IV (*Homo sapiens*) |
| | | H67764 | 229939 ESTROGEN SULFOTRANSFERASE (*Bos taurus*) |
| | | U06698 | Human neuronal kinesin heavy chain mRNA, complete cds. |
| | | R39209 | 23464 HUMAN IMMUNODEFICIENCY VIRUS TYPE I ENHANCER-BINDING PROTEIN 2 (*Homo sapiens*) |
| | | R39209 | 23464 HUMAN IMMUNODEFICIENCY VIRUS TYPE I ENHANCER-BINDING PROTEIN 2 (*Homo sapiens*) |
| 8 | 0.82 | R10066 | 128808 PROHIBITIN (*Homo sapiens*) |
| | | U09564 | Human serine kinase mRNA, complete cds. |
| | | R62549 | 138906 PUTATIVE SERINE/THREONINE-PROTEIN KINASE B0464.5 IN CHROMOSOME III (*Caenorhabditis elegans*) |

The higher the cluster rank (Rk), the more important the cluster. Min correl is the minimum correlation coefficient between cluster elements.
GAN = Gene Accession Number.

With unsupervised clustering, a set of informative genes is defined, but there is no guarantee that the genes not retained do not carry information. When RFE was used on all $QT_{clust}$ clusters plus the remaining non-clustered genes (singleton clusters), the performance curves were quite similar, though the top set of gene clusters selected was completely different and included mostly singletons. The genes selected in Table 1 are organized in a structure: within a cluster, genes are redundant, across clusters they are complementary.

The cluster centers can be substituted by any of their members. This factor may be important in the design of some medical diagnosis tests. For example, the administration of some proteins may be easier than that of others. Having a choice of alternative genes introduces flexibility in the treatment and administration choices.

Ten random choices were tested, in that one gene of each of the 8 clusters was selected randomly. The average test set accuracy was 0.80 with a standard deviation of 0.05. This is to be compared with 0.87 for the cluster centers. One of the random choice tests yielded an accuracy that was superior to that of the centers (0.90): D23672, T51023, T85247, R89377, R51749, X55187, R39209, U09564.

Hierarchical clustering instead of $QT_{clust}$ clustering was used to produce lots of small clusters containing 2 elements on average. Because of the smaller cluster cardinality, there were fewer gene alternatives from which to choose. In this instance, hierarchical clustering did not yield as good a result as using $QT_{clust}$ clustering. The present invention contemplates use of any of the known methods for clustering, including but not limited to hierarchical clustering, $QT_{clust}$ clustering and SVM clustering. The choice of which clustering method to employ in the invention is affected by the initial data and the outcome desired, and can be determined by those skilled in the art.

Supervised Clustering

Another method used with the present invention was to use clustering as a post-processing step of SVM-RFE. Each gene selected by running regular SVM-RFE on the original set of gene expression coefficients was used as a cluster center. For example, the results described with reference to FIG. 15 were used. For each of the top eight genes, the correlation coefficient was computed with all remaining genes. The parameters were that the genes clustered to gene i were the genes that met the following two conditions: must have higher correlation coefficient with gene i than with other genes in the selected subset of eight genes, and must have correlation coefficient exceeding a threshold 0.

In the Figures and Tables presented herein the results for 8 genes were presented.

The clustered genes are listed in Table 8.

TABLE 8

Supervised clustering.

| Rk | Min correl | GAN | Description |
|---|---|---|---|
| 1 | 0.74 | *Z50753 | *H. sapiens* mRNA for GCAP-II/uroguanylin precursor. |
| | | M36634 | Human vasoactive intestinal peptide (VIP) mRNA, complete cds. |
| | | T95018 | 120032 40S RIBOSOMAL PROTEIN S18 (*Homo sapiens*) |
| | | M36981 | Human putative NDP kinase (nm23-H2S) mRNA, complete cds. |
| 2 | 1 | *L34657 | *Homo sapiens* platelet/endothelial cell adhesion molecule-1 (PECAM-1) gene, exon 16 and complete cds. |
| 3 | 1 | *L07648 | Human MXI1 mRNA, complete cds. |
| 4 | 1 | *T51571 | 72250 P24480 CALGIZZARIN. |
| 5 | 1 | *R88740 | 194984 ATP SYNTHASE COUPLING FACTOR 6, MITOCHONDRIAL PRECURSOR (HUMAN);. |
| 6 | 0.81 | *X70326 | *H. sapiens* MacMarcks mRNA. |
| | | X12671 | Human gene for heterogeneous nuclear ribonucleoprotein (hnRNP) core protein A1. |
| | | D59253 | Human mRNA for NCBP interacting protein 1. |
| 7 | 0.78 | *R55310 | 154810 S36390 MITOCHONDRIAL PROCESSING PEPTIDASE;. |
| | | H09137 | 46399 UBIQUINOL-CYTOCHROME C REDUCTASE CORE PROTEIN 2 PRECURSOR (HUMAN);. |
| | | T51250 | 70115 CYTOCHROME C OXIDASE POLYPEPTIDE VIII-LIVER/HEART (HUMAN). |
| 8 | 0.58 | *J02854 | MYOSIN REGULATORY LIGHT CHAIN 2, SMOOTH MUSCLE ISOFORM |

TABLE 8-continued

Supervised clustering.

| Rk | Min correl | GAN | Description |
|---|---|---|---|
| | | | (HUMAN); contains element TAR1 repetitive element;. |
| | | M26697 | Human nucleolar protein (B23) mRNA, complete cds. |
| | | X15882 | Human mRNA for collagen VI alpha-2 C-terminal globular domain. |
| | | M81635 | *Homo sapiens* erythrocyte membrane protein mRNA, complete cds. |
| | | R78934 | 146232 ENDOTHELIAL ACTIN-BINDING PROTEIN (*Homo sapiens*) |
| | | T60155 | 81422 ACTIN, AORTIC SMOOTH MUSCLE (HUMAN);. |
| | | M64110 | Human caldesmon mRNA, complete cds. |
| | | M22382 | MITOCHONDRIAL MATRIX PROTEIN P1 PRECURSOR (HUMAN);. |
| | | T60778 | 76539 MATRIX GLA-PROTEIN PRECURSOR (*Rattus norvegicus*) |
| | | M91463 | Human glucose transporter (GLUT4) gene, complete cds. |
| | | T92451 | 118219 TROPOMYOSIN, FIBROBLAST AND EPITHELIAL MUSCLE-TYPE (HUMAN);. |
| | | T67077 | 66563 SODIUM/POTASSIUM-TRANSPORTING ATPASE GAMMA CHAIN (*Ovis aries*) |
| | | X86693 | *H. sapiens* mRNA for hevin like protein. |
| | | U09564 | Human serine kinase mRNA, complete cds. |
| | | M63391 | Human desmin gene, complete cds. |

Clusters were built around the best genes found by regular SVM RFE. Parameter θ is 0.8 (see text). The higher the cluster rank (Rk), the more "relevant" the cluster should be. Min correl is the minimum correlation coefficient between cluster elements. GAN = Gene Accession Number. The cluster centers are preceded by a star.

Compared to the unsupervised clustering method and results, the supervised clustering method, in this instance, does not provide better control over the number of examples per cluster. Therefore, this method is not as good as unsupervised clustering if the goal is the ability to select from a variety of genes in each cluster. However, supervised clustering may show specific clusters that have relevance for the specific knowledge being determined. In this particular embodiment, in particular, a very large cluster of genes was found that contained several muscle genes that may be related to tissue composition and may not be relevant to the cancer vs. normal separation. Thus, those genes are good candidates for elimination from consideration as having little bearing on the diagnosis or prognosis for colon cancer.

Factoring out Tissue Composition Related Genes

The following method was directed to eliminating the identified tissue composition-related genes automatically. Genes of this type complicate the analysis of the results because it was not possible to differentiate them from genes that are informative for the cancer vs. normal separation. The results with the unsupervised learning preprocessing showed that the top ranked genes did not contain the key words "smooth muscle" that were used to detect potential tissue composition related genes. A cardiac muscle gene was still selected under this method.

Using the training set/test set split that was described earlier, other methods were used. For example, some of the top ranked genes were eliminated and the gene selection process was run again until there were no more "smooth muscle" genes or other muscle genes in the top ranked genes. However, the performance on the test set deteriorated and there was no automatic criterion that would allow the determination of when the gene set was free of tissue composition related genes.

In a preferred method of the present invention, the gene selection process was performed on the entire data set. With a larger number of training samples, the learning machine, such as the SVM used here, factored out tissue composition related genes. While not wishing to be bound by any particular theory, it is theorized that the SVM property of focusing on borderline cases (support vectors) may take advantage of a few examples of cancer tissue rich in muscle cells and of normal tissues rich in epithelial cells (the inverse of the average trend).

The resulting top ranking genes were free of muscle related genes, including the genes that were clustered with supervised clustering. In contrast, Golub's method obtains 3 smooth muscle related genes in the 7 top ranking gene cluster alone. Further, the top ranking genes found by SVM-RFE were all characterizing the separation, cancer vs. normal (Table 9). The present invention is able to not only make a quantitative difference on this data set with better classification accuracy and smaller gene subset, but is also makes a qualitative difference in that the gene set is free of tissue composition related genes.

TABLE 9

The 7 top ranked genes discovered by the methods of the present invention, in order of increasing importance.

| Rk | Sgn | GAN | Description | Possible function/relation to colon cancer |
|---|---|---|---|---|
| 1 | − | H08393 | COLLAGEN ALPHA 2(XI) CHAIN (*Homo sapiens*) | Collagen is involved in cell adhesion. Colon carcinoma cells have collagen degrading activity as part of the metastatic process. |
| 2 | − | M59040 | Human cell adhesion molecule (CD44) mRNA, complete cds. | CD44 is upregulated when colon adenocarcinoma tumor cells transit to the metastatic state. |
| 3 | − | T94579 | Human chitotriosidase precursor mRNA, complete cds. | Another chitinase (BRP39) was found to play a role in breast cancer. Cancer cells overproduce this chitinase to survive apoptosis. |
| 4 | + | H81558 | PROCYCLIC FORM SPECIFIC POLYPEPTIDE B1-ALPHA PRECURSOR (*Trypanosoma brucei brucei*) | It was shown that patients infected by Trypanosoma (a colon parasite) develop resistance against colon cancer. |
| 5 | + | R88740 | ATP SYNTHASE COUPLING FACTOR 6, MITOCHONDRIAL PRECURSOR (HUMAN) | ATP synthase is an enzyme that helps build blood vessels that feed the tumors. |
| 6 | − | T62947 | 60S RIBOSOMAL PROTEIN L24 | May play a role in controlling cell growth and |

TABLE 9-continued

The 7 top ranked genes discovered by the methods of the present invention, in order of increasing importance.

| Rk | Sgn | GAN | Description | Possible function/relation to colon cancer |
|---|---|---|---|---|
| | | | (*Arabidopsis thaliana*) | proliferation through the selective translation of particular classes of mRNA. |
| 7 | + | H64807 | PLACENTAL FOLATE TRANSPORTER (*Homo sapiens*) | Diminished status of folate has been associated with enhanced risk of colon cancer. |

Rk: rank.
Sgn: sign of correlation with the target separation,
− for over-expressed in most cancer tissues;
+ for over-expressed in most normal tissues;
GAN: Gene Accession Number;
The possible function is derived from a keyword search involving "colon cancer" or "cancer" and some words in the gene description.

Figure 18:
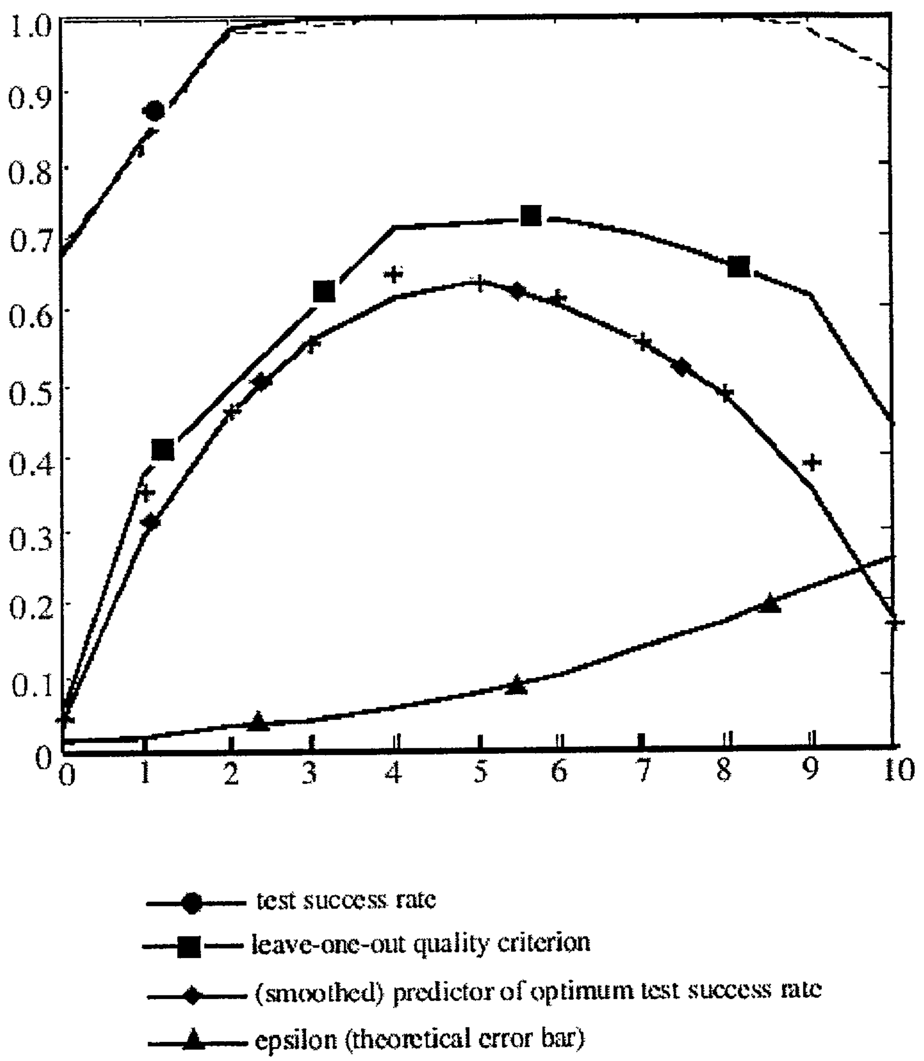
FIG. 18 shows the results of SVM-RFE when training on the entire data set.

FIG. 18 plots the results of the methods of the present invention using SVM-RFE after training on the whole data set. In FIG. 18, the curves of the plot are identified as follows: Horizontal axis=log 2(number of gene cluster centers). Vertical axis=success rate. Curves: solid circle=training success rate; dashed black=leave-one-out success rate; square=leave-one-out quality criterion; triangle=epsilon (theoretical error bar); diamond=square−triangle (smoothed) predictor of optimum test success rate. The optimum of the diamond curve is at log 2(num genes)=5=>num genes=32.

Figure 19:
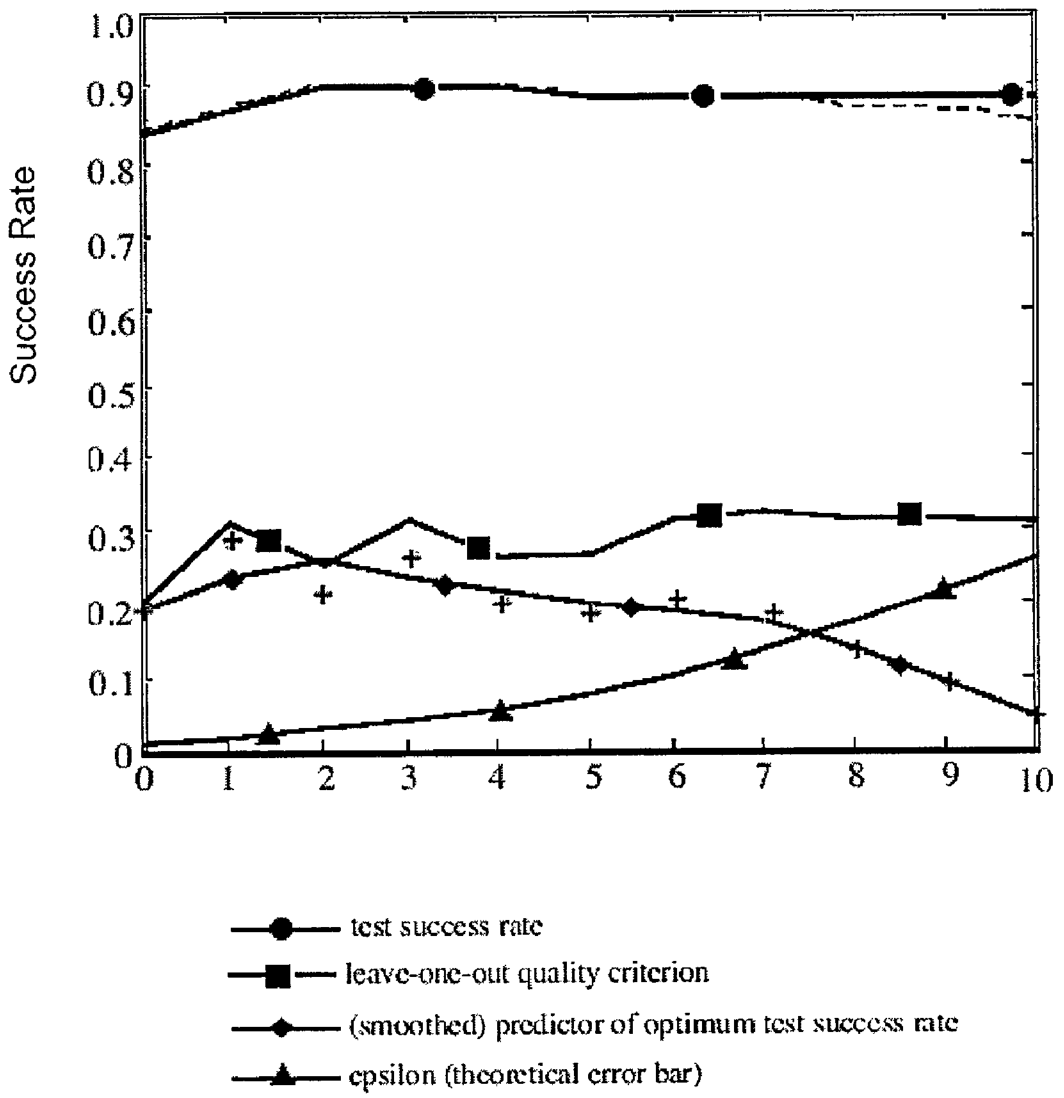
FIG. 19 shows the results of Golub's method when training on the entire data set.

For comparison, FIG. 19 plots the results obtained with Golub's method when training on the entire data set. The curves of this plot are identified as follows: Horizontal axis=log 2(number of gene cluster centers). Curves: circle=training success rate; dashed black=leave-one-out success rate; square=leave-one-out quality criterion; triangle=epsilon (theoretical error bar); diamond=square−triangle (smoothed) predictor of optimum test success rate the optimum of the diamond curve is at log2(num genes)=2=>num genes=4.

The best leave-one-out performance is 100% accuracy for SVMs and only 90% for Golub's method (6 errors). The methods of the present invention provide better results than can be obtained using Golub's method with a 99.3% confidence rate.

The optimum number of genes predicted by the leave-one-out criterion is 32 genes (per FIG. 18). In Table 10, the "muscle index" values of these 7 support vectors are provided. The muscle index is a quantity computed by Alon et al. on all samples that reflects the muscle cell contents of a sample. Most normal samples have a higher muscle index than do tumor samples. However, the support vectors do not show any such trend. There is a mix of normal and cancer samples with either high or low muscle index.

More importantly, an analysis of the genes discovered reveals that the first smooth muscle gene ranks 5 for Golub's method and only 41 for SVMs. Furthermore, the optimum number of genes using SVM prediction is 32 genes on a log plot and 21 genes on a linear plot. Therefore, SVMs are able to avoid relying on tissue composition-related genes to perform the separation. As confirmed by biological data, the top ranking genes discovered by SVMs are all related to cancer vs. normal separation. In contrast, Golub's method selects genes that are related to tissue composition and not to the distinction of cancer vs. normal in its top ranking genes.

TABLE 10

Muscle index of the support vectors of the SVM trained on the top 7 genes selected by SVM-RFE.

| Sample | −6 | 8 | 34 | −37 | 9 | −30 | −36 |
|---|---|---|---|---|---|---|---|
| Muscle index | 0.009 | 0.2 | 0.2 | 0.3 | 0.3 | 0.4 | 0.7 |

Samples with a negative sign are tumor tissues. Samples with positive signs are normal tissues. Samples wereranked in ordered of increasing muscle index. In most samples in the data set, normal tissues have higher-muscle index than tumor tissues because tumor tissues are richer in epithelial (skin) cells. This was not thecase for support vectors which show a mix of all possibilities.

Table 11 provides the seven top ranked genes discovered by the SVM-RFE of the present invention and the genes that clustered to them at threshold θ=0.75. The same information is provided for Golub's method in Table 12.

TABLE 11

SVM top ranked clusters when using all 62 tissues.

| Rk | Min correl | Sgn | GAN | Description |
|---|---|---|---|---|
| 1 | 0.75 | − | *H08393 | COLLAGEN ALPHA 2(XI) CHAIN (Homo sapiens) |
| | | − | T48804 | 40S RIBOSOMAL PROTEIN S24 (HUMAN). |
| | | − | T51529 | ELONGATION FACTOR 1-DELTA (Artemia salina) |
| 2 | 0.61 | − | *M5904 0 | Human cell adhesion molecule (CD44) mRNA, complete cds. |
| | | − | H04802 | DIHYDROPRYRIDINE-SENSITIVE L-TYPE, SKELETAL MUSCLE CALCIUM CHANNEL GAMMA SUBUNIT (Homo sapiens) |
| | | − | T65740 | SINGLE-STRANDED DNA BINDING PROTEIN P9 RECURSOR (Mus musculus) |
| | | − | L39874 | Homo sapiens deoxycytidylate deaminase gene, complete cds. |
| | | − | R44740 | DUAL SPECIFICITY MITOGEN-ACTIVATED PROTEIN KINASE KINASE 1 (Xenopus laevis) |
| 3 | 0.54 | − | *T94579 | Human chitotriosidase precursor mRNA, complete cds. |
| | | − | T63539 | INHIBIN BETA A CHAIN PRECURSOR (Mus musculus) |
| | | − | T54360 | GRANULINS PRECURSOR (HUMAN). |
| | | + | X17273 | Human HLA G (HLA 6.0) mRNA for non classical class I transplantation antigen. |
| | | + | T57882 | MYOSIN HEAVY CHAIN, NONMUSCLE TYPE A (Homo sapiens) |
| | | − | R89377 | NEDD5 PROTEIN (Mus musculus) |
| | | − | M19283 | Human cytoskeletal gamma-actin gene, complete cds. |
| | | − | T83361 | GAMMA INTERFERON INDUCED MONOKINE PRECURSOR (Homo sapiens) |
| | | − | H66786 | ESTROGEN SULFOTRANSFERASE (Bos taurus) |
| | | − | T51849 | TYROSINE-PROTEIN KINASE RECEPTOR ELK PRECURSOR (Rattus norvegicus) |
| | | − | T86444 | PROBABLE NUCLEAR ANTIGEN (Pseudorabies virus) |

TABLE 11-continued

SVM top ranked clusters when using all 62 tissues.

| Rk | Min correl | Sgn | GAN | Description |
|---|---|---|---|---|
| 4 | 1 | + | *H81558 | PROCYCLIC FORM SPECIFIC POLYPEPTIDE B1-ALPHA PRECURSOR (Trypanosoma brucei brucei) |
| 5 | 0.81 | + | *R88740 | ATP SYNTHASE COUPLING FACTOR 6, MITOCHONDRIAL PRECURSOR (HUMAN);. |
| | | + | T54670 | P13621 ATP SYNTHASE OLIGOMYCIN SENSITIVITY CONFERRAL PROTEIN PRECURSOR, MITOCHONDRIAL. |
| 6 | 0.61 | – | *T62947 | 60S RIBOSOMAL PROTEIN L24 (Arabidopsis thaliana) |
| | | – | T61609 | LAMININ RECEPTOR (HUMAN);. |
| | | | T70062 | Human nuclear factor NF45 mRNA, complete cds. |
| | | – | U14971 | Human ribosomal protein S9 mRNA, complete cds. |
| | | – | T57619 | 40S RIBOSOMAL PROTEIN S6 (Nicotiana tabacum) |
| | | – | U30825 | Human splicing factor SRp30c mRNA, complete cds. |
| | | – | L10284 | Homo sapiens integral membrane protein, calnexin, (IP90) mRNA, complete cds. |
| | | – | D00763 | PROTEASOME COMPONENT C9 (HUMAN);. |
| | | – | T58861 | 60S RIBOSOMAL PROTEIN L30E (Kluyveromyces lactis) |
| 7 | 1 | + | *H64807 | PLACENTAL FOLATE TRANSPORTER (Homo sapiens) |

Clusters are built around the best genes with threshold θ= 0.75. The higher the cluster rank (Rk), the more "relevant" the cluster should be. Min correl is the minimum correlation coefficient between cluster elements. Sgn: sign of correlation with the target separation, - for over-expressed in most cancer tissues; + for over-expressed in most normal tissues; GAN: Gene Accession Number. The cluster centers are preceded by a star. None of the genes seem to be tissue composition related.

TABLE 12

Golub top ranked clusters when using all 62 tissues.

| Rk | Min correl | Sgn | GAN | Description |
|---|---|---|---|---|
| 1 | 0.66 | + | *H06524 | GELSOLIN PRECURSOR, PLASMA (HUMAN);. |
| | | + | X55187 | Human mRNA for alpha-actinin, partial cds. |
| | | + | X68277 | *H.sapiens* CL 100 mRNA for protein tyrosine phosphatase. |
| | | + | X74295 | *H.sapiens* mRNA for alpha 7B integrin. |
| | | + | X86693 | *H.sapiens* mRNA for hevin like protein. |
| 2 | 0.59 | – | *X12671 | Human gene for heterogeneous nuclear ribonucleoprotein (hnRNP) core protein A1. |
| | | – | T57630 | S34195 RIBOSOMAL PROTEIN L3-. |
| | | – | T57633 | 40S RIBOSOMAL PROTEIN S8 (HUMAN). |
| | | – | L41559 | *Homo sapiens* pterin-4a-carbinolamine dehydratase (PCBD) mRNA, complete cds. |
| | | – | D31885 | Human mRNA (KIAA0069) for ORF (novel proetin), partial cds. |
| | | – | U26312 | Human heterochromatin protein HP1Hs-gamma mRNA, partial cds. |

TABLE 12-continued

Golub top ranked clusters when using all 62 tissues.

| Rk | Min correl | Sgn | GAN | Description |
|---|---|---|---|---|
| 3 | 0.52 | + | *J02854 | MYOSIN REGULATORY LIGHT CHAIN 2, SMOOTH MUSCLE ISOFORM (HUMAN); contains element TAR1 repetitive element;. |
| | | + | X12496 | Human mRNA for erythrocyte membrane sialoglycoprotein beta (glycophorin C). |
| | | + | T60778 | MATRIX GLA-PROTEIN PRECURSOR (*Rattus norvegicus*) |
| | | + | R78934 | ENDOTHELIAL ACTIN-BINDING PROTEIN (*Homo sapiens*) |
| | | + | T60155 | ACTIN, AORTIC SMOOTH MUSCLE (HUMAN) |
| | | + | T67077 | SODIUM/POTASSIUM TRANSPORTING ATPASE GAMMA CHAIN (Ovis aries) |
| | | – | X14958 | Human hmgI mRNA for high mobility group protein Y. |
| | | – | M26697 | Human nucleolar protein (B23) mRNA, complete cds. |
| | | + | T92451 | TROPOMYOSIN, FIBROBLAST AND EPITHELIAL MUSCLE-TYPE (HUMAN);. |
| | | – | M22382 | MITOCHONDRIAL MATRIX PROTEIN P1 PRECURSOR (HUMAN);. |
| 4 | 0.47 | + | *M63391 | Human desmin gene, complete cds. |
| | | + | U19969 | Human two-handed zinc finger protein ZEB mRNA, partial cds. |
| | | + | X12369 | TROPOMYOSIN ALPHA CHAIN, SMOOTH MUSCLE (HUMAN);. |
| | | + | Z49269 | *H.sapiens* gene for chemokine HCC-1. |
| | | + | Z49269 | *H.sapiens* gene for chemokine HCC-1. |
| | | – | T86473 | NUCLEOSIDE DIPHOSPHATE KINASE A (HUMAN);. |
| | | + | M76378 | Human cysteine-rich protein (CRP) gene, exons 5 and 6. |
| | | + | M76378 | Human cysteine-rich protein (CRP) gene, exons 5 and 6. |
| 5 | 0.63 | + | *M36634 | Human vasoactive intestinal peptide (VIP) mRNA, complete cds. |
| | | + | R48303 | TYROSINE RICH ACIDIC MATRIX PROTEIN (Bos taurus) |
| | | + | H77597 | *H.sapiens* mRNA for metallothionein (HUMAN);. |
| | | + | R44301 | MINERALOCORTICOID RECEPTOR (Homo sapiens) |
| 6 | 0.81 | + | *Z50753 | *H.sapiens* mRNA for GCAP-II/uroguanylin precursor. |
| | | + | D25217 | Human mRNA (KIAA0027) for ORF, partial cds. |
| 7 | 0.68 | + | *R87126 | MYOSIN HEAVY CHAIN, NONMUSCLE (*Gallus gallus*) |
| | | – | X54942 | *H.sapiens* ckshs2 mRNA for Cks1 protein homologue. |
| | | + | M76378 | Human cysteine-rich protein (CRP) gene, exons 5 and 6. |

Clusters are built around the best genes with threshold θ= 0.75. The higher the cluster rank (Rk), the more "relevant" the cluster should be. Min correl is the minimum correlation coefficient between cluster elements. Sgn: sign of correlation with the target separation, - for over-expressed in most cancer tissues; + for over-expressed in most normal tissues; GAN: Gene Accession Number. The cluster centers are preceded by a star. Some of the genes may be tissue composition related.

As a feature selection method, SVM-RFE differed from Golub's method in two respects. First, the mutual information between features was used by SVMs while Golub's method makes implicit independence assumptions. Second, the decision function was based only on support vectors that are "borderline" cases as opposed to being based on all examples in an attempt to characterize the "typical" cases. The use of support vectors is critical in factoring out irrelevant tissue composition-related genes. SVM-RFE was compared with RFE methods using other linear discriminant functions that do not make independence assumptions but attempts to characterize the "typical" cases. Two discriminant functions were chosen:

Fisher linear discriminant also called Linear Discriminant Analysis (LDA) (see e.g. Duda, 1973) because Golub's method approximates Fisher's linear discriminant by making independent assumptions, and Mean-Squared-Error (MSE) linear discriminant computed by Pseudo-inverse (see e.g. Duda, 1973) because when all training examples are support vectors, the pseudo-inverse solution is identical to the SVM solution.

Figure 20:
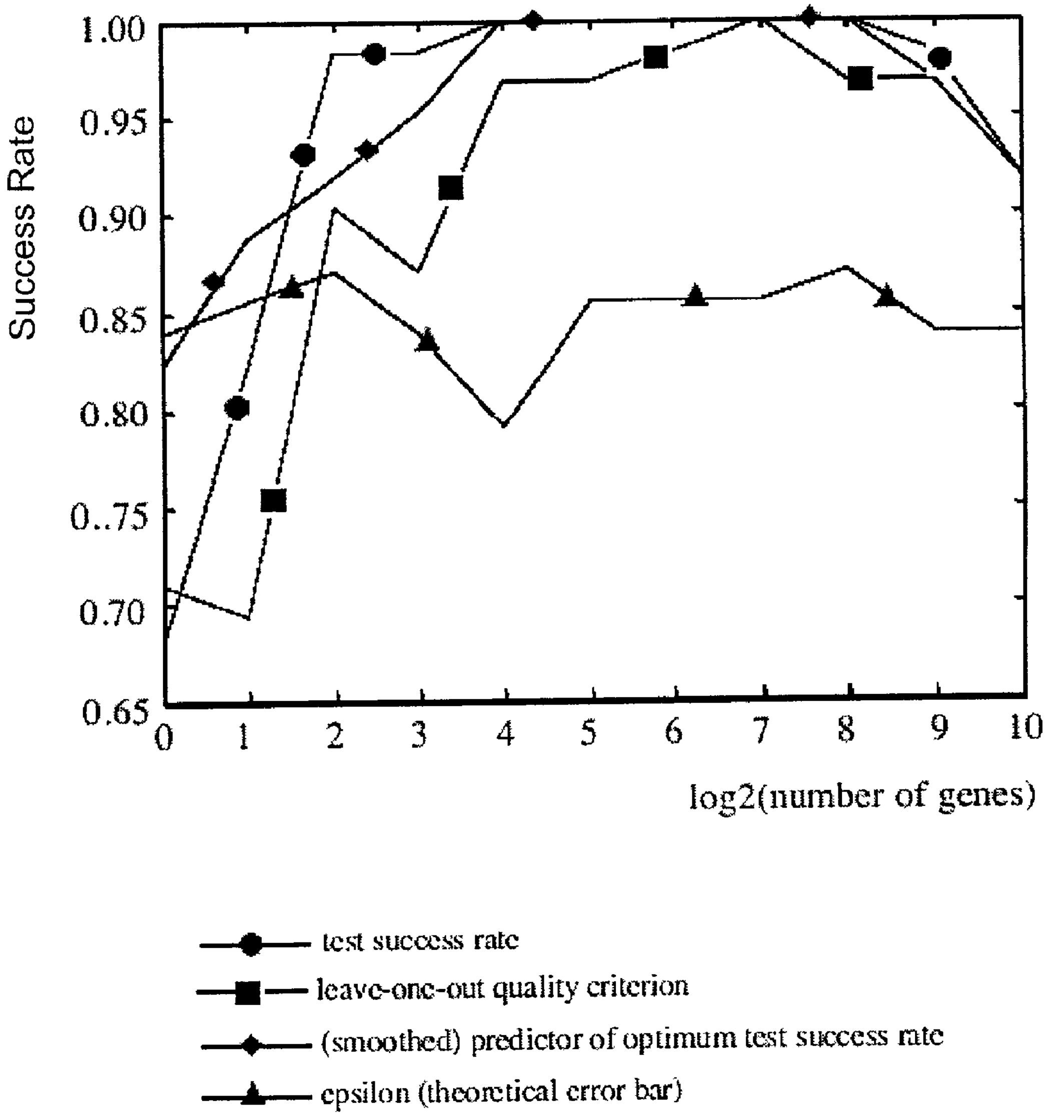
FIG. 20 shows a comparison of feature (gene) selection methods for colon cancer data using different methods.
Figure 21:
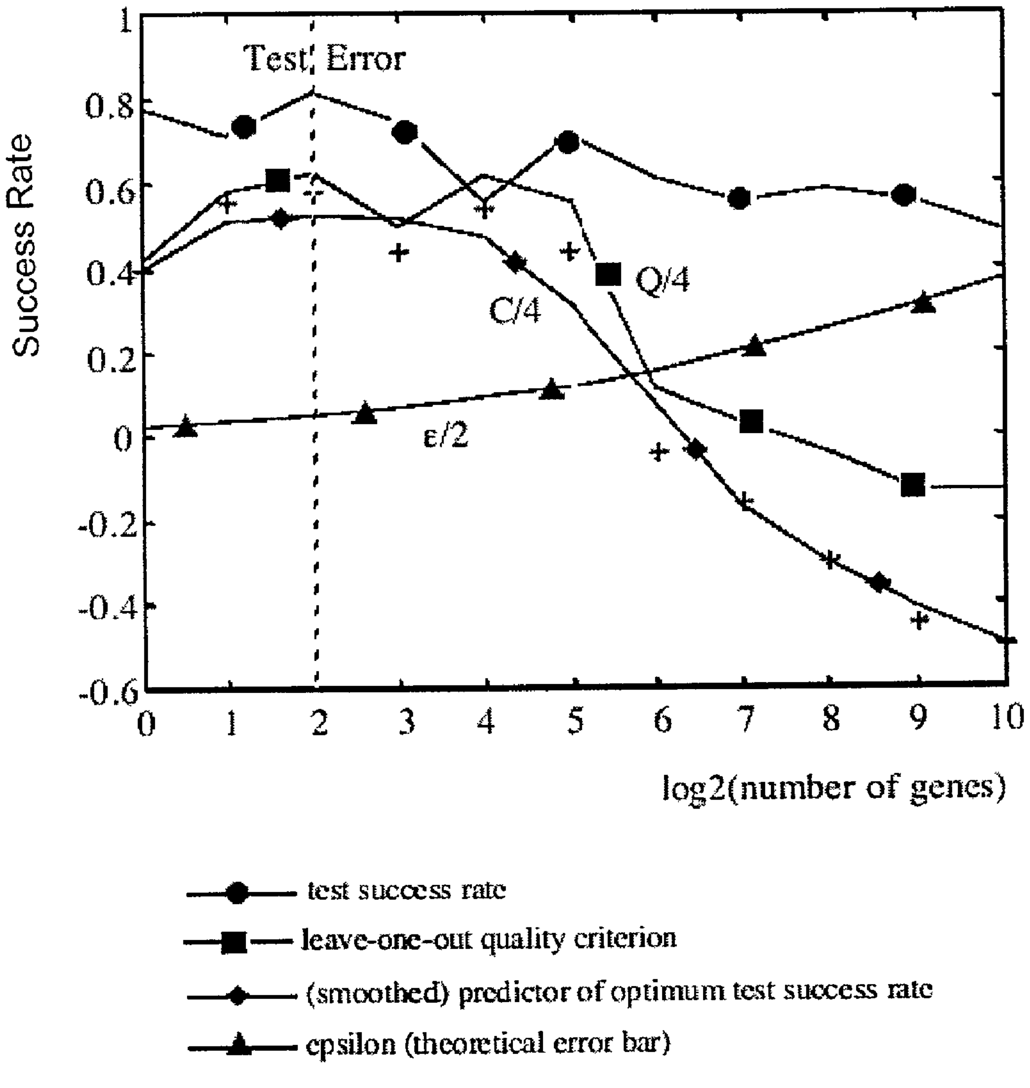
FIG. 21 shows the selection of an optimum number of genes for colon cancer data.

The results of comparison of feature (gene) selection methods for colon cancer data are plotted in FIG. 20. FIG. 21 shows the selection of an optimum number of genes for colon cancer data. The number of genes selected by Recursive Feature Elimination (RFE) was varied and was tested with different methods. Training was done on the entire data set of 62 samples. The curves represent the leave-one-out success rate. The different methods are shown in FIG. 20, with the curves being identified as follows: Circle: SVM-RFE. Square: Linear Discriminant Analysis-RFE. Diamond: Mean Squared Error (Pseudo-inverse)-RFE. Triangle: Baseline method (Golub, 1999). SVM-RFE provides the best results down to 4 genes. An examination of the genes selected reveals that SVM eliminates genes that are tissue composition-related and keeps only genes that are relevant to the cancer vs. normal separation. Conversely, other methods retain smooth muscle genes in their top ranked genes which aids in separating most samples, but is not relevant to the cancer vs. normal discrimination.

All methods that do not make independent assumptions outperform Golub's method and reach 100% leave-one-out accuracy for at least one value of the number of genes. LDA may be at a slight disadvantage on these plots because, for computational reasons, RFE was used by eliminating chunks of genes that decrease in size by powers of two. Other methods use RFE by eliminating one gene at a time.

Down to 4 genes, SVM-RFE showed better performance than all the other methods. All methods predicted with the criterion of the equation: $C=Q-2\epsilon(d)$; an optimum number of genes smaller or equal to 64. The genes ranking 1 through 64 for all the methods studied were compared. The first gene that was related to tissue composition and mentions "smooth muscle" in its description ranks 5 for Golub's method, 4 for LDA, 1 for MSE and only 41 for SVM. Therefore, this was a strong indication that SVMs make a better use of the data compared with other methods since they are the only methods that effectively factors out tissue composition-related genes while providing highly accurate separations with a small subset of genes.

FIG. 18 is a plot of an optimum number of genes for evaluation of colon cancer data. The number of genes selected by recursive gene elimination with SVMs was varied. The curves are identified as follows: Circle: error rate on the test set. Square: scaled quality criterion (Q/4). Crosses: scaled criterion of optimality (C/4). Diamond curve: result of locally smoothing the C/4. Triangle: scaled theoretical error bar ($\epsilon/2$). The curves are related by $C=Q-2\epsilon$.

The model selection criterion was established using leukemia data, its predictive power was correlated by using it on colon cancer data, without making any adjustment. The criterion also predicted the optimum accurately. The performance was not as accurate on the first trial because the same preprocessing as for the leukemia data of Example 2 was used. The results were improved substantially by adding several preprocessing steps and reached a success rate of 90% accuracy. These preprocessing steps included taking the logarithm of all values, normalizing sample vectors, normalizing feature vectors, and passing the result through a squashing function to diminish the importance of outliers [$\int(x)=c$ antan $(x/c)$] Normalization comprised subtracting the mean over all training values and dividing by the corresponding standard deviation.

The model selection criterion was used in a variety of other experiments using SVMs and other algorithms. The optimum number of genes was always predicted accurately, within a factor of two of the number of genes.

The results of the SVM-RFE analysis are confirmed in the biology literature. The best ranked genes code for proteins whose role in colon cancer has been long identified and widely studied. Such is the case of CD44, which is upregulated when colon adenocarcinoma tumor cells transit to the metastatic state (Ghina, 1998) and collagen which is involved in cell adhesion. Colon carcinoma cells have collagen degrading activity as part of the metastatic process (Karakiulakis, 1997). ATP synthase as an enzyme that helps build blood vessels to feed the tumors was published only a year ago (Mozer, 1999). Diminished status of folate has been associated with enhanced risk of colon cancer in a recent clinical study (Walsh, 1999). To this date, no known biochemical mechanism explains the role of folate in colon cancer. Knowing that gene H64807 (Placental folate transporter) was identified as one of the most discriminant genes in the colon cancer vs. normal separation shows the use of the methods of the present invention for identifying genes involved in biological changes.

In the case of human chitotriosidase, one needs to proceed by analogy with another homologous protein of the same family whose role in another cancer is under study: another chitinase (BRP39) was found to play a role in breast cancer. Cancer cells overproduce this chitinase to survive apoptosis (Aronson, 1999). Important increased chitotriosidase activity has been noticed in clinical studies of Gauchers disease patients, an apparently unrelated condition. To diagnose the presence of that disease, the chitotriosidase enzyme can be very sensitively measured. The plasma or serum prepared from less than a droplet of blood is highly sufficient for the chitotriosidase measurement (Aerts, 1996).

The 60S ribosomal protein L24 (*Arabidopsis thaliana*) is a non-human protein that is homologous a human protein located on chromosome 6. Like other ribosomal proteins, it may play a role in controlling cell growth and proliferation through the selective translation of particular classes of mRNA.

A surprisingly novel finding is the identified gene for "procyclic form specific polypeptide B1-alpha precursor (*Trypanosoma brucei brucei*)". *Trypanosoma* is a parasitic protozoa indigenous to Africa and South America and patients infected by *Trypanosoma* (a colon parasite) develop resistance against colon cancer (Oliveira, 1999). Trypanosomiasis is an ancient disease of humans and animals and is still endemic in Africa and South America.

EXAMPLE 2

Leukemia Gene Discovery

The data set, which consisted of a matrix of gene expression vectors obtained from DNA microarrays, was obtained from cancer patients with two different types of leukemia. After preprocessing, it was possible to find a weighted sum of a set of only a few genes that separated without error the entire data set, thus the data set was linearly separable. Although the separation of the data was easy, the problems present several features of difficulty, including small sample sizes and data differently distributed between training and test set.

In Golub, 1999, the authors present methods for analyzing gene expression data obtained from DNA micro-arrays in order to classify types of cancer. The problem with the leukemia data was the distinction between two variants of leukemia (ALL and AML). The data is split into two subsets: A training set, used to select genes and adjust the weights of the classifiers, and an independent test set used to estimate the performance of the system obtained. Golub's training set consisted of 38 samples (27 ALL and 11 AML) from bone marrow specimens. Their test set has 34 samples (20 ALL and 14 AML), prepared under different experimental conditions and including 24 bone marrow and 10 blood sample specimens. All samples have 7129 attributes (or features) corresponding to some normalized gene expression value extracted from the micro-array image. In this Example, the exact same experimental conditions were retained for ease of comparison with their method.

As suggested in Golub (1999) preprocessing steps were performed. From each gene expression value, the mean was subtracted and the result was divided by its standard deviation. RFE method was used and chunks of genes were eliminated at a time. At the first iteration, a number of genes were reached that was the closest power of 2. At subsequent iterations, half of the remaining genes were eliminated. Nested subsets of genes were obtained that had increasing information density. The quality of these subsets of genes was then assessed by training various classifiers, including a linear SVM, the Golub et al. classifier and Fisher's linear discriminant.

In preliminary experiments, some of the large deviations between leave-one-out error and test error could not be explained by the small sample size alone. The data analysis revealed that there are significant differences between the distribution of the training set and the test set. Various hypotheses were tested and it was found that the differences can be traced to differences in data source. In all the experiments, the performance on test data from the various sources was followed separately. The results obtained were the same, regardless of the source.

Figure 22:
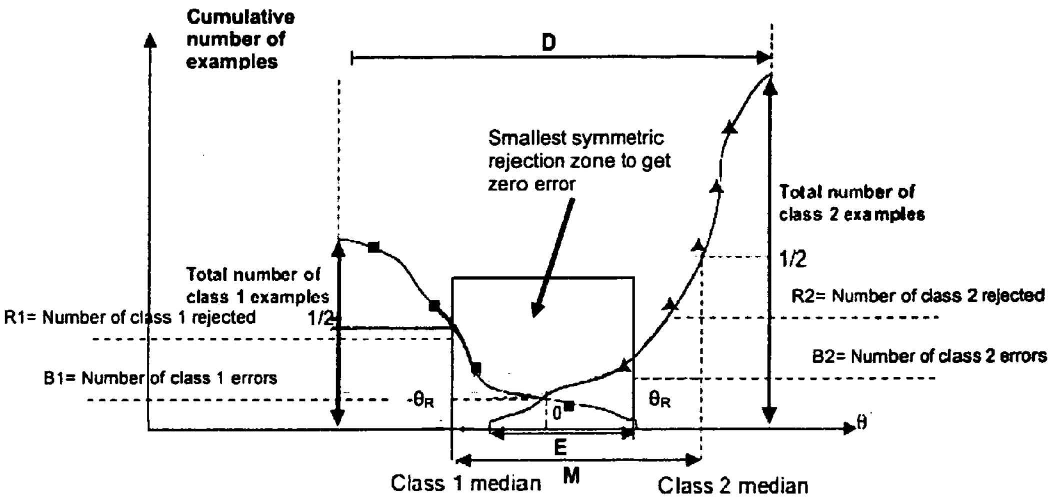
FIG. 22 shows the metrics of classifier quality. The triangle and square curves represent example distributions of two classes: class 1 (negative class) and class 2 (positive class).

In Golub, the authors use several metrics of classifier quality, including error rate, rejection rate at fixed threshold, and classification confidence. Each value is computed both on the independent test set and using the leave-one-out method on the training set. The leave-one-out method consists of removing one example from the training set, constructing the decision function on the basis only of the remaining training data and then testing on the removed example. In this method, one tests all examples of the training data and measures the fraction of errors over the total number of training examples. See FIG. 22 which shows the metrics of classifier quality. The curves (square and triangle) represent example distributions of two classes: class 1 (negative class) and class 2 (positive class).

Square: Number of examples of class 1 whose decision function value is larger than or equal to $\theta$.

Triangle: Number of examples of class 2 whose decision function value is smaller than or equal to $\theta$. The number of errors B1 and B2 are the ordinates of $\theta=0$. The number of rejected examples R1 and R2 are the ordinates of $-\theta_R$ and $\theta_R$ in the triangle and circle curves respectively. The decision function value of the rejected examples is smaller than $\theta_R$ in absolute value, which corresponds to examples of low classification confidence. The threshold $\theta_R$ is set such that all the remaining "accepted" examples are well classified. The extremal margin E is the difference between the smallest decision function value of class 2 examples and the largest decision function value of class 1 examples. On the example of the figure, E is negative. If the number of classification error is zero, E is positive. The median margin M is the difference between the median decision function value of the class 1 density and the median of the class 2 density.

In general, several cross tests were performed with the baseline method to compare gene sets and classifiers. SVMs trained on SVM selected genes or on baseline genes, and baseline classifier trained on SVM-selected genes or on baseline genes. Baseline classifier refers to the classifier of equation 4, hereinin, (Golub, 1999). Baseline genes refer to genes selected according to the ranking criterion of Equation 4 (w), herein.

First, the full set of 7129 genes (Table 13) was used. The measured values were as described earlier.

TABLE 13

Results of training classifiers on all genes (Leukemia data).

| Classifier | Error # (0 reject) | Reject # (0 error) | Extremal margin | Median margin |
|---|---|---|---|---|
| | | Leave-one-out (38 samples) | | |
| SVM | 2 | 5 | 0.01 | 0.42 |
| Baseline | 4 | 20 | −0.25 | 0.28 |
| | | Test set (34 samples) | | |
| SVM | 5 | 11 | −0.05 | 0.42 |
| Baseline | 5 | 22 | −0.24 | 0.34 |

A set of 50 genes was then selected. The 50 genes corresponded to the largest weights of the SVM trained on all genes. A new SVM was trained on these 50 genes. The results were compared with the baseline system trained with the original set of 50 features reported in the Golub et al. paper. See Table 14.

TABLE 14

Results of training on 50 genes (Leukemia data).

| Classifier | Error # (0 reject) | Reject # (0 error) | Extremal margin | Median margin |
|---|---|---|---|---|
| | | Leave-one-out (38 samples) | | |
| SVM | 2 | 5 | 0.01 | 0.42 |
| Baseline | 4 | 20 | −0.25 | 0.28 |
| | | Test set (34 samples) | | |
| SVM | 5 | 11 | −0.05 | 0.42 |
| Baseline | 5 | 22 | −0.24 | 0.34 |

In both cases, SVMs matched the performance of the baseline system or outperformed it. Using the detailed results of Tables 10 and 11, the statistical significance of the performance differences was checked with the following equation:

$$(1-\eta)=0.5+0.5\ erf(z\eta/sqrt(2))\quad z\eta=\epsilon t/sqrt(v)$$

TABLE 15

Detailed results of training on all genes (Leukemia data).

| Classifier | Test set (34 samples) Error # (0 reject) | Reject # (0 error) |
|---|---|---|
| SVM | 5 | 11 |
| Baseline | 5 | 22 |

TABLE 16

Detailed results of training on 50 genes(Leukemia data)

| Classifier | Test set (34 samples) Error # (0 reject) | Reject # (0 error) |
|---|---|---|
| SVM | 0 | 0 |
| Baseline | 1 | 5 |

According to the results of the test, the classifiers trained on 50 genes are better than those trained on all genes with high confidence (based on the error rate 97.7% confidence for Golub and 98.7% for SVM). Based on the error rate alone, the SVM classifier is not significantly better than the Golub classifier (50% confidence on all genes and 84.1% confidence on 50 genes). But, based on the rejections, the SVM classifier is significantly better than the Golub classifier (99.9% confidence on all genes and 98.7% confidence on 50 genes).

A more in-depth comparison between the method of Golub et al and SVMs on the leukemia data was made. In particular, two aspects of the problem were de-coupled: selecting a good subset of genes and finding a good decision function. The performance improvements obtained with SVMs can be traced to the SVM feature (gene) selection method. The particular decision function that was trained with these features mattered less than selecting an appropriate subset of genes.

Rather than ranking the genes once with the weights of an SVM classifier according to the naïve ranking discussed above, instead, the Recursive Feature Elimination (RFE) method was used. At each iteration, a new classifier is trained with the remaining features. The feature corresponding to the smallest weight in the new classifier is eliminated. The order of elimination yields a particular ranking. By convention, the last feature to be eliminated is ranked first. Chunks of genes were eliminated at a time. At the first iteration, the number of genes which is the closest power of 2 were reached. At subsequent iterations, half of the remaining genes were eliminated. Nested subsets of genes of increasing informative density were obtained.

The quality of these subsets of genes was then assessed by training various classifiers, including a regular SVM, the Golub et al classifier, and Fisher's linear discriminant (see e.g. (Duda, 1973)). An SVM trained after projecting the data along the first principal component of the training examples was also used. This amounts to setting a simple bias value, which was placed at the center of gravity of the two extreme examples of either class, weighted by the number of examples per class. This classifier was called a "reduced-capacity-SVM" ("RC-SVM").

Figure 23A:
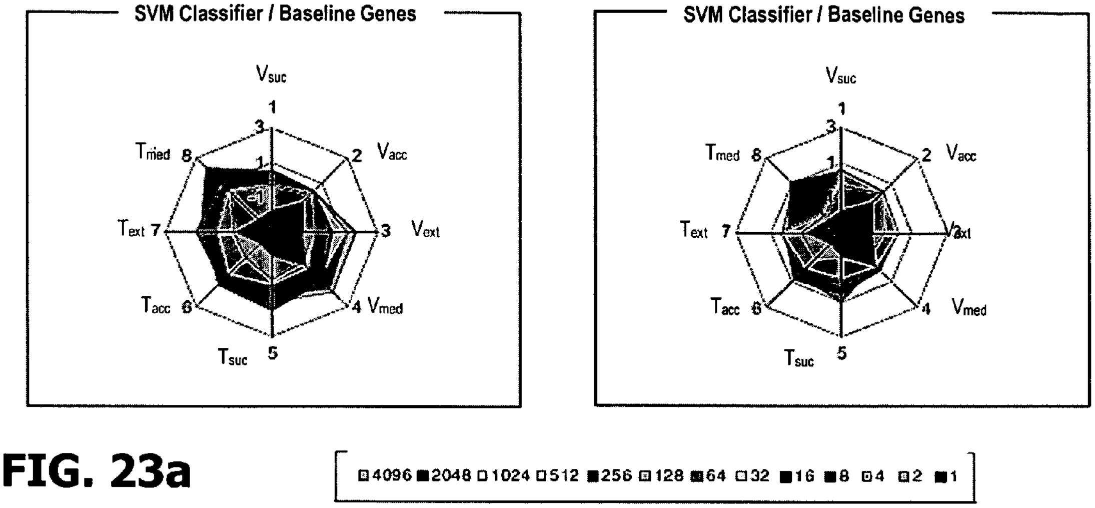
FIGS. 23*a* and 23*b* show the performance comparison between SVMs and the baseline method for leukemia data, where
Figure 23B:
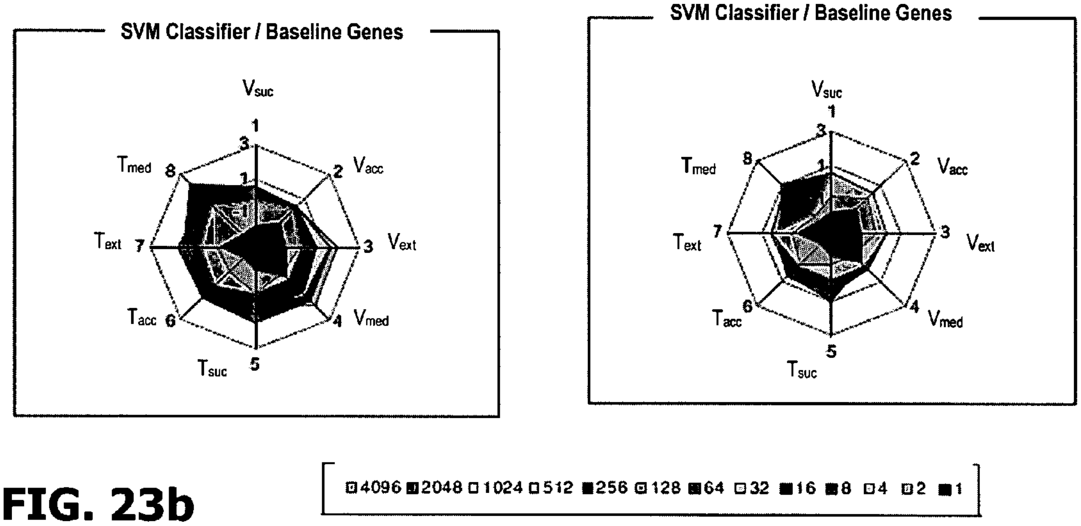

The various classifiers that were tried did not yield significantly different performance. The results of the classifier of Golub, 1999 and the reduced-capacity-SVM were reported herein. Several cross tests were performed with the baseline method to compare gene sets and classifiers. See FIG. 23*a*, which shows SVMs trained on SVM-selected genes or on baseline genes and FIG. 23*b*, which shows a baseline classifier trained on SVM-selected genes or on baseline genes. Classifiers have been trained with subsets of genes selected with SVMs and with the baseline method on the training set of the Leukemia data. The number of genes is color coded and indicated in the legend. The quality indicators are plot radially: channel 1–4=cross-validation results with the leave-one-out method; channels 5–8=test set results; suc=success rate; acc=acceptance rate; ext=extremal margin; med=median margin. The coefficients have been rescaled such that the average value of each indicator has zero mean an variance 1 across all four plots. For each classifier, the larger the colored area, the better the classifier. The figure shows that there is no significant difference between classifier performance on this data set, but there is a significant difference between the gene selections.

In Table 17, the best results obtained on the test set for each combination of gene selection and classification method are summarized. The classifiers give identical results, given a gene selection method. In contrast, the SVM selected genes yield consistently better performance than the baseline genes for both classifiers. The significance of the difference was tested with the statistical equation used herein.

Whether SVM or baseline classifier, SVM genes were better with 84.1% confidence based on test error rate and 99.2% based on the test rejection rate.

TABLE 17

Best classifier on test data (Leukemia data).

| Genes Classifier | # genes | Error # | Reject # |
|---|---|---|---|
| | SVM | | |
| SVM | 8, 16 | 0 | 0 |
| Baseline | 64 | 0 | 0 |
| | Baseline | | |
| SVM | 64 | 1 | 6 |
| Baseline | 64 | 1 | 6 |

The performance of the classifiers performing best on test data are reported. For each combination of SVM or Baseline genes and SVM or Baseline classifier, the corresponding number of genes, the number of errors and the number of rejections are shown in the table. The patient id numbers are shown in bracket.

To compare the top ranked genes, the fraction of common genes in the SVM selected subsets and the baseline subsets (Table 18) were computed. At the optimum number of 16 genes or less, at most 25% of the genes were common.

TABLE 18

Fraction of common genes between the sets selected with the baseline method and SVM recursive gene elimination (Leukemia data).

| Number of genes | Fraction of common Genes (percent) |
|---|---|
| All 7129 | 100 |
| 4096 | 71 |
| 2048 | 60 |
| 1024 | 55 |
| 512 | 40 |
| 256 | 39 |
| 128 | 32 |
| 64 | 33 |
| 32 | 28 |
| 16 | 19 |
| 8 | 25 |
| 4 | 25 |
| 2 | 0 |
| 1 | 0 |

The fraction of common genes decreases approximately exponentially as a function of the number of genes (linearly in a log scale). Only 19% of the genes were common at the optimum SVM gene set number 16.

Figure 24A:
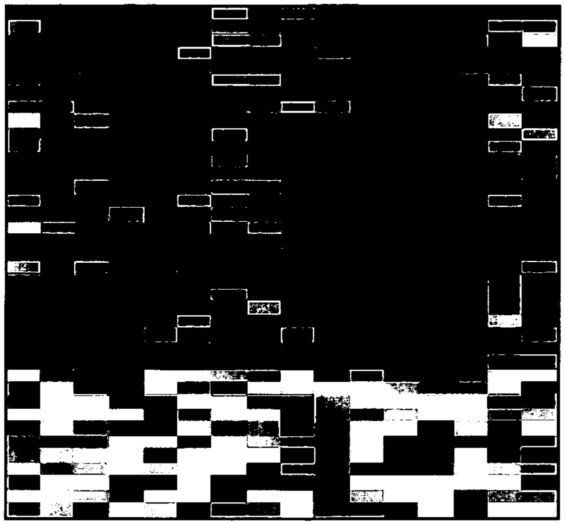
FIGS. 24*a*–24*d* show the best set of 16 genes for the leukemia data.
Figure 24B:
Figure 24C:
Figure 24D:

FIGS. 24*a–d* show the best set of 16 genes for the leukemia data. In the matrices of FIGS. 24*a* and 24*c*, the columns represent different genes and the lines (rows) different patients from the training set. The 27 top lines are ALL patients and the 11 bottom lines are AML patients. The gray shading indicates gene expression: the lighter the stronger. FIG. 24*a* shows SVM best 16 genes. Genes are ranked from left to right, the best one at the extreme left. All the genes selected are more AML correlated. FIG. 24*b* shows the weighted sum of the 16 SVM genes used to make the classification decision. A very clear ALL/AML separation is shown. FIG. 24*c* shows baseline method 16 genes. The method imposes that half of the genes are AML correlated and half are ALL correlated. The best genes are in the middle. FIG. 24*d* shows the weighted sum of the 16 baseline genes used to make the classification decision. The separation is still good, but not as good as the SVM separations.

FIGS. 24*a* and 24*c* show the expression values for the patients in the training set of the 16 gene subsets. At first sight, the genes selected by the baseline method looked a lot more orderly. This was because they were strongly correlated with either AML or ALL. There was a lot of redundancy in this gene set. In essence, all the genes carried the same information. Conversely, the SVM selected genes carrying complementary information. This was reflected in the output of the decision function (FIGS. 24*b* and 24*d*) which was a weighted sum of the 16 gene expression values. The SVM output more clearly separated AML patients from ALL patients. Tables 19 and 20 list the genes that were selected by the two methods.

TABLE 19

Top ranked 16 SVM genes (Leukemia data).

| Rk | GAN | Description | Correlation |
|---|---|---|---|
| 1 | U50136-rnal-at | Leukotriene C4 synthase (LTC4S) gene | AML |
| 2 | X95735-at | Zyxin | AML |
| 3 | M27891-at | CST3 Cystatin C (amyloid angiopathy and cerebral hemorrhage) | AML |
| 4 | M23197-at | CD33 antigen (differentiation antigen) | AML |
| 5 | M19507-at | MPO Myeloperoxidase | AML |
| 6 | M68891-at | GATA2 GATA-binding protein 2 | AML |
| 7 | U63289-at | RNA-binding protein CUG-BP/hNab50 (NAB50) mRNA | AML |
| 8 | M20902-at | APOC1 Apolipoprotein CI | AML |
| 9 | L36847-at | GB DEF = (clone p17/90) rearranged iduronate-2-sulphatase homologue gene | AML |
| 10 | Y00339-s-at | CA2 Carbonic anhydrase II | AML |
| 11 | X70297-at | CHRNA7 Cholinergic receptor, nicotinic, alpha polypeptide 7 | AML |
| 12 | D49950-at | Liver mRNA for interferon-gamma inducing factor(IGIF) | AML |
| 13 | M98399-s-at | CD36 CD36 antigen (collagen type I receptor, thrombospondin receptor) | AML |
| 14 | U43292-at | MDS1B (MDS1) mRNA | AML |
| 15 | M22960-at | PPGB Protective protein for beta-galactosidase (galactosialidosis) | AML |
| 16 | Y07604-at | Nucleoside-diphosphate kinase | AML |

Rk = rank.
GAN = Gene Accession Number.
Correlation = gene correlates most with the class listed.
The genes were obtained by recursively eliminating the least promising genes. Nested subsets of genes are obtained.

TABLE 20

Top ranked 16 baseline genes (Leukemia data).

| Rk | GAN | Correlation | Rk | GAN | Correlation |
|---|---|---|---|---|---|
| 1 | U22376-cds2-s-at | ALL | 1 | M55150-at | AML |
| 2 | X59417-at | ALL | 2 | U50136-rna1-at | AML |
| 3 | U05259-rna1-at | ALL | 3 | X95735-at | AML |
| 4 | M92287-at | ALL | 4 | M16038-at | AML |
| 5 | X74262-at | ALL | 5 | M23197-at | AML |
| 6 | L13278-at | ALL | 6 | M84526-at | AML |
| 7 | M31211-s-at | ALL | 7 | Y12670-at | AML |
| 8 | U09087-s-at | ALL | 8 | U82759-at | AML |

GAN = Gene Accession Number.
Correlation = gene correlates most with the class listed.
The 8 genes on the left correlate most with ALL and the 8 genes on the right with AML. The top ones are thebest candidates. Golub et al mixed equal proportions of ALL-correlated and AML-correlated genes in their experiments.

An Optimum Subset of Genes Can Be Predicted

The problem of predicting an optimum subset of genes was addressed. The criterion defined in the equation below derived from training examples only was used.

$$C=Q-2\epsilon(d)$$

Whether the predicted gene subset performed best on the test set was checked. The tests were carried out using SVM-RFE. The number of features was reduced progressively by a factor of two at every iteration. An SVM classifier was trained on all the intermediate subsets found.

Figure 25:
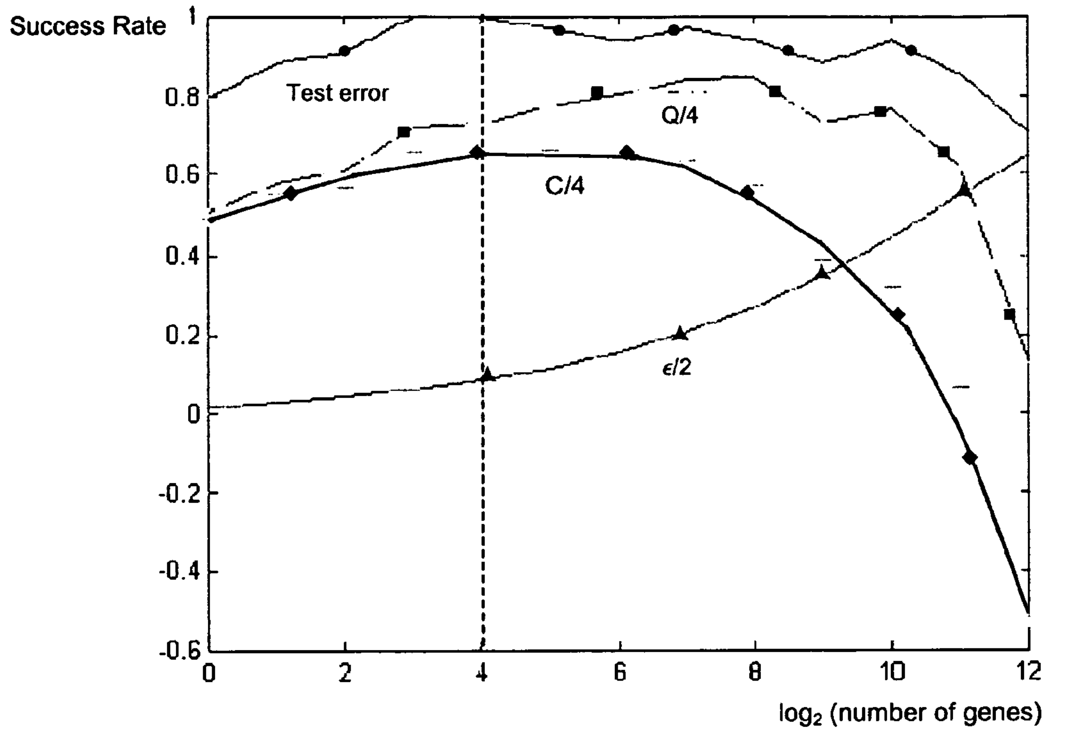
FIG. 25 shows the selection of an optimum number of genes for leukemia data.

As shown in FIG. 25, an optimum number of 16 genes was found. The number of genes selected by recursive gene elimination with SVMs was varied. The description of the lines of the graph is as follows: Circle: error rate on the test set. Square: scaled quality criterion (Q/4). crosses: scaled criterion of optimality (C/4). Diamond curve: result of locally smoothing the C/4. Circle: scaled theoretical error bar ($\epsilon/2$). The curves are related by $C=Q-2\epsilon$. The dashed line indicates the optimum of the diamond curve, which is the theoretically predicted optimum, based on training data only: $2^4$=16 genes. Zero test error is obtained at this optimum.

The performance on the test set was also optimum at that value. The details of the results are reported in Table 21.

TABLE 21

SVM classifier trained on SVM genes obtained with the RFE method (Leukemia data).

| Num genes | 2ϵ | Q | C = Q − 2ϵ | Training set (38 samples) $V_{suc}$ | $V_{acc}$ | $V_{ext}$ | $V_{med}$ |
|---|---|---|---|---|---|---|---|
| 4096 | 2.59 | 0.50 | −2.09 | 0.82 | 0.05 | −0.67 | 0.30 |
| 2048 | 2.20 | 2.46 | 0.26 | 0.97 | 0.97 | 0.00 | 0.51 |
| 1024 | 1.78 | 3.07 | 1.29 | 1.00 | 1.00 | 0.41 | 0.66 |
| 512 | 1.40 | 2.94 | 1.54 | 0.97 | 0.97 | 0.20 | 0.79 |
| 256 | 1.08 | 3.37 | 2.29 | 1.00 | 1.00 | 0.59 | 0.79 |
| 128 | 0.82 | 3.36 | 2.54 | 1.00 | 1.00 | 0.56 | 0.80 |
| 64 | 0.62 | 3.20 | 2.59 | 1.00 | 1.00 | 0.45 | 0.76 |
| 32 | 0.46 | 3.10 | 2.64 | 1.00 | 1.00 | 0.45 | 0.65 |
| 16 | 0.34 | 2.91 | 2.57 | 1.00 | 1.00 | 0.25 | 0.66 |
| 8 | 0.24 | 2.87 | 2.63 | 1.00 | 1.00 | 0.21 | 0.66 |
| 4 | 0.17 | 2.45 | 2.28 | 0.97 | 0.97 | 0.01 | 0.49 |
| 2 | 0.11 | 2.32 | 2.20 | 0.97 | 0.95 | −0.02 | 0.42 |
| 1 | 0.06 | 2.03 | 1.97 | 0.92 | 0.84 | −0.19 | 0.45 |

| Num genes | 2ϵ | Q | C = Q − 2ϵ | Test set (34 samples) $T_{suc}$ | $T_{acc}$ | $T_{ext}$ | $T_{med}$ |
|---|---|---|---|---|---|---|---|
| 4096 | 2.59 | 0.50 | −2.09 | 0.71 | 0.09 | −0.77 | 0.34 |
| 2048 | 2.20 | 2.46 | 0.26 | 0.85 | 0.53 | −0.21 | 0.41 |
| 1024 | 1.78 | 3.07 | 1.29 | 0.94 | 0.94 | −0.02 | 0.47 |
| 512 | 1.40 | 2.94 | 1.54 | 0.88 | 0.79 | 0.01 | 0.51 |
| 256 | 1.08 | 3.37 | 2.29 | 0.94 | 0.91 | 0.07 | 0.62 |
| 128 | 0.82 | 3.36 | 2.54 | 0.97 | 0.88 | −0.03 | 0.46 |
| 64 | 0.62 | 3.20 | 2.59 | 0.94 | 0.94 | 0.11 | 0.51 |
| 32 | 0.46 | 3.10 | 2.64 | 0.97 | 0.94 | 0.00 | 0.39 |
| 16 | 0.34 | 2.91 | 2.57 | 1.00 | 1.00 | 0.03 | 0.38 |
| 8 | 0.24 | 2.87 | 2.63 | 1.00 | 1.00 | 0.05 | 0.49 |
| 4 | 0.17 | 2.45 | 2.28 | 0.91 | 0.82 | −0.08 | 0.45 |
| 2 | 0.11 | 2.32 | 2.20 | 0.88 | 0.47 | −0.23 | 0.44 |
| 1 | 0.06 | 2.03 | 1.97 | 0.79 | 0.18 | −0.27 | 0.23 |

The criterion of classifier selection C was the classifier quality Q minus the error bar ϵ. These quantitieswere computed based on training data only. The success rate (at zero rejection), the acceptance rate (at zero error),the extreme margin and the median margin were reported for the leave-one-out method on the 38 sample training set(V results) and the 34 sample test set (T results). Where the number of genes was 16 was the best classifier predictedby the locally smoothed C criterion calculated using training data only.

At the optimum, the SVM is 100% accurate on the test set, without any rejection.

Comparison results with the baseline system at the predicted optimum are shown in Table 22.

TABLE 22

Best classifier selected with criterion C (Leukemia data).

| Genes Classifier | # genes | Error # | Reject # |
|---|---|---|---|
| | SVM | | |
| SVM | 16 | 0{ } | 0{ } |
| Baseline | 16 | 2 | 3 |

TABLE 22-continued

Best classifier selected with criterion C (Leukemia data).

| Genes Classifier | # genes | Error # | Reject # |
|---|---|---|---|
| | Baseline | | |
| SVM | 8 | 3 | 5 |
| Baseline | 8 | 3 | 6 |

The performance of the classifiers corresponding to the optimum of criterion C, computed solely on the basis of training examples, were reported. For each combination of SVM or Baseline genes and SVM or Baseline classifier, the corresponding number of genes, the number of errors and the number of rejections are shown in the table.

The overall difference obtained between the SVM system (optimum SVM classifier trained on SVM features) and the baseline system (optimum baseline classifier trained on baseline features) was quite significant: 95.8% for the error rate and 99.2% for the rejection rate. From cross-test analysis, it was seen that these differences can be traced mostly to a better set of features rather than a better classifier.

The leukemia data was tested by running the gene selection method on the entire data set of 72 samples. The four top ranked genes are shown in Table 23.

TABLE 23

Top ranked genes (Leukemia data).

| Rk | Expression | GAN | Description | Possible function/relation to Leukemia |
|---|---|---|---|---|
| 4 | AML > ALL | U59632 | Cell division control related protein (hCDCrel-1) mRNA | hCDCrel-1 is a partner gene of MLL in some leukemias (Osaka, 1999). |
| 3 | AML > ALL | U82759 | GB DEF = Homeodomain protein HoxA9 mRNA | Hoxa9 collaborates with other genes to produce highly aggressive acute leukemic disease (Thorsteinsdottir, 1999). |
| 2 | ALL > AML | HG1612 | MacMarcks | Tumor necrosis factor-alpha rapidly stimulate Marcks gene transcription in human promyelocytic leukemia cells (Harlan, 1991). |
| 1 | AML > ALL | X95735 | Zyxin | Encodes a LIM domain protein localized at focal contacts in adherent erythroleukemia cells (Macalma, 1996). |

The entire data set of 72 samples was used to select genes with SVM RFE. Genes were ranked in order of increasing importance. The first ranked gene is the last gene left after all other genes have been eliminated.
Expression: ALL > AML indicates that the gene expression level is higher in most ALL samples;
AML > ALL indicates that the gene expression level is higher in most AML samples;
GAN: Gene Accession Number.
All the genes in this list have some plausible relevance to the AML vs. ALL separation.

The number of four genes corresponds to the minimum number of support vectors (5 in this case). All four genes have some relevance to leukemia cancer and can be used for discriminating between AML and ALL variants.

In this last experiment, the smallest number of genes that separate the whole data set without error is two. For this set of genes, there is also zero leave-one-out error. In contrast, Golub's method always yields at least one training error and one leave-one-out error. One training error can be achieved with a minimum of 16 genes and one leave-one-out error with a minimum of 64 genes.

EXAMPLE 3

Isolation of Genes Involved With Prostate Cancer

Using the methods disclosed herein, genes associated with prostate cancer were isolated. Various methods of treating and analyzing the cells, including SVM, were utilized to determine the most reliable method for analysis.

Tissues were obtained from patients that had cancer and underwent prostatectomy. They were processed according to a standard protocol of Affymetrix and gene expression values from 7129 probes on the Affymetrix Gene Chip were recorded for 67 tissues from 26 patients.

The samples collected included tissues from the Peripheral Zone (PZ); Central Zone (CZ) and Transition Zone (TZ). Each sample potentially consisted of four different cell types: Stomal cells (from the supporting tissue of the prostate, not participating in its function); Normal organ cells; Benign prostatic hyperplasia cells (BPH); Dysplasia cells (cancer precursor stage) and Cancer cells (of various grades indicating the stage of the cancer). The distribution of the samples in Table 24 reflects the difficulty of getting certain types of tissues:

TABLE 24

Distribution of samples.

| | Stroma | Normal | BPH | Dysplasia | Cancer G3 | Cancer G4 | G3 + G4 |
|---|---|---|---|---|---|---|---|
| PZ | 1 | 5 | | 3 | 10 | 24 | 3 |
| CZ | | 3 | | | | | |
| TZ | | | 18 | | | | |

It has been argued in the medical literature that TZ BPH could serve as a good reference for PZ cancer. The highest grade cancer (G4) is the most malignant. Part of these experiments are therefore directed towards the separation of BPH vs. G4.

Sample Preparation

Some of the cells were prepared using laser confocal microscopy (LCM which was used to eliminate as much of the supporting stromal cells as possible and provides purer samples.

Gene expression was assessed from the presence of mRNA in the cells. The mRNA is converted into cDNA and amplified, to obtain a sufficient quantity. Depending on the amount of mRNA that can be extracted from the sample, one or two amplifications may be necessary. The amplification process may distort the gene expression pattern. In the data set under study, either 1 or 2 amplifications were used. LCM data always required 2 amplifications. The treatment of the samples is detailed in Table 25.

TABLE 25

| | 1 amplification | 2 amplifications |
|---|---|---|
| No LCM | 33 | 14 |
| LCM | | 20 |

The end result of data extraction is a vector of 7129 gene expression coefficients.

Determination of Gene Expression Coefficients

Probe Pairs:

Gene expression measurements require calibration. A probe cell (a square on the array) contains many replicates of the same oligonucleotide (probe) that is a 25 bases long sequence of DNA. Each "perfect match" (PM) probe is designed to complement a reference sequence (piece of gene). It is associated with a "mismatch" (MM) probe that is identical except for a single base difference in the central position. The chip may contain replicates of the same PM probe at different positions and several MM probes for the same PM probe corresponding to the substitution of one of the four bases. This ensemble of probes is referred to as a probe set. The gene expression is calculated as:

$$\text{Average Difference}=1/\text{pair num } \Sigma_{prob\ set}(PM-MM)$$

Data Quality

If the magnitude of the probe pair values is not contrasted enough, the probe pair is considered dubious. Thresholds are set to accept or reject probe pairs. Affymetrix considers samples with 40% or over acceptable probe pairs of good quality. Lower quality samples can also be effectively used with the SVM techniques.

Preprocessing

A simple "whitening" was performed as preprocessing. This means that after preprocessing the data matrix resembles "white noise". In the original data matrix a line of the matrix represented the expression values of 7129 genes for a given sample (corresponding to a particular combination of patient/tissue/preparation method). A column of the matrix represented the expression values of a given gene across the 67 samples. Without normalization, neither the lines nor the columns can be compared. There are obvious offset and scaling problems. The samples were preprocessed to: normalize matrix columns; normalize matrix lines; and normalize columns again. Normalization consists of subtracting the mean and dividing by the standard deviation. A further normalization step was taken when the samples are split into a training set and a test set.

The mean and variance column-wise was computed for the training samples only. All samples (training and test samples) were then normalized by subtracting that mean and dividing by the standard deviation.

Assessment of the Quality of the Samples

Samples were evaluated to determine whether LCM data preparation yields more informative data than unfiltered tissue samples and whether arrays of lower quality contain useful information when processed using the SVM technique.

Two data sets were prepared, one for a given data preparation method (subset 1) and one for a reference method (subset 2). For example, method 1=LCM and method 2=unfiltered samples. Golub's linear classifiers were then trained to distinguish between cancer and normal cases using subset 1 and another classifier using subset 2. The classifiers were then tested on the subset on which they had not been trained (classifier 1 with subset 2 and classifier 2 with subset 1).

If classifier 1 performs better on subset 2 than classifier 2 on subset 1, it means that subset 1 contains more information to do the separation cancer vs. normal than subset 2.

The input to the classifier is a vector of n "features" that are gene expression coefficients coming from one microarray experiment. The two classes are identified with the symbols (+) and (−) with "normal" or reference samples belong to class (+) and cancer tissues to class (−). A training set of a number of patterns $\{x_1, x_2, \ldots x_k, xl\}$ with known class labels $\{y_1, y_2, \ldots y_k, \ldots yl\}$, $y_k \in \{-1,+1\}$, is given. The training samples are used to build a decision function (or discriminant function) D(x), that is a scalar function of an input pattern x. New samples are classified according to the sign of the decision function:

D(x)>0→x∈ class (+)

D(x)<0→x∈ class (−)

D(x)=0, decision boundary.

Decision functions that are simple weighted sums of the training patterns plus a bias are called linear discriminant functions.

$$D(x)=w \cdot x+b,$$

where w is the weight vector and b is a bias value.

In the case of Golub's classifier, each weight is computed as:

$$W_i=(\mu_i(+)-\mu_i(-))/(\sigma_i(+)+\sigma_i(-))$$

where ($\mu_i$ and $\sigma_i$ are the mean and standard deviation of the gene expression values of gene i for all the patients of class (+) or class (−), i=1, ... n. Large positive $w_i$ values indicate strong correlation with class (+) whereas large negative $w_i$ values indicate strong correlation with class (−). Thus the weights can also be used to rank the features (genes) according to relevance. The bias is computed as $b=-w \cdot \mu$, where $\mu=(\mu(+)+\mu(-))/2$.

Golub's classifier is a standard reference that is robust against outliers. Once a first classifier is trained, the magnitude of $w_i$ is used to rank the genes. The classifiers are then retrained with subsets of genes of different sizes, including the best ranking genes.

To assess the statistical significance of the results, ten random splits of the data including samples were prepared from either preparation method and submitted to the same method. This allowed the computation of an average and standard deviation for comparison purposes.

Importance of LCM Data Preparation

Tissue from the same patient was processed either directly (unfiltered) or after the LCM procedure, yielding a pair of micro-array experiments. This yielded 13 pairs, including: four G4; one G3+4;two G3; four BPH; one CZ (normal) and one PZ (normal).

For each data preparation method (LCM or unfiltered tissues), the tissues were grouped into two subsets:

Cancer=G4+G3 (7 cases)

Normal=BPH+CZ+PZ (6 cases).

Figure 26:
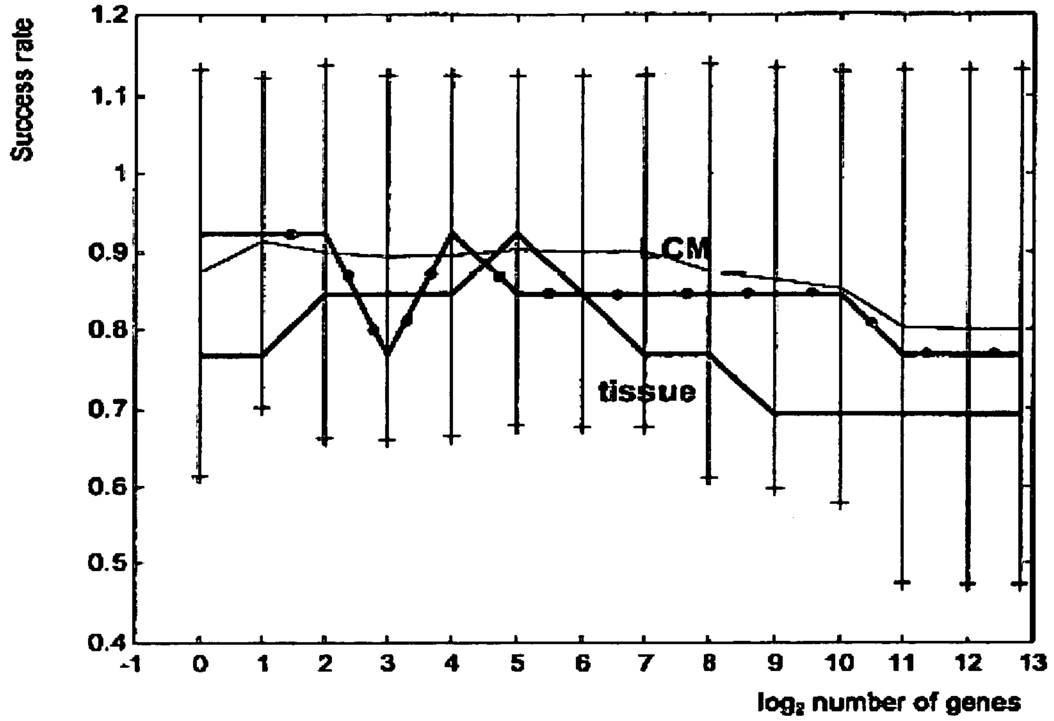
FIG. 26 is a plot showing the results based on LCM data preparation for prostate cancer analysis.

The results are shown in FIG. 26. The large error bars are due to the small size. However, there is an indication that LCM samples are better than unfiltered tissue samples. It is also interesting to note that the average curve corresponding to random splits of the data is above both curves. This is not surprising since the data in subset 1 and subset 2 are differently distributed. When making a random split rather than segregating samples, both LCM and unfiltered tissues are represented in the training and the test set and performance on the test set are better on average.

Importance of Array Quality as Measured by Affymetrix

The same methods were applied to determine whether microarrays with gene expressions rejected by the Affymetrix quality criterion contained useful information by focusing on the problem of separating BPH tissue vs. G4 tissue with a total of 42 arrays (18 BPH and 24 G4).

The Affymetrix criterion identified 17 good quality arrays, 8 BPH and 9 G4.

Two subsets were formed:

Subset 1="good" samples, 8 BPH+9 G4

Subset 2="mediocre" samples, 10 BPH+15 G4

For comparison, all of the samples were lumped together and 10 random subset 1 containing 8 BPH+9 G4 of any quality were selected. The remaining samples were used as subset 2 allowing an average curve to be obtained. Additionally the subsets were inverted with training on the "mediocre" examples and testing on the "good" examples.

When the mediocre samples are trained, perfect accuracy on the good samples is obtained, whereas training on the good examples and testing on the mediocre yield substantially worse results.

All the BPH and G4 samples were divided into LCM and unfiltered tissue subsets to repeat similar experiments as in the previous Section:

Subset1=LCM samples (5 BPH+6 LCM)

Subset2=unfiltered tissue samples (13 BPH+18 LCM)

There, in spite of the difference in sample size, training on LCM data yields better results. In spite of the large error bars, this is an indication that the LCM data preparation method might be of help in improving sample quality.

BPH vs. G4

The Affymetrix data quality criterion were irrelevant for the purpose of determining the predictive value of particular genes and while the LCM samples seemed marginally better than the unfiltered samples, it was not possible to determine a statistical significance. Therefore, all samples were grouped together and the separation BHP vs. G4 with all 42 samples (18 BPH and 24 G4) was performed.

To evaluate performance and compare Golub's method with SVMs, the leave-one-out method was used. The fraction of successfully classified left-out examples gives an estimate of the success rate of the various classifiers.

Figure 27:
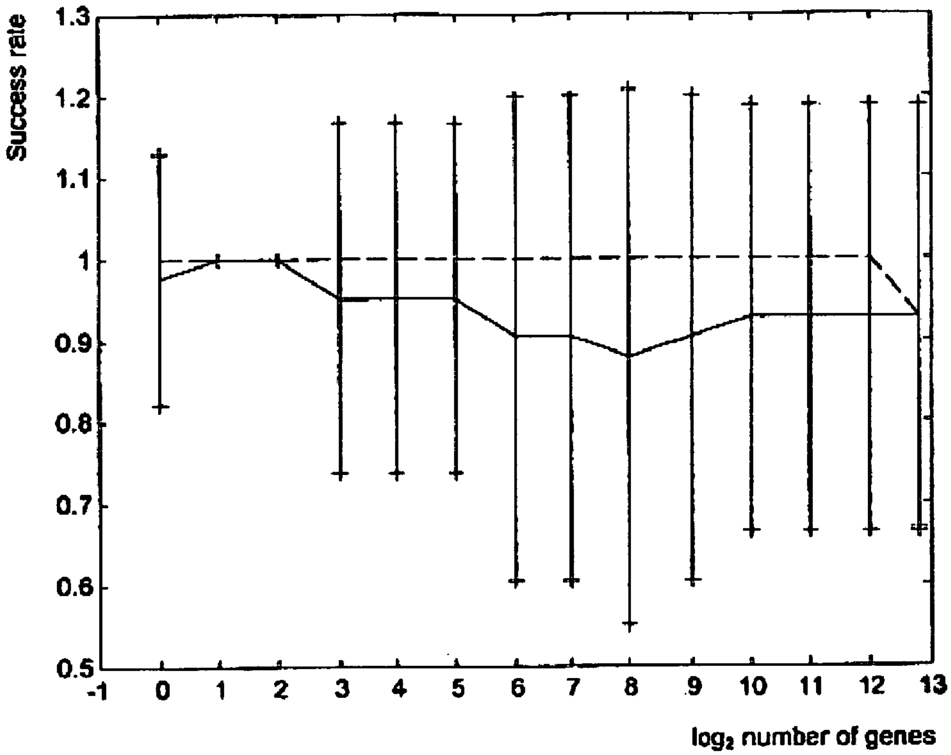
FIG. 27 is a plot graphically comparing SVM-RFE of the present invention with leave-one-out classifier for prostate cancer.

In this procedure, the gene selection process was run 41 times to obtain subsets of genes of various sizes for all 41 gene rankings. One classifier was then trained on the corresponding 40 genes for every subset of genes. This leave-one-out method differs from the "naive" leave-one-out that consists of running the gene selection only once on all 41 examples and then training 41 classifiers on every subset of genes. The naive method gives overly optimistic results because all the examples are used in the gene selection process, which is like "training on the test set". The increased accuracy of the first method is illustrated in FIG. 27. The method used in the figure is SVM-RFE and the classifier used is an SVM. All SVMs are linear with soft margin parameters C=100 and t=10"$^{14}$. The dashed line represents the "naive" leave-one-out (loo), which consists in running the gene selection once and performing loo for classifiers using subsets of genes thus derived, with different sizes. The solid line represents the more computationally expensive "true" loo, which consists in running the gene selection 41 times, for every left out example. The left out example is classified with a classifier trained on the corresponding 40 examples for every selection of genes. If f is the success rate obtained (a point on the curve), the standard deviation is computed as sqrt(f(1−f)).

Comparison Between SVMs and Golub's Method

Figure 28:
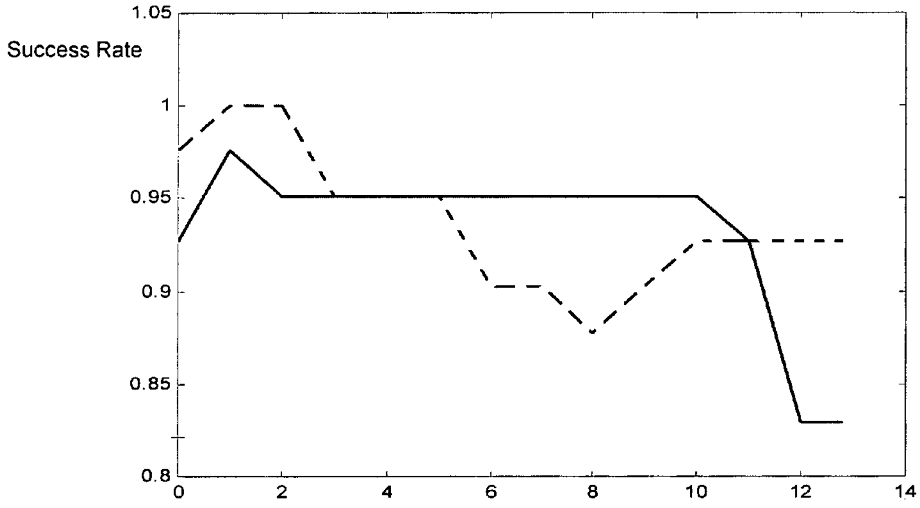
FIG. 28 graphically compares the Golub and SVM methods for prostate cancer.
Figure 29A:
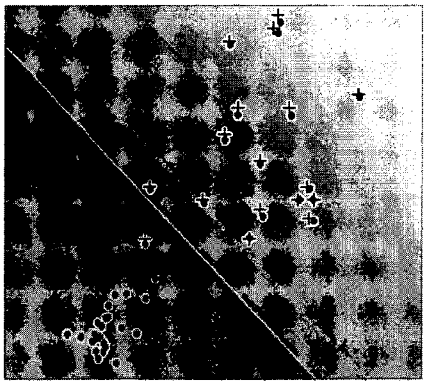
FIGS. 29*a* and 29*b* illustrate the decision functions obtained for Golub (FIG. 29*a*) and SVM methods (FIG. 29*b*) for the two best ranking genes.
Figure 29B:
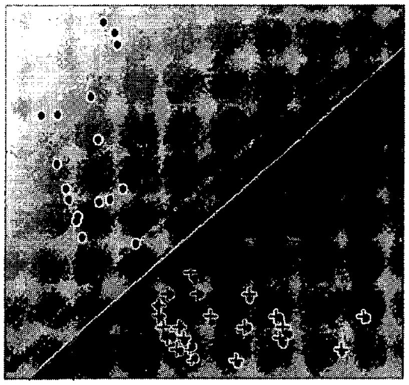

The "true" leave-one-out method was used to evaluate both Golub's method and SVMs. The results are shown in FIG. 28. SVMs outperform Golub's method for the small number of examples. However, the difference is not statistically significant in a sample of this size (1 error in 41 examples, only 85% confidence that SVMs are better). FIGS. 29*a* and 29*b* depict the decision functions obtained for the two best ranking genes with either method.

The gene selection was then run for both methods on all 41 samples. Many of the top ranking genes found were related to colon cancer as shown in a bibliographical search.

EXAMPLE 4

Analyzing Small Data sets with Multiple Features

Small data sets with large numbers of features present several problems. In order to address ways of avoiding data overfitting and to assess the significance in performance of multivariate and univariate methods, the samples from Example 3 which were classified by Affymetrix as high quality samples were further analyzed. The samples include 8 BPH and 9 G4 tissues. Each microarray recorded 7129 gene expression values. The methods described herein can use the ⅔ of the samples in the BHP, G4 subset which were considered of inadequate quality for use with standard methods.

The first method is used to solve a classical Machine Learning problem. If only a few tissue examples are used to select best separating genes, these genes are likely to separate well the training examples but perform poorly on new, unseen examples (test examples). Single-feature SVM, described herein, performs particularly well under these adverse conditions. The second method is used to solve a problem of classical statistics and requires a test that uses a combination of the McNemar criterion and the Wilcoxon test. This test allows the comparison of the performance of two classifers trained and tested on random splits of the data set into a training and a test set.

Gene Selection and Classification Methods

The methods of classifying data has been disclosed elsewhere and is repeated herein for clarity. The problem of classifying gene expression data can be formulated as a classical classification problem where the input is a vector, a "pattern" of n components called "features". F is the n-dimensional feature space. In the case of the problem at hand, the features are gene expression coefficients and patterns correspond to tissues. This is limited to two-class classification problems. The two classes are identified with the symbols (+) and (−). A training set of a number of patterns $\{x_1, x_2, \ldots x_k, \ldots x_p\}$ with known class labels $\{y_1, y_2, \ldots y_k, \ldots y_p\}$, $y_k \in \{-1,+1\}$, is given. The training set is usually a subset of the entire data set, some patterns being reserved for testing. The training patterns are used to build a decision function (or discriminant function) D(x), that is a scalar function of an input pattern x. New patterns (e.g. from the test set) are classified according to the sign of the decision function:

$D(x)<0 \rightarrow x \in$ class (−)

$D(x)>0 \rightarrow x \in$ class (+)

$D(x)=0$, decision boundary.

Decision functions that are simple weighted sums of the training patterns plus a bias are called linear discriminant functions.

$$D(x)=w \cdot x+b, \quad (1)$$

where w is the weight vector and b is a bias value.

A data set such as the one used in these experiments, is said to be "linearly separable" if a linear discriminant function can separate it without error. The data set under study is linearly separable. Moreover, there exist single features (gene expression coefficients) that alone separate the entire data set. This study is limited to the use of linear discriminant functions. A subset of linear discriminant functions are selected that analyze data from different points of view:

One approach used multivariate methods, which computed every component of the weight w on the basis of all input variables (all features), using the training examples. For multivariate methods, it does not make sense to intermix features from various rankings as feature subsets are selected for the complementarity of their features, not for the quality of the individual features. The combination is then in selecting the feature ranking that is most consistent with all other ranking, i.e. contains in its top ranking features the highest density of features that appear at the top of other feature rankings. Two such methods were selected:

LDA: Linear Discriminant Analysis, also called Fisher's linear discriminant (see e.g. (Duda, 73)). Fisher's linear discriminant is a method that seeks for w the direction of projection of the examples that maximizes the ratio of the between class variance over the within class variance. It is an "average case" method since w is chosen to maximally separate the class centroids.

SVM: The optimum margin classifier, also called linear Support Vector Machine (linear SVM). The optimum margin classifiers seeks for w the direction of projection of the examples that maximizes the distance between patterns of opposite classes that are closest to one another (margin). Such patterns are called support vector. They solely determine the weight vector w. It is an "extreme case" method as w is determined by the extremes or "borderline" cases, the support vectors.

A second approach, multiple univariate methods, was also used. Such methods computed each component $w_i$ of the weight vectors on the basis of the values that the single variable $x_i$ takes across the training set. The ranking indicates relevance of individual features. One method was to combine rankings to derive a ranking from the average weight vectors of the classifiers trained on different training sets. Another method was to first create the rankings from the weight vectors of the individual classifiers. For each ranking, a vector is created whose components are the ranks of the features. Such vectors are then averaged and a new ranking is derived from this average vector. This last method is also applicable to the combination of rankings coming from different methods, not necessarily based on the weights of a classifier. Two univariate methods, the equivalents of the multivariate methods were selected:

SF-LDA: Single Feature Linear Discriminant Analysis:

$$w_i=(\mu_i(+)-\mu_i(-))/sqrt(p(+)\sigma_i(+)^2+p(-)\sigma_i(-)^2) \quad (13)$$

SF-SVM: Single Feature Support Vector Machine:

$$w_i=(s_i(+)-s_i(-), \text{ if sign } (s_i(+)-s_i(-))=\text{sign}(\mu_i(+)-\mu_i(-)) \quad (14)$$

$w_i=0$ otherwise.

The parameters $\mu_i$ and $\sigma_i$ are the mean and standard deviation of the gene expression values of gene i for all the tissues of class (+) or class (−), i=1, . . . n. p(+) and p(−) are the number of examples of class (+) or class (−).

The single feature Fisher discriminant (SF-LDA) bears a lot of resemblance with the method of Golub et al (Golub, 1999). This last method computes the weights according to $w_i=(\mu_i(+)-\mu_i(-))/\sigma_i(+)+\sigma_i(-))$. The two methods yield similar results. Feature normalization played an important role for the SVM methods. All features were normalized by subtracting their mean and dividing by their standard deviation. The mean and standard deviation are computed on training examples only. The same values are applied to test examples. This is to avoid any use of the test data in the learning process.

The bias value can be computed in several ways. For LDA methods, it is computed as: b=−(m(+)+m(−))/2, where m(+)=w·μ(+) and m(−)=w·μ(−). This way, the decision boundary is in the middle of the projection of the class means on the direction of w. For SVMs, it is computed as b=−(s(+)+s(−))/2, where s(+)=min w·x(+) and s(−)=max w·x(−), the minimum and maximum being taken over all training examples x(+) and x(−) in class (+) and (−) respectively. This way, the decision boundary is in the middle of the projection of the support vectors of either class on the direction of w, that is in the middle of the margin.

Gene Selection Methods

The magnitude of the weight vectors of trained classifiers was used to rank features (genes). Intuitively, those features with smallest weight contribute least to the decision function and therefore can be spared.

For univariate methods, such ranking corresponds to ranking features (genes) individually according to their relevance. Subsets of complementary genes that together separate best the two classes cannot be found with univariate methods.

For multivariate methods, each weight w; is a function of all the features of the training examples. Therefore, removing one or several such features affects the optimality of the decision function. The decision function must be recomputed after feature removal (retraining). Recursive Feature Elimination (RFE), the iterative process alternating between two steps is: (1) removing features and (2) retraining, until all features are exhausted. For multiple univariate methods, retraining does not change the weights and is therefore omitted. The order of feature removal defines a feature ranking or, more precisely, nested subsets of features. Indeed, the last feature to be removed with RFE methods may not be the feature that by itself best separates the data set. Instead, the last 2 or 3 features to be removed may form the best subset of features that together separate best the two classes. Such a subset is usually better than a subset of 3 features that individually rank high with a univariate method.

Statistical Significance of Performance Difference

For very small data sets, it is particularly important to assess the statistical significance of the results. Assume that the data set is split into 8 examples for training and 9 for testing. The conditions of this experiment often results in a 1 or 0 error on the test set. A z-test with a standard definition of "statistical significance" (95% confidence) was used. For a test set of size t=9 and a true error rate p=1/9, the difference between the observed error rate and the true error rate can be as large as 17%. The formula $\epsilon=z_\eta$sqrt(p(1−p)/t), where $z_\eta$=sqrt(2)erfinv(−2(η−0.5)), η=0.05, was used, where erfinv is the inverse error function, which is tabulated.

The error function is defined as:

$$\text{erf}(x) = \int_0^x \exp(-t^2)\,dt.$$

This estimate assumes i.i.d. errors (where the data used in training and testing were independently and identically distributed), one-sided risk and the approximation of the Binomial law by the Normal law. This is to say that the absolute performance results (question 1) should be considered with extreme care because of the large error bars.

In contrast, it is possible to compare the performance of two classification systems (relative performance, question 2) and, in some cases, assert with confidence that one is better than the other. One of the most accurate tests is the McNemar test, which proved to be particularly well suited to comparing classification systems in a recent benchmark. The McNemar test assesses the significance of the difference between two dependent samples when the variable of interest is a dichotomy. With confidence (1-ii) it can be accepted that one classifier is better than the other, using the formula:

$$(1-\eta)=0.5+0.5erf(z/sqrt(\mathbf{2})) \quad (15)$$

where z=εt/sqrt(v); t is the number of test examples, v is the total number of errors (or rejections) that only one of the two classifiers makes, ε is the difference in error rate, and erf is the error function $$\text{erf}(x) = \int_0^x \exp(-t^2)\,dt.$$

This assumes i.i.d. errors, one-sided risk and the approximation of the Binomial law by the Normal law. The comparison of two classification systems and the comparison of two classification algorithms need to be distinguished. The first problem addresses the comparison of the performance of two systems on test data, regardless of how these systems were obtained (they might have not been obtained by training). This problem arises, for instance, in the quality comparison of two classification systems packaged in medical diagnosis tests ready to be sold.

A second problem addresses the comparison of the performance of two algorithms on a given task. It is customary to average the results of several random splits of the data into a training set and a test set of a given size. The proportion of training and test data are varied and results plotted as a function of the training set size. Results are averaged over s=20 different splits for each proportion (only 17 in the case of a training set of size 16, since there are only 17 examples). To compare two algorithms, the same data sets to train and test are used with the two algorithms, therefore obtaining paired experiments. The Wilcoxon signed rank test is then used to evaluate the significance of the difference in performance. The Wilcoxon test tests the null hypothesis two treatments applied to N individuals do not differ significantly. It assumes that the differences between the treatment results are meaningful. The Wilcoxon test is applied as follows: For each paired test i, i=1, . . . s, the difference $\epsilon_i$ in error rate of the two classifiers trained is computed in the two algorithms to be compared. The test first orders the absolute values of $\epsilon_i$ the from the least to the greatest. The quantity T to be tested is the sums the ranks of the absolute values of $\epsilon_i$ over all positive $\epsilon_i$. The distribution of T can easily be calculated exactly of be approximated by the Normal law for large values of s. The test could also be applied by replacing $\epsilon_i$ by the normalized quantity $\epsilon_i$/sqrt($v_i$) used in (15) for the McNemar test, computed for each paired experiment. In this study, the difference in error rate $\epsilon_i$ is used. The p value of the test is used in the present experiments: the probability of observing more extreme values than T by chance if $H_0$ is true: Proba(TestStatistic>Observed T).

If the p value is small, this sheds doubt on $H_0$, which states that the medians of the paired experiments are equal. The alternative hypothesis is that one is larger than the other.

Preprocessing

The normalized arrays as provided by Affymetrix were used. No other preprocessing is performed on the overall data set. However, when the data was split into a training set and a test set, the mean of each gene is subtracted over all training examples and divided by its standard deviation. The same mean and standard deviation are used to shift and scale the test examples. No other preprocessing or data cleaning was performed.

It can be argued that genes that are poorly contrasted have a very low signal/noise ratio. Therefore, the preprocessing that divides by the standard deviation just amplifies the noise. Arbitrary patterns of activities across tissues can be obtained for a given gene. This is indeed of concern for unsupervised learning techniques. For supervised learning techniques however, it is unlikely that a noisy gene would by chance separate perfectly the training data and it will therefore be discarded automatically by the feature selection algorithm. Specifically, for an over-expressed gene, gene expression coefficients took positive values for G4 and negative values for BPH. Values are drawn at random with a probability '/2 to draw a positive or negative value for each of the 17 tissues. The probability of drawing exactly the right signs for all the tissues is ('/2)". The same value exists for an under-expressed gene (opposite signs). Thus the probability for a purely noisy gene to separate perfectly all the BPH from the G4 tissues is p=2(%2)"=1.5.10–5. There are m=7129–5150=1979 presumably noisy genes. If they were all just pure noise, there would be a probability $(1-p)_m$ that none of them separate perfectly all the BPH from the G4 tissues. Therefore a probability 1–(1–p) m–3% that at least one of them does separate perfectly all the BPH from the G4 tissues.

For single feature algorithms, none of a few discarded genes made it to the top, so the risk is irrelevant. For SVM and LDA, there is a higher risk of using a "bad" gene since gene complementarity is used to obtain good separations, not single genes. However, in the best gene list, no gene from the discarded list made it to the top.

Data Splits

Simulations resulting from multiple splits of the data set of 17 examples (8 BPH and 9 G4) into a training set and a test set were run. The size of the training set is varied. For each training set drawn, the remaining of the data are used for testing. For number of training examples greater than 4 and less than 16, 20 training sets were selected at random. For 16 training examples, the leave-one-out method was used, in that all the possible training sets obtained by removing 1 example at a time (17 possible choices) were created. The test set is then of size 1. Note that the test set is never used as part of the feature selection process, even in the case of the leave-one-out method.

For 4 examples, all possible training sets containing 2 examples of each class (2 BPH and 2 G4), were created and 20 of them were selected at random.

For SVM methods, the initial training set size is 2 examples, one of each class (1 BPH and 1 G4). The examples of each class are drawn at random. The performance of the LDA methods cannot be computed with only 2 examples, because at least 4 examples (2 of each class) are required to compute intraclass standard deviations. The number of training examples are incremented by steps of 2.

Learning Curves and Feature Selection Curves

The curves presented in this section are obtained with the following procedure (Table 26):

Table 26: Experimental procedure.

1) For each feature selection/classification method (SVM, SF-SVM, LDA, SF-LDA):

2) For each number of training examples ((2), 4, 6, 8, 10, 12, 14, 16):

3) For each particular drawing of the training/test split (20 drawings, in general):

4) Compute the feature subset ranking (using the training examples only).

5) For each subset of genes of size 0, 1, 2 . . . in a log2 scale:

6) Compute the weights of the classifier using the training examples.

7) Compute the performance of the classifier on the test examples. END

Overall, SF-SVM performs best, with the following four quadrants distinguished.

(Table 27):

TABLE 27

Best performing methods of feature selection/classification.

| Num. Ex. | small | large |
|---|---|---|
| Num. Genes | | |
| Large | SF-SVM is best. Single feature methods (SF-SVM and SF-LDA) outperform multivariate methods (SVM and LDA). | Multivariate methods may be best. The differences are not statistically significant. |
| Small | SF-LDA performs best. LDA performs worst and single feature methods outperform multivariate methods. | LDA performs worst. It is unclear whether single feature methods perform better. SF-SVM may have an advantage. |

The choice of $w_i$=0 for negative margin genes in SF-SVM (Equation 3) corresponds to an implicit pre-selection of genes and partially explains why SF-SVM performs do well for large numbers of genes. In fact, no genes are added beyond the total number of genes that separate perfectly G4 from BPH.

Final Run on All the Examples

All methods were re-run using the entire data set. The top ranked genes are presented in Tables 28–31. Having determined that the SVM method provided the most compact set of features to achieve 0 leave-one-out error and that the SF-SVM method is the best and most robust method for small numbers of training examples, the top genes found by these methods were researched in the literature. Most of the genes have a connection to cancer or more specifically to prostate cancer.

TABLE 28

Top ranked genes for SF LDA using 17 best BHP/G4.

| Rank | GAN | EXP | Description |
|---|---|---|---|
| 10 | X83416 | −1 | *H. sapiens* PrP gene |
| 9 | U50360 | −1 | Human calcium calmodulin-dependent protein |
| 8 | U35735 | −1 | Human RACH1 (RACH1) mRNA |
| 7 | M57399 | −1 | Human nerve growth factor (HBNF-1) mRNA |
| 6 | M55531 | −1 | Human glucose transport-like 5 (GLUT5) mRNA |
| 5 | U48959 | −1 | Human myosin light chain kinase (MLCK) |
| 4 | Y00097 | −1 | Human mRNA for protein p68 |
| 3 | D10667 | −1 | Human mRNA for smooth muscle myosin heavy |
| 2 | L09604 | −1 | *Homo sapiens* differentiation-dependent A4 protein |
| 1 | HG1612-HT1612 | 1 | McMarcks |

GAN = Gene Acession Number.
EXP = Expression (−1 = underexpressed in cancer (G4) tissues, +1 = overexpressed in cancer tissues).

TABLE 29

Top ranked genes for LDA using 17 best BHP/G4.

| Rank | GAN | EXP | Description |
|---|---|---|---|
| 10 | J03592 | 1 | Human ADP/ATP translocase mRNA |
| 9 | U40380 | 1 | Human presenilin I-374 (AD3-212) mRNA |
| 8 | D31716 | −1 | Human mRNA for GC box bindig protein |
| 7 | L24203 | −1 | *Homo sapiens* ataxia-telangiectasia group D |
| 6 | J00124 | −1 | *Homo sapiens* 50 kDa type I epidermal keratin |
| 5 | D10667 | −1 | Human mRNA for smooth muscle myosin heavy |
| 4 | J03241 | −1 | Human transforming growth factor-beta 3 (TGF-beta3) |
| 3 | 017760 | −1 | Human laminin S B3 chain (LAMB3) gene |
| 2 | X76717 | −1 | *H. sapiens* MT-11 mRNA |
| 1 | X83416 | −11 | *H. sapiens* PrP gene |

TABLE 30

Top ranked genes for SF SVM using 17 best BHP/G4.

| Rank | GAN | EXP | Description |
|---|---|---|---|
| 10 | X07732 | 1 | Human hepatoma mRNA for serine protease hepsin |
| 9 | J03241 | −1 | Human transforming growth factor-beta 3 (TGF- |
| 8 | X83416 | −1 | *H. sapiens* PrP gene |
| 7 | X14885 | −1 | *H. sapiens* gene for transforming growth factor-beta |
| 6 | U32114 | −1 | Human caveolin-2 mRNA |
| 5 | M16938 | 1 | Human homeo-box c8 protein |
| 4 | L09604 | −1 | *Homo sapiens* differentiation-dependent A4 protein MRNA |
| 3 | Y00097 | −1 | Human mRNA for protein p68 |
| 2 | D88422 | −1 | Human DNA for cystatin A |
| 1 | U35735 | −1 | Human RACH1 (RACH1) mRNA |

TABLE 31

Top ranked genes for SVM using 17 best BHP/G4.

| Rank | GAN | EXP | Description |
|---|---|---|---|
| 10 | X76717 | −1 | *H. sapiens* MT-11 mRNA |
| 9 | U32114 | −1 | Human caveolin-2 mRNA |
| 8 | X85137 | 1 | *H. sapiens* mRNA for kinesin-related protein |
| 7 | D83018 | −1 | Human mRNA for nel-related protein 2 |
| 6 | D10667 | −1 | Human mRNA for smooth muscle myosin heavy |
| 5 | M16938 | 1 | Human homeo box c8 protein |
| 4 | L09604 | −1 | *Homo sapiens* differentiation-dependent A4 protein |
| 3 | HG1612 | 1 | McMarcks |
| 2 | M10943 | −1 | Human metallothionein-If gene (hMT-If) |
| 1 | X83416 | −1 | *H. sapiens* PrP gene |

Results on 42 Tissues

Using the "true" leave-one-out method (including gene selection and classification), the experiments indicated that 2 genes should suffice to achieve 100% prediction accuracy. The two top genes were therefore more particularly researched in the literature. The results are summarized in Table 33. It is interesting to notice that the two genes selected appear frequently in the top 10 lists of Table 28–31 obtained by training only on the 17 best genes.

TABLE 32

Top ranked genes for SVM using all 42 BHP/G4.

| Rank | GAN | EXP | Description |
|---|---|---|---|
| 10 | X87613 | −1 | *H. sapiens* mRNA for skeletal muscle abundant |
| 9 | X58072 | −1 | Human hGATA3 mRNA for trans-acting T-cell |
| 8 | M33653 | −1 | Human alpha-2 type IV collagen (COL4A2) |
| 7 | S76473 | 1 | trkB [human brain mRNA] |
| 6 | X14885 | −1 | *H. sapiens* gene for transforming growth factor-beta |
| 5 | S83366 | −1 | region centromeric to t(12;17) brakepoint |
| 4 | X15306 | −1 | *H. sapiens* NF-H gene |
| 3 | M30894 | 1 | Human T-cell receptor Ti rearranged gamma-chain |
| 2 | M16938 | 1 | Human homeo box c8 protein |
| 1 | U35735 | −1 | Human RACH1 (RACH1) mRNA |

TABLE 33

Findings for the top 2 genes found by SVM using all 42 BHP/G4.

| GAN | Synonyms | Possible function/link to prostate cancer |
|---|---|---|
| M16938 | HOXC8 | Hox genes encode transcriptional regulatory proteins that are largely responsible for establishing the body plan of all metazoan organisms. There are hundreds of papers in PubMed reporting the role of HOX genes in various cancers. HOXC5 and HOXC8 expression are selectively turned on in human cervical cancer cells compared to normal keratinocytes. Another homeobox gene (GBX2) may participate in metastatic progression in prostatic cancer. Another HOX protein (hoxb-13) was identified as an androgen-independent gene expressed in adult mouse prostate epithelial cells. The authors indicate that this provides a new potential target for developing therapeutics to treat advanced prostate cancer |
| U35735 | Jk<br>Kidd<br>RACH1<br>RACH2<br>SLC14A1<br>UT1<br>UTE | Overexpression of RACH2 in human tissue culture cells induces apoptosis. RACH1 is downregulated in breast cancer cell line MCF-7. RACH2 complements the RAD1 protein. RAM is implicated in several cancers. Significant positive lod scores of 3.19 for linkage of the Jk (Kidd blood group) with cancer family syndrome (CFS) were obtained. CFS gene(s) may possibly be located on chromosome 2, where Jk is located. |

Taken together, the expression of these two genes is indicative of the severity of the disease (Table 34).

TABLE 34

Severity of the disease as indicated by the top 2 ranking genes selected by SVMs using all 42 BPH and G4 tissues.

| | HOXC8 Underexpressed | HOXC8 Overexpressed |
|---|---|---|
| RACH1 Overexpressed | Benign | N/A |
| RACH1 Underexpressed | Grade 3 | Grade 4 |

F) Methodology Comparison

T-test

One of the reasons for choosing SF-LDA as a reference method to compare SVMs with is that SF-LDA bears a lot of resemblance with one of the gene ranking techniques used by Affymetrix. Indeed, Affymetrix uses that pvalue of the T-test to rank genes. While not wishing to be bound by any particular theory, it is believed that the null hypothesis to be tested is the equality of the two expected values of the expressions of a given gene for class (+) BPH and class (−) G4. The alternative hypothesis is that the one with largest average value has the largest expected value. The pvalue is a monotonically varying function of the quantity to be tested:

$$T_i=(\mu_i(+)-\mu_i(-))/(\mu_i sqrt(1/p(+)+1/p(-))$$

where $(\mu_i(+)-\mu_i(-)$ are the means the gene expression values of gene i for all the tissues of class (+) or class (−), i=1, . . . n. p(+) and p(−) are the number of examples of class (+) or class (−); $\sigma_i^2=(p(+)\sigma_i(+)^2+p(-)\ \sigma_i(-)_2)/p$ is the intra-class variance. Up to a constant factor, which does not affect the ranking, $T_i$ is the same criterion as $w_i$ in Equation (2) used for ranking features by SF-LDA.

It was pointed out by Affymetrix that the pvalue may be used as a measure of risk of drawing the wrong conclusion that a gene is relevant to prostate cancer, based on examining the differences in the means. Assume all the genes with pvalue lower than a threshold α are selected. At most a fraction α of those genes should be bad choices. However, this interpretation is not quite accurate since the gene expression values of different genes on the same chip are not independent experiments. Additionally, this assumes the equality of the variances of the two classes, which should be tested.

There are variants in the definition of $T_i$ that may account for small differences in gene ranking. Another variant of the method is to restrict the list of genes to genes that are overexpressed in all G4 tissues and underexpressed in all BPH tissues (or vice versa). For the purpose of comparison, a variant of SF-LDA was also applied in which only genes that perfectly separate BPH from G4 in the training data were used. This variant performed similarly to SF-LDA for small numbers of genes (as it is expected that a large fraction of the genes ranked high by SF-LDA also separate perfectly the training set). For large numbers of genes it performed similarly to SF-SVM (all genes that do not separate perfectly the training set get a weight of zero, all the others are selected, like for SF-SVM). But it did not perform better than SF-SVM, so it was not retained.

Clustering

Another technique that Affymetrix uses is clustering, and more specifically Self Organizing Maps (SOM). Clustering can be used to group genes into clusters and define "super-genes" (cluster centers). The super-genes that are over-expressed for G4 and underexpressed for BPH examples (or vice versa) are identified (visually). Their cluster members are selected. The intersection of these selected genes and genes selected with the T-test is taken to obtain the final gene subset.

Clustering is a means of regularization that reduces the dimensionality of feature space prior to feature selection. Feature selection is performed on a smaller number of "super-genes". Combining clustering and feature selection in this way on this particular data set will be the object of future work.

V. Conclusions

Meaningful feature selection can be performed with as little as 17 examples and 7129 features. On this data set single feature SVM performs the best.

EXAMPLE 5

Application of SVM RFE to Lymphoma

SVM RFE outperforms Golub's method significantly in a wide range of values of training dataset sizes and the number of selected input variables on certain data sets. This data set includes 96 tissue samples (72 lymphoma and 24 non-cancer) for which 4026 gene expression coefficients were recorded. A simple preprocessing was performed and missing values were replaced by zeros. The dataset was split into training and test sets in various proportions and each experiment was repeated on 96 different splits. Variable selection was performed with the RFE algorithm by removing genes with smallest weights and retraining repeatedly.

Inputs

Training examples $$X_0=[x_1, x_2, \ldots x_k, \ldots x_l]^T$$

Class labels $$y=[y_1, y_2, \ldots y_k, \ldots y_l]^T$$

Initialize:

Subset of surviving features $$s=[1, 2, \ldots n]$$

Feature ranked list $$r=[\ ]$$

Repeat until s=[ ]

Restrict training examples to good feature indices $$X=X_0(\lambda, s)$$

Train the classifier $\alpha=SVM\text{-train}(X,y)$

Compute the weight vector of dimension length(s)

$$w=\sum_k \alpha_k y_k x_k$$

Compute the ranking criteria $$c_i=(w_i)^2, \text{ for all } i$$

Find the feature with smallest ranking criterion $$f=argmin(c)$$

Update feature ranked list $$r=[s(f), r]$$

Eliminate the feature with smallest ranking criterion $$s=s(1{:}f-1, f+1{:}\text{length}(s))$$

Output:

Feature ranked list r.

Figure 30:
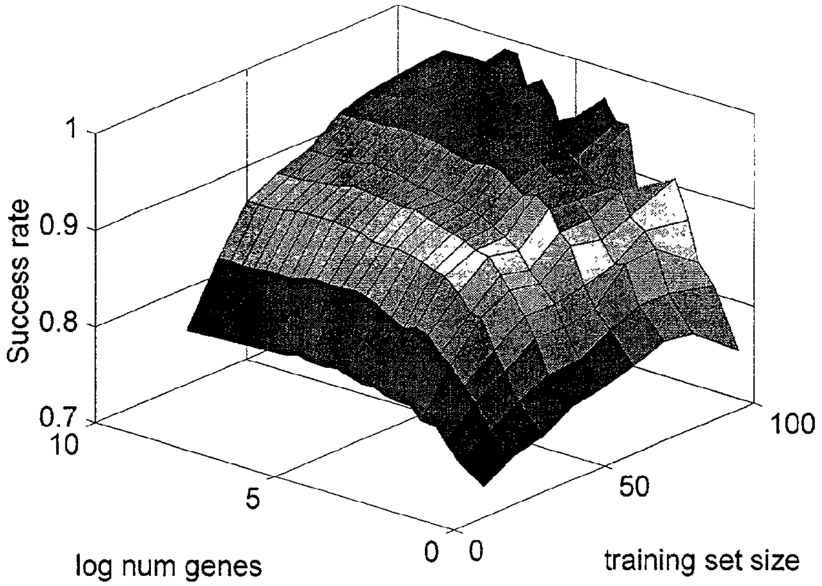
FIG. 30 is a plot of the learning curve for a SVM-RFE with varied gene numbers.
Figure 31:
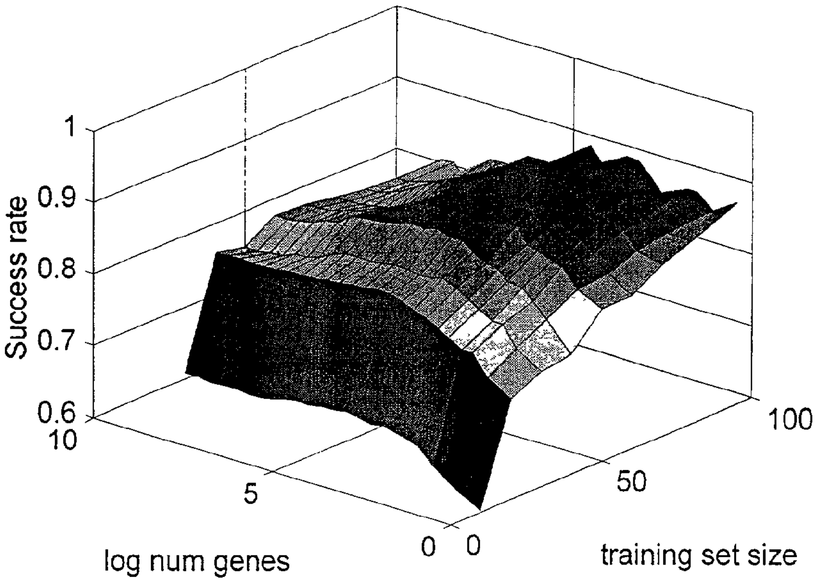
FIG. 31 is a plot of the learning curve with varied gene number using the Golub method.

The gene set size was decreased logarithmically, apart from the last 64 genes, which were removed one at a time according to the RFE method. FIG. 30, demonstrates the learning curves when the number of genes varies in the gene elimination process. The success rate is represented as a function of the training set size and the number of genes retained in the gene elimination process. For comparison, FIG. 31 depicts the results obtained by a competing technique by Golub that uses a correlation coefficient to rank order genes.

$$w_i=(\mu_i(+)-\mu_i(-))/(\sigma_i(+)+\sigma_i(-))$$

where $\mu_i$ and $\sigma_i$ are the mean and standard deviation of the gene expression values of a particular gene i for all the patients of class (+) or class (−), i=1, . . . . n. Large positive $w_i$ values indicate strong correlation with class (+) whereas large negative $w_i$ values indicate strong correlation with class (−). One method is to select an equal number of genes with positive and with negative correlation coefficient.

Classification is performed using the top ranking genes, each contributing to the final decision by voting according to the magnitude of their correlation coefficient. Other comparisons with a number of other methods including Fisher's discriminant, decision trees, and nearest neighbors have confirmed the superiority of SVMs.

It should be understood, of course, that the foregoing relates only to preferred embodiments of the present invention and that numerous modifications or alterations may be made therein without departing from the spirit and the scope of the invention as set forth in the appended claims. Such alternate embodiments are considered to be encompassed within the spirit and scope of the present invention. Accordingly, the scope of the present invention is described by the appended claims and is supported by the foregoing description.

REFERENCES

All of the references are herein incorporated in their entirety.

(Alon, et al., 1999) Broad patterns of gene expression revealed by clustering analysis of tumor and normal colon cancer tissues probed by oligonucleotide arrays. PNAS vol. 96 pp. 6745–6750, June 1999, Cell Biology.

(Eisen, M. B., et al., 1998) Cluster analysis and display of genome-wide expression patterns *Proc. Natl. Acad. Sci. USA*, Vol. 95, pp. 14863–14868, December 1998, Genetics.

(Alizadeh, A. A., et al., 2000) Distinct types of diffuse large B-cell lymphoma identified by gene expression profiling. Nature, Vol. 403, Issue 3, February, 2000.

(Brown, M. P. S., et al. 2000) Knowledge-based analysis of microarray gene expression data by using support vector machines. PNAS, Vol. 97, no. 1: 262–267, January, 2000.

(Perou, C. M., et al., 1999) Distinctive gene expression patterns in human mammar epithelial cells and breast cancers, Proc. Natl. Acad. Sci. USA, Vol. 96, pp. 9212–9217, August 1999, Genetics (Ghina, C., et al., 1998) Altered Expression of Heterogeneous Nuclear Ribonucleoproteins and SR Factors in Human, Cancer Research, 58, 5818–5824, Dec. 15, 1998.

(Duda, R. O., et al., 1973) Pattern classification and scene analysis. Wiley. 1973.

(Golub, et al., 1999) Molecular Classification of Cancer: Class Discovery and Class Prediction by Gene Expression Monitoring. Science Vol 286, October 1999.

(Guyon, I., et al., 1992) Structural risk minimization for character recognition. Advances in Neural Information Processing Systems 4 (NIPS 91), pages 471–479, San Mateo Calif., Morgan Kaufmann. 1992.

(Guyon, I., et al., 1996) Discovering informative patterns and data cleaning. Advances in Knowledge Discovery and Data Mining, pages 181–203. MIT Press. 1996.

(Vapnik, V. N., 1998) Statistical Learning Theory. Wiley Interscience. 1998.

(Guyon, I. et al., 1998) What size test set gives good error rate estimates? PAMI, 20 (1), pages 52–64, IEEE. 1998.

(Boser, B. et al., 1992) An training algorithm for optimal margin classifiers. In Fifth Annual Workshop on Computational Learning Theory, pages 144–152, Pittsburgh, ACM. 1992.

(Cristianini, N., et al., 1999) An introduction to support vector machines. Cambridge University Press. 1999.

(Kearns, M., et al. 1997). An experimental and theoretical comparison of model selection methods. Machine Learning 27: 7–50. 1997.

(Shürmann, J., 1996) Pattern Classification. Wiley Interscience. 1996.

(Mozer, T., et al. 1999) Angiostatin binds ATP synthase on the surface of human endothelial cells, PNAS, Vol. 96, Issue 6, 2811–2816, Mar. 16, 1999, Cell Biology.

(Oliveira, E. C., 1999) Chronic *Trypanosoma cruzi* infection associated to colon cancer. An experimental study in rats. Resumo di Tese. Revista da Sociedade Brasileira de Medicina Tropical 32(1):81–82, January–February, 1999.

(Karakiulakis, G., 1997) Increased Type IV Collagen-Degrading Activity in Metastases Originating from Primary Tumors of the Human Colon, Invasion and Metastasis, Vol. 17, No. 3, 158–168, 1997.
(Aronson, 1999) Remodeling the Mammary Gland at the Termination of Breast Feeding: Role of a New Regulator Protein BRP39, The Beat, University of South Alabama College of Medicine, July, 1999.
(Macalma, T., et al. 1996) Molecular characterization of human zyxin. Journal of Biological Chemistry. Vol. 271, Issue 49, 31470–31478, December, 1996.
(Harlan, D. M., et al. 1991) The human myristoylated alanine-rich C kinase substrate (MARCKS) gene (MACS). Analysis of its gene product, promoter, and chromosomal localization. Journal of Biological Chemistry, Vol. 266, Issue 22, 14399–14405, August, 1991.
(Thorsteinsdottir, U., et al. 1999) The oncoprotein E2A-Pbx1a collaborates with Hoxa9 to acutely transform primary bone marrow cells. Molecular Cell Biology, Vol. 19, Issue 9, 6355–66, September, 1999.
(Osaka, M., et al. 1999) MSF (MLL septin-like fusion), a fusion partner gene of MLL, in a therapy-related acute myeloid leukemia with a t(21; 17)(q23;q25). Proc Natl Acad Sci USA. Vol. 96, Issue 11, 6428–33, May, 1999.
(Walsh, J. H., 1999) Epidemiologic Evidence Underscores Role for Folate as Foiler of Colon Cancer. Gastroenterology News. Gastroenterology. 116:3–4, 1999.
(Aerts, H., 1996) Chitotriosidase—New Biochemical Marker. Gauchers News, March, 1996.
(Fodor, S. A., 1997) Massively Parallel Genomics. Science. 277:393–395, 1997.
(Schölkopf, B., et al. 1999) Estimating the Support of a High-Dimensional Distribution, in proceeding of NIPS 1999.

The invention claimed is:

1. A computer-implemented method for identifying patterns in data, the method comprising:

(a) inputting into at least one support vector machine of a plurality of support vector machines a training set having known outcomes, the at least one support vector machine comprising a decision function having a plurality of weights, each having a weight value, wherein the training set comprises features corresponding to the data and wherein each feature has a corresponding weight;

(b) optimizing the plurality of weights so that classifier error is minimized;

(c) computing ranking criteria using the optimized plurality of weights;

(d) eliminating at least one feature corresponding to the smallest ranking criterion;

(e) repeating steps (a) through (d) for a plurality of iterations until a subset of features of pre-determined size remains; and (f) inputting into the at least one support vector machine a live set of data wherein the features within the live set are selected according to the subset of features.

2. The method of claim 1, wherein the at least one support vector machine is a soft margin support vector machine.

3. The method of claim 1, wherein the ranking criterion corresponding to a feature is calculated by squaring the optimized weight for the corresponding feature.

4. The method of claim 1, wherein the decision function is a quadratic function.

5. The method of claim 1, wherein step (d) comprises eliminating a plurality of features corresponding to the smallest ranking criteria in a single iteration of steps (a) through (d).

6. The method of claim 1, wherein step (d) comprises eliminating a plurality of features corresponding to the smallest ranking criteria in at least the first iteration of steps (a) through (d) and in later iterations, eliminating one feature for each iteration.

7. The method of claim 1, wherein step (d) comprises eliminating a plurality of features corresponding to the smallest ranking criteria so that the number of features is reduced by a factor of two for each iteration.

8. The method of claim 1, wherein the training set and the live set each comprise gene expression data obtained from DNA micro-arrays.

9. The method of claim 1, further comprising pre-processing the training set and the live set so that the features are comparably scaled.

10. The method of claim 1, wherein step (e) further comprises using a new support vector machine for each iteration.

11. The method of claim 1, further comprising the steps of:

pre-processing the training data set using unsupervised clustering to generate a plurality of data clusters;

selecting a cluster center from each of a plurality of data clusters;

using the cluster centers to perform steps (b) to (e).

12. The method of claim 1, further comprising, after step (e), post-processing the optimum subset of features to generate a plurality of clusters, wherein each feature in the optimum subset of features is a cluster center.

13. A computer-implemented method for identifying determinative genes for use in diagnosis, prognosis or treatment of a disease, the method comprising:

(a) inputting into a support vector machine a training data set of gene expression data having known outcomes with respect to the disease, the support vector machine comprising a decision function having a plurality of weights, each having a weight value, wherein the training set comprises features corresponding to the gene expression data and each feature has a corresponding weight;

(b) optimizing the plurality of weights so that classifier error is minimized;

(c) computing ranking criteria using the optimized plurality of weights;

(d) eliminating at least one feature corresponding to the smallest ranking criterion;

(e) repeating steps (a) through (d) for a plurality of iterations until an optimum subset of features remains; and (f) inputting into the support vector machine a live data set of gene expression data wherein the features within the live data set are selected according to the optimum subset of features.

14. The method of claim 13, wherein step (d) comprises eliminating a plurality of features corresponding to the smallest ranking criteria in a single iteration of steps (a) through (d).

15. The method of claim 13, wherein step (d) comprises eliminating a plurality of features corresponding to the smallest ranking criteria in at least the first iteration of steps (a) through (d) and in later iterations, eliminating one feature for each iteration.

16. The method of claim 13, wherein step (d) comprises eliminating a plurality of features corresponding to the smallest ranking criteria so that the number of features is reduced by a factor of two for each iteration.

17. The method of claim 13, wherein step (e) further comprises using a new support vector machine for each iteration.

18. The method of claim 13, further comprising preprocessing the training set to decrease skew in the data distribution.

19. A computer-implemented method for identifying patterns in biological data, the method comprising:

(a) inputting into at least some of a plurality of support vector machines a training data set, wherein the training data set comprises features corresponding to the biological data and each feature has a corresponding weight, and wherein each support vector machine comprises a decision function having a plurality of weights;

(b) optimizing the plurality of weights so that classification confidence is optimized;

(c) computing ranking criteria using the optimized plurality of weights;

(d) eliminating at least one feature corresponding to the smallest ranking criteria;

(e) repeating steps (a) through (d) for a plurality of iterations until an optimum subset of features remains; and (f) inputting into the plurality of support vector machines a live set of biological data wherein the features within the live set are selected according to the optimum subset of features.

20. The method of claim 19, wherein step (e) further comprises using a new support vector machine for each iteration.

21. The method of claim 19, wherein step (d) comprises eliminating a plurality of features corresponding to the smallest ranking criteria in a single iteration of steps (a) through (d).

22. The method of claim 19, wherein step (d) comprises eliminating a plurality of features corresponding to the smallest ranking criteria in at least the first iteration of steps (a) through (d) and in later iterations, eliminating one feature for each iteration.

23. The method of claim 19, wherein step (d) comprises eliminating a plurality of features corresponding to the smallest ranking criteria so that the number of features is reduced by a factor of two for each iteration.

* * * * *